US012649794B2

(12) United States Patent
Margall Ducos et al.

(10) Patent No.: US 12,649,794 B2
(45) Date of Patent: Jun. 9, 2026

(54) ANTI-GALECTIN-9 ANTIBODY AND USES THEREOF

(71) Applicant: HIFIBIO, INC., Cambridge, MA (US)

(72) Inventors: Germain Margall Ducos, Saint Maurice (FR); Rachel Pacherie, Sceaux (FR); Nicola Arturo Aldo Beltraminelli, Villeurbanne (FR); Francisco Adrian, Belmont, MA (US); Liang Schweizer, Cambridge, MA (US); Muriel David, Cambridge, MA (US); Yun-Yueh Lu, Cambridge, MA (US)

(73) Assignee: HIFIBIO, INC., Cambridge, MA (US)

( * ) Notice: Subject to any disclaimer, the term of this patent is extended or adjusted under 35 U.S.C. 154(b) by 1007 days.

(21) Appl. No.: 17/789,961

(22) PCT Filed: Jan. 6, 2021

(86) PCT No.: PCT/CN2021/070473

§ 371 (c)(1),
(2) Date: Jun. 29, 2022

(87) PCT Pub. No.: WO2021/139682

PCT Pub. Date: Jul. 15, 2021

(65) Prior Publication Data

US 2023/0054718 A1     Feb. 23, 2023

Related U.S. Application Data

(60) Provisional application No. 62/957,910, filed on Jan. 7, 2020.

(51) Int. Cl.
| | |
|---|---|
| *C07K 16/28* | (2006.01) |
| *A61K 39/00* | (2006.01) |
| *A61P 35/00* | (2006.01) |

(52) U.S. Cl.
CPC .......... *C07K 16/2851* (2013.01); *A61P 35/00* (2018.01); *C07K 16/2818* (2013.01); *A61K 2039/505* (2013.01); *A61K 2039/507* (2013.01); *C07K 2317/24* (2013.01); *C07K 2317/55* (2013.01); *C07K 2317/565* (2013.01); *C07K 2317/622* (2013.01); *C07K 2317/92* (2013.01)

(58) Field of Classification Search
CPC ............ C07K 16/2851; C07K 16/2818; C07K 2317/24; C07K 2317/55; C07K 2317/565; C07K 2317/622; C07K 2317/92; C07K 2317/76; C07K 2317/33; C07K 2317/73; A61P 35/00; A61K 2039/505; A61K 2039/507
See application file for complete search history.

(56) References Cited

U.S. PATENT DOCUMENTS

| | | | |
|---|---|---|---|
| 5,225,539 | A | 7/1993 | Winter |
| 5,530,101 | A | 6/1996 | Queen et al. |
| 5,585,089 | A | 12/1996 | Queen et al. |
| 5,693,761 | A | 12/1997 | Queen et al. |
| 5,693,762 | A | 12/1997 | Queen et al. |
| 6,180,370 | B1 | 1/2001 | Queen et al. |
| 2017/0283499 | A1 | 10/2017 | Delhem et al. |
| 2019/0127472 | A1 | 5/2019 | Koide et al. |

FOREIGN PATENT DOCUMENTS

| | | | |
|---|---|---|---|
| CA | 3134942 | A1 | 10/2020 |
| RU | 2397249 | C2 | 8/2010 |
| WO | 2006105021 | A2 | 10/2006 |
| WO | 2006122150 | A1 | 11/2006 |
| WO | 2007005874 | A2 | 1/2007 |
| WO | 2007075598 | A2 | 7/2007 |
| WO | 2008036642 | A2 | 3/2008 |
| WO | 2008036653 | A2 | 3/2008 |
| WO | 2008132601 | A1 | 11/2008 |
| WO | 2009044273 | A2 | 4/2009 |
| WO | 2009073620 | A2 | 6/2009 |
| WO | 2010019570 | A2 | 2/2010 |
| WO | 2011028683 | A1 | 3/2011 |
| WO | 2011056652 | A1 | 5/2011 |
| WO | 2011070024 | A1 | 6/2011 |
| WO | 2011109400 | A2 | 9/2011 |
| WO | 2011131407 | A1 | 10/2011 |
| WO | 2011140249 | A2 | 11/2011 |
| WO | 2012032433 | A1 | 3/2012 |
| WO | 2012142237 | A1 | 10/2012 |
| WO | 2012145493 | A1 | 10/2012 |
| WO | 2013079174 | A1 | 6/2013 |
| WO | 2013087699 | A1 | 6/2013 |
| WO | 2013119716 | A1 | 8/2013 |
| WO | 2013132044 | A1 | 9/2013 |
| WO | 2013169264 | A1 | 11/2013 |
| WO | 2014008218 | A1 | 1/2014 |

(Continued)

OTHER PUBLICATIONS

U.S. Appl. No. 18/995,102, filed Jul. 14, 2023, Olsen, David.*
Lhuillier C, et al. Characterization of neutralizing antibodies reacting with the 213-224 amino-acid segment of human galectin-9. PLoS One. Sep. 11, 2018;13(9):e0202512. doi: 10.1371/journal.pone.0202512. PMID: 30204750; PMCID: PMC6133441. (Year: 2018).*
Angal et al. "A single amino acid substitution abolishes the heterogeneity of chimeric mouse/human (IgG4) antibody" Jan. 1993, Mol. Immunol. 30(1):105-108.

(Continued)

*Primary Examiner* — Maher M Haddad
*Assistant Examiner* — Alec Jon Peters
(74) *Attorney, Agent, or Firm* — Ice Miller LLP

(57) ABSTRACT

The invention provides humanized monoclonal antibodies against Gal9, and method of using the antibodies to treat cancer, including combination therapy with antagonists of the PD-1/PD-L1 immune checkpoint.

26 Claims, 15 Drawing Sheets

Specification includes a Sequence Listing.

(56) References Cited

FOREIGN PATENT DOCUMENTS

| | | | |
|---|---|---|---|
| WO | 2014036357 | A1 | 3/2014 |
| WO | 2015031667 | A2 | 3/2015 |
| WO | 2019197675 | A1 | 10/2019 |
| WO | 2020018364 | A1 | 1/2020 |
| WO | 2020223702 | A1 | 11/2020 |
| WO | 2021139682 | A1 | 7/2021 |
| WO | 2024015993 | A1 | 1/2024 |

OTHER PUBLICATIONS

Clackson et al. "Making antibody fragments using phage display libraries" Aug. 15, 1991, Nature 352(6336):624-628.

Gennaro, "Remington: The Science and Practice of Pharmacy" 20th ed., 2003 (Cover and TOC).

Green et al. "Molecular Cloning: A Laboratory Manual" 4th Ed, 2012, Cold Spring Harbor Laboratory Press, Woodbury, NY (2,028 pages).

Haeckel et al. "XTEN as Biological Alternative to PEGylation Allows Complete Expression of a Protease-Activatable Killin-Based Cytostatic2" Jun. 13, 2016, PLoS One 11(6):e0157193.

Harlow and Lane, Antibodies, A Laboratory Manual, 1st Ed., 1988, Cold Springs Harbor Press—726 Pages—Background only—Abstract only (ISBN: 0879693142).

Hoogenboom et al. "By-passing Immunization: Human antibodies from synthetic repertoires of germline VH gene segments rearranged in vitro" 1992, J. Mol. Biol. 227(2):381-388.

International Search Report and Written Opinion for PCT/CN2021/070473 mailed Jun. 14, 2021.

International Search Report and Written Opinion for PCT/CN2021/103889 mailed Mar. 31, 2022.

Kibbe et al., Handbook of Pharmaceutical Excipients, 3rd ed., 2000, Pharmaceutical Press (12 pages).

Marks et al. "By-passing immunization. Human antibodies from V-gene libraries displayed on phage" Dec. 1991, J. Mol. Biol. 222(3):581-597.

Morel et al. "Monoclonal antibodies to bovine serum albumin: affinity and specificity determinations" Jan. 1988, Molec. Immunol. 25(1):7-15.

Morimoto et al. "Single-step purification of F(ab')2 fragments of mouse monoclonal antibodies (immunoglobulins G1) by hydropho-bic interaction high performance liquid chromatography using TSKgel Phenyl-5PW" Mar. 1992, J. Biochem. Biophys. Methods 24(1-2):107-117.

Morrison et al. "Transfectomas provide novel chimeric antibodies" Sep. 20, 1985, Science 229(4719):1202-1207.

Oi et al. "Chimeric Antibodies" 1986, BioTechniques 4:214-221.

Pluckthun, "Antibodies from *Escherichia coli*."1994, The Pharmacology of Monoclonal Antibodies 113:269-315, Rosenberg and Moore eds., Springer-Verlag, NY—Background only—Abstract only.

Raybould et al. "Five Computational Developability Guidelines for Therapeutic Antibody Profiling" 2019 PNAS USA 116(10):4025-4030.

Safdari et al. "Antibody humanization methods—a review and update" 2013, Biotech. And Genetic Engineering Reviews 29(2):175-186.

Sitaraman et al. "High-throughput protein expression using cell-free system" 2009, Methods Mol. Biol. 498:229-244.

Strickley et al "A review of formulatons of commercially available antibodies" Jul. 2021, J. Pharm. Sci. 110(7):2590-2608.e56.

Tyner et al. "Functional Genomic Landscape of Acute Myeloid Leukaemia" Oct. 2018, Nature 562(7728):526-531.

Valldorf et al. "Antiobody Display Technologies: selecting the cream of the crop" 2022, Biol. Chem. 403(506):4550477.

Warszawski et al. "Optimizing Antibody Affinity and Stability by the Automated Design of the Variable Light-Heavy Chain Interfaces" Aug. 23, 2019, PloS Comput. Biol. 16(10):e100207 (http://doi.org/10.1371/journal.pcbi.1007207).

Weber et al. "From rabbit antibody repertoires to rabbit monoclonal antibodies" Mar. 24, 2017, Exp. Mol. Med. 49: e305.

Wu et al. "Galectin-9-CD44 interaction enhances stability and function of adaptive regulatory T cells" 2014, Immunity 41(2):270-282.

Yang et al. "Elevated Galectin-9 Suppresses Th1 Effector Function and Induces Apoptosis of Activated CD4+ T Cells in Osteoarthritis" Jun. 2017, Inflammation 40(3):1062-1071 (abstract).

Zapata et al. "Engineering linear F(ab')2 fragments for efficient production in *Escherichia coli* and enhanced antiproliferative activity" Oct. 1, 1995, Protein Eng. 8(10):1057-1062.

Nasonov, "Immune Checkpoint Inhibition and Autoimmunity: Rhemuatological Problems", Rheumatology Science and Practice, 2018, 56(1):5-9 (in Russian, with English Abstract).

International Search Report and Written Opinion for PCT/US2023/070259 dated Dec. 13, 2023 (21 pages).

* cited by examiner

FIG. 5

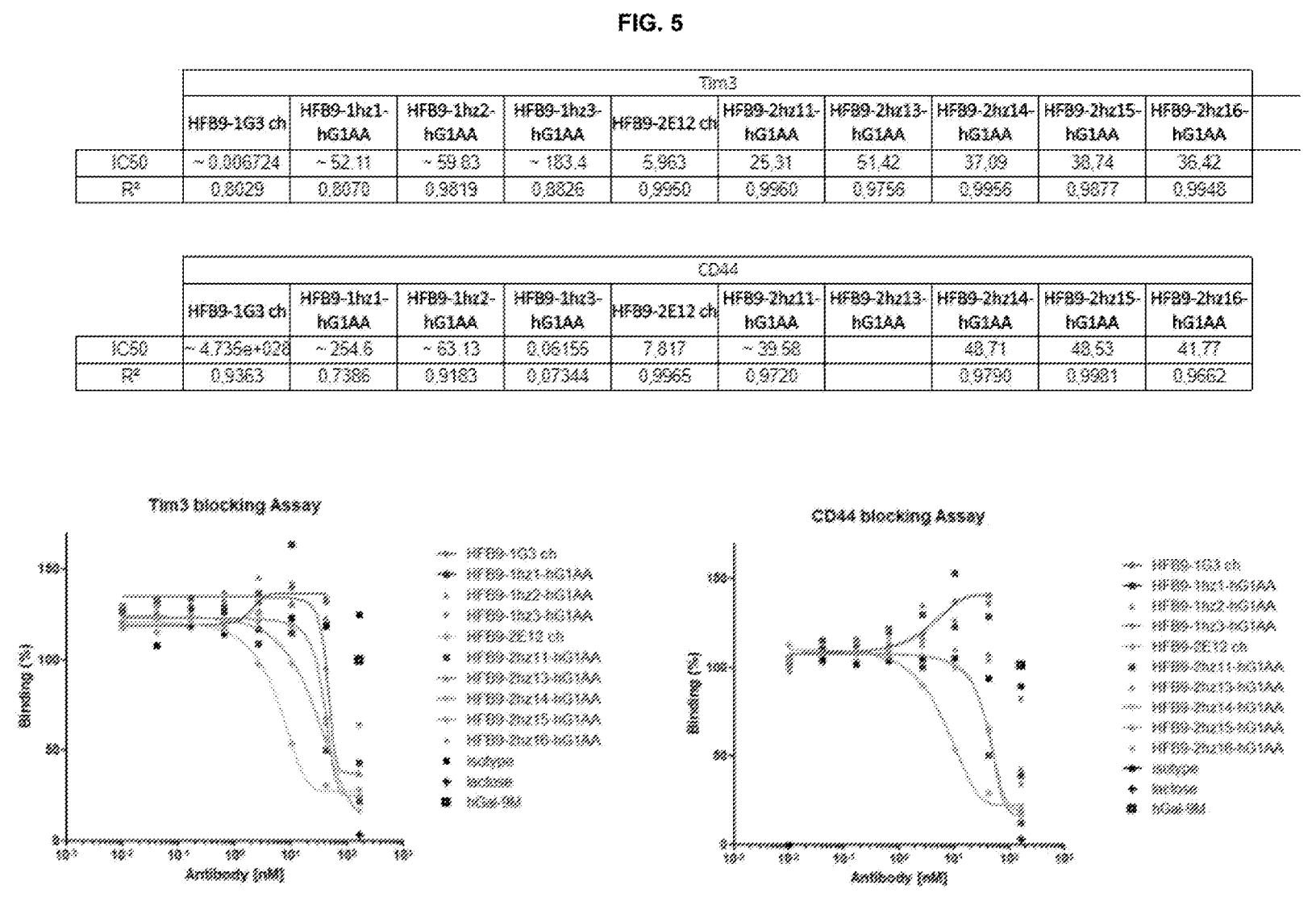

Tim3

| | HFB9-1G3 ch | HFB9-1hz1-hG1AA | HFB9-1hz2-hG1AA | HFB9-1hz3-hG1AA | HFB9-2E12 ch | HFB9-2hz11-hG1AA | HFB9-2hz13-hG1AA | HFB9-2hz14-hG1AA | HFB9-2hz15-hG1AA | HFB9-2hz16-hG1AA |
|---|---|---|---|---|---|---|---|---|---|---|
| IC50 | ~ 0.006724 | ~ 52.11 | ~ 59.83 | ~ 183.4 | 5.963 | 25.31 | 51.42 | 37.09 | 38.74 | 36.42 |
| R² | 0.8029 | 0.8070 | 0.9819 | 0.8826 | 0.9950 | 0.9960 | 0.9756 | 0.9956 | 0.9677 | 0.9948 |

CD44

| | HFB9-1G3 ch | HFB9-1hz1-hG1AA | HFB9-1hz2-hG1AA | HFB9-1hz3-hG1AA | HFB9-2E12 ch | HFB9-2hz11-hG1AA | HFB9-2hz13-hG1AA | HFB9-2hz14-hG1AA | HFB9-2hz15-hG1AA | HFB9-2hz16-hG1AA |
|---|---|---|---|---|---|---|---|---|---|---|
| IC50 | ~ 4.736e+028 | ~ 254.6 | ~ 63.13 | 0.06155 | 7.817 | ~ 39.58 | | 48.71 | 48.53 | 41.77 |
| R² | 0.9363 | 0.7386 | 0.9183 | 0.07344 | 0.9965 | 0.9720 | | 0.9730 | 0.9981 | 0.9662 |

CD44 Blocking Assay

Tim3 Blocking Assay

Mean Tumor Volume ± SEM

Isotype control, 10mg/kg, 10μL/g, i.p., Day 1, 4, 7, 10, 13, 16, 19

HFB9-2 10mg/kg, 10μL/g, i.p., Day 1, 4, 7, 10, 13, 16, 19

Anti-mPD-1 10mg/kg, 10μL/g, i.p., Day 1, 4, 7, 10

HFB9-2 10mg/kg, 10μL/g, i.p., Day 1, 4, 7, 10, 13, 16, 19 +Anti-mPD-1 10mg/kg, 10μL/g, i.p., Day 1, 4, 7, 10

| Number of values | M0 | M1 | M2 | M3 | M4 | M5 | M7 | Healthy BM MNC | Healthy CD34 |
|---|---|---|---|---|---|---|---|---|---|
| | 5 | 7 | 7 | 8 | 17 | 22 | 1 | 19 | 13 |
| 25% Percentile | 6.275 | 6.770 | 6.178 | 3.635 | 6.473 | 6.494 | 5.660 | 5.908 | 6.290 |
| Median | 6.633 | 6.865 | 6.291 | 3.714 | 6.833 | 6.682 | 5.660 | 6.177 | 6.379 |
| 75% Percentile | 6.912 | 7.518 | 7.085 | 4.466 | 7.153 | 7.153 | 5.660 | 6.347 | 6.491 |

Kaplan-Meier survival curve
endpoint: tumor volume 3000mm³

ANTI-GALECTIN-9 ANTIBODY AND USES THEREOF

REFERENCE TO RELATED APPLICATION

This application is the U.S. national phase under 35 U.S.C. § 371 of International Application No. PCT/CN2021/070473, filed Jan. 6, 2021, which claims priority to U.S. Provisional Patent Application No. 62/957,910, filed on Jan. 7, 2020, the entire contents of which including all sequences and drawings are incorporated herein by reference.

REFERENCE TO SEQUENCE LISTING SUBMITTED ELECTRONICALLY

This application contains a sequence listing, which is submitted electronically via the patent electronic filing system as an ASCII formatted sequence listing with a file name "065798.13US2_SequenceListing.txt" and a creation date of Nov. 10, 2025 and having a size of 51,877 bytes. The sequence listing submitted via the patent electronic filing system is part of the specification and is herein incorporated by reference in its entirety.

BACKGROUND OF THE INVENTION

Galectin-9 (or Gal9) is a member of the galectin (or type-S lectin) family of proteins having at least 15 members in vertebrates, including 10 in humans. Galectin-9 is a soluble 34-39 kDa protein without a leader peptide, yet is nevertheless secreted via a non-classical mechanism. It interacts preferentially with beta-galactoside residues of glycoproteins and glycolipids. In humans, Galectin-9 exists in three isoforms, long, medium and short.

Galectin-9 is one of the most studied ligand for HAVCR2 (TIM-3), and is expressed on various hematological malignancies, such as CLL, MDS, Hodgkin and Non-Hodgkin lymphomas, AML, as well as solid tumors such as lung cancer, breast cancer, and hepatocellular carcinoma.

HAVCR2/galectin-9 interaction has been found to attenuate T-cell expansion and effectors function in the tumor microenvironment and chronic infections. Moreover, galectin-9 contributed to tumorigenesis by tumor cell transformation, cell-cycle regulation, angiogenesis, and cell adhesion.

Galectin-9 is also directly expressed by regulatory T lymphocytes (or Tregs), and its expression is increased during Treg activation. Meanwhile, Galectin-9 is very weakly expressed by effector T lymphocytes (such as CD8 CTLs), and this expression disappears during effector T lymphocyte activation. Inhibition of Galectin-9 by an anti-Gal9 antibody has been found to inhibit the suppressor activity of Tregs.

Wu et al. (*Immunity* 41 (2): 270-282, 2014) reported that Gal-9 is critical in regulating the immune response. Gal-9 is highly expressed by induced regulatory T cells (iTreg) and was crucial for the generation and function of iTreg cells, but not natural regulatory T (nTreg) cells. Gal-9 expression in iTreg cells was driven by the transcription factor Smad3, forming a feed-forward loop, which further promoted Foxp3 expression. Gal-9 increased iTreg cell stability and function by directly binding to its receptor CD44, which formed a complex with transforming growth factor-β (TGF-β) receptor I (TGF-βRI), and activated Smad3. Gal-9 signaling was further found to regulate iTreg cell induction by dominantly acting through the CNS1 region of the Foxp3 locus. Exogenous Gal-9, in addition to being an effector molecule for Treg cells, acts synergistically with TGF-β to enforce iTreg cell differentiation and maintenance.

Various types of T lymphocytes normally develop into, for example "effector" cells or effector T lymphocytes, which will fulfil specialized immune functions for defending the host organism. Thus the CD4+ T lymphocytes or auxiliary T lymphocytes, secrete major cytokines assisting in particular the B lymphocytes in their humoral function (the production of specific antibodies) and the CD8+ T lymphocytes in their cytotoxic activity.

Another population of CD4+ T lymphocytes consists of natural regulatory T lymphocytes, or "regulatory T lymphocytes (Tregs)." They constitutively overexpress the CD25 molecule (hence also called "CD4+CD25+") and the Foxp3 transcription factor. This small percentage of CD4+CD25+ T lymphocytes has the particularity of negatively regulating the actors of the immune response that would have recognized various auto-antigens by their TCRs. Regulator T lymphocytes also fulfil a major role in the physiology of the immune system in particular for protecting the organism against the emergence of autoimmune illnesses. In other words, Tregs are a sub-population of natural regulatory T lymphocytes (or "nTregs") characterized by an expression constituting CD25, CTLA-4 and GITR, and by a specific expression of the transcription factor Foxp3.

The Tregs exert immunosuppressor activity on effector T lymphocytes. Such activity, once activated, in a pathological situation such as tumor, promotes tumor growth. Thus, the suppressor activity of Tregs can be understood as the activity that reduces the anti-tumoral immune responses, by inhibiting the function of effector T lymphocytes.

Galectin-9 is mainly associated with tumor immunosuppression resulting from interaction with different immune receptors. For example, Gal9 inhibits Th1 responses and induces peripheral tolerance, as evidenced by decreased Th1 apoptosis upon Gal9 blockade, increased susceptibility of Gal9 knock-out mice to CIA (collagen-induced arthritis), and prolonged graft survival and AID suppression upon Gal9 administration. Gal9 also regulates peripheral NK cell function to promote materno-fetal tolerance, promotes the expansion of MDSCs, and synergizes with TGF-β to promote Treg expansion.

Circulating levels of Gal9 are significantly higher in certain cancer patients compared to healthy control.

SUMMARY OF THE INVENTION

The invention described herein relates to humanized antibodies directed against galectin-9 and the use thereof for the treatment of diseases associated with the suppressor activity of regulatory T lymphocytes (Tregs).

Specifically, the invention described herein provides anti-Gal9 neutralizing antibodies that release immunosuppression in the TME (tumor microenvironment), leading to antitumor activity and clinical response in cancer patients.

The anti-Gal9 neutralizing antibodies of the invention are derivative antibodies based on two anti-Gal9 neutralizing antibodies (Ab1 and Ab2, respectively) disclosed in US 2017-0283499 A1 (filed Jun. 5, 2015, incorporated herein by reference), both of which bind recombinant human Gal9 with sub-nM $EC_{50}$ values, and both block human Gal9-induced apoptosis of CD4+ T cells or expansion of Tregs from peripheral blood of healthy donors. However, these two antibodies differ in that Ab2 blocks recombinant human Gal9 interaction with two immune receptors (R1 and R2), while Ab1 does not.

The inventions described herein provide multiple humanized monoclonal antibodies based on Ab1 and Ab2. These humanized monoclonal antibodies bind to recombinant human and/or murine Gal9, block Gal9-induced Th1 apoptosis, and block Gal9-induced Treg expansion. More importantly, the humanized monoclonal antibodies of the invention acted synergistically with antibodies targeting the PD-1/PD-L1 immune checkpoint, thus providing a therapeutic advantage for overcoming resistance encountered in immune therapy (e.g., resistance in ineffectiveness using PD-1 and PD-L1 antagonists).

The antibodies of the invention have wide use in treating hematological cancers such as AML and DLBCL, as well as solid cancers such as breast cancer, head and neck cancer, lung cancer, melanoma (including uveal melanoma), colon cancer, renal carcinoma, ovarian cancer, liver cancer, and prostate cancer.

Thus one aspect of the invention provides an isolated monoclonal antibody, or an antigen-binding fragment thereof, wherein said monoclonal antibody or antigen-binding fragment thereof is specific for Galectin-9, and wherein said monoclonal antibody comprises: (1a) a heavy chain variable region (HCVR), comprising a HCVR CDR1 sequence of SEQ ID NO: 2, a HCVR CDR2 sequence of SEQ ID NO: 4, and a HCVR CDR3 sequence of SEQ ID NO: 6; and, (1b) a light chain variable region (LCVR), comprising a LCVR CDR1 sequence of SEQ ID NO: 10, a LCVR CDR2 sequence of SEQ ID NO: 12, and a LCVR CDR3 sequence of SEQ ID NO: 14; or (2a) a heavy chain variable region (HCVR), comprising a HCVR CDR1 sequence of SEQ ID NO: 18, a HCVR CDR2 sequence of SEQ ID NO: 20, and a HCVR CDR3 sequence of SEQ ID NO: 22; and, (2b) a light chain variable region (LCVR), comprising a LCVR CDR1 sequence of SEQ ID NO: 26, a LCVR CDR2 sequence of SEQ ID NO: 28, and a LCVR CDR3 sequence of SEQ ID NO: 30; or (3a) a heavy chain variable region (HCVR), comprising a HCVR CDR1 sequence of SEQ ID NO: 34, a HCVR CDR2 sequence of SEQ ID NO: 36, and a HCVR CDR3 sequence of SEQ ID NO: 38; and, (3b) a light chain variable region (LCVR), comprising a LCVR CDR1 sequence of SEQ ID NO: 42, a LCVR CDR2 sequence of SEQ ID NO: 44, and a LCVR CDR3 sequence of SEQ ID NO: 46; or (4a) a heavy chain variable region (HCVR), comprising a HCVR CDR1 sequence of SEQ ID NO: 50, a HCVR CDR2 sequence of SEQ ID NO: 52, and a HCVR CDR3 sequence of SEQ ID NO: 54; and, (4b) a light chain variable region (LCVR), comprising a LCVR CDR1 sequence of SEQ ID NO: 58, a LCVR CDR2 sequence of SEQ ID NO: 60, and a LCVR CDR3 sequence of SEQ ID NO: 62; or (5a) a heavy chain variable region (HCVR), comprising a HCVR CDR1 sequence of SEQ ID NO: 66, a HCVR CDR2 sequence of SEQ ID NO: 68, and a HCVR CDR3 sequence of SEQ ID NO: 70; and, (5b) a light chain variable region (LCVR), comprising a LCVR CDR1 sequence of SEQ ID NO: 74, a LCVR CDR2 sequence of SEQ ID NO: 76, and a LCVR CDR3 sequence of SEQ ID NO: 78; or (6a) a heavy chain variable region (HCVR), comprising a HCVR CDR1 sequence of SEQ ID NO: 82, a HCVR CDR2 sequence of SEQ ID NO: 84, and a HCVR CDR3 sequence of SEQ ID NO: 86; and, (6b) a light chain variable region (LCVR), comprising a LCVR CDR1 sequence of SEQ ID NO: 90, a LCVR CDR2 sequence of SEQ ID NO: 92, and a LCVR CDR3 sequence of SEQ ID NO: 94; or (7a) a heavy chain variable region (HCVR), comprising a HCVR CDR1 sequence of SEQ ID NO: 98, a HCVR CDR2 sequence of SEQ ID NO: 100, and a HCVR CDR3 sequence of SEQ ID NO: 102; and, (7b) a light chain variable region (LCVR), comprising a LCVR CDR1 sequence of SEQ ID NO: 106, a LCVR CDR2 sequence of SEQ ID NO: 108, and a LCVR CDR3 sequence of SEQ ID NO: 110; or (8a) a heavy chain variable region (HCVR), comprising a HCVR CDR1 sequence of SEQ ID NO: 114, a HCVR CDR2 sequence of SEQ ID NO: 116, and a HCVR CDR3 sequence of SEQ ID NO: 118; and, (8b) a light chain variable region (LCVR), comprising a LCVR CDR1 sequence of SEQ ID NO: 122, a LCVR CDR2 sequence of SEQ ID NO: 124, and a LCVR CDR3 sequence of SEQ ID NO: 128.

In certain embodiments, in the isolated monoclonal antibody or antigen-binding fragment thereof: (1c) the antibody or antigen-binding fragment thereof of (1a) and (1b) further comprises a HFR3 sequence of SEQ ID NO: 5, and optionally further comprises a HFR1 sequence of SEQ ID NO: 1; or (2c) the antibody or antigen-binding fragment thereof of (2a) and (2b) further comprises a HFR3 sequence of SEQ ID NO: 21, and optionally further comprises a HFR1 sequence of SEQ ID NO: 17; or (3c) the antibody or antigen-binding fragment thereof of (3a) and (3b) further comprises a HFR3 sequence of SEQ ID NO: 37, and optionally further comprises a HFR1 sequence of SEQ ID NO: 33; or (4c) the antibody or antigen-binding fragment thereof of (4a) and (4b) further comprises a HFR3 sequence of SEQ ID NO: 53, and optionally further comprises a HFR1 sequence of SEQ ID NO: 49; or (5c) the antibody or antigen-binding fragment thereof of (5a) and (5b) further comprises a HFR3 sequence of SEQ ID NO: 69, and optionally further comprises a HFR1 sequence of SEQ ID NO: 65; or (6c) the antibody or antigen-binding fragment thereof of (6a) and (6b) further comprises a HFR3 sequence of SEQ ID NO: 85, and optionally further comprises a HFR1 sequence of SEQ ID NO: 81; or (7c) the antibody or antigen-binding fragment thereof of (7a) and (7b) further comprises a HFR3 sequence of SEQ ID NO: 101, and optionally further comprises a HFR1 sequence of SEQ ID NO: 97; or (8c) the antibody or antigen-binding fragment thereof of (8a) and (8b) further comprises a HFR3 sequence of SEQ ID NO: 117, and optionally further comprises a HFR1 sequence of SEQ ID NO: 113.

In certain embodiments, in the isolated monoclonal antibody or antigen-binding fragment thereof: (1A) the HCVR sequence is SEQ ID NO: 8; and/or, (1B) the LCVR sequence is SEQ ID NO: 16, or, (2A) the HCVR sequence is SEQ ID NO: 24; and/or, (2B) the LCVR sequence is SEQ ID NO: 32, or, (3A) the HCVR sequence is SEQ ID NO: 40; and/or, (3B) the LCVR sequence is SEQ ID NO: 48, or, (4A) the HCVR sequence is SEQ ID NO: 56; and/or, (4B) the LCVR sequence is SEQ ID NO: 64, or, (5A) the HCVR sequence is SEQ ID NO: 72; and/or, (5B) the LCVR sequence is SEQ ID NO: 80, or, (6A) the HCVR sequence is SEQ ID NO: 88; and/or, (6B) the LCVR sequence is SEQ ID NO: 96, or (7A) the HCVR sequence is SEQ ID NO: 104; and/or, (7B) the LCVR sequence is SEQ ID NO: 112, or (8A) the HCVR sequence is SEQ ID NO: 120; and/or, (8B) the LCVR sequence is SEQ ID NO: 128.

In certain embodiments, the isolated monoclonal antibody or antigen-binding fragment thereof is a humanized antibody, and comprises: (1) the HCVR sequence of SEQ ID NO: 8 and the LCVR sequence of SEQ ID NO: 16; or, (2) the HCVR sequence of SEQ ID NO: 72 and the LCVR sequence of SEQ ID NO: 80.

In certain embodiments, the antigen-binding fragment thereof is an Fab, Fab', F(ab')2, Fd, single chain Fv or scFv, disulfide linked Fv, V-NAR domain, IgNar, intrabody, IgGΔCH2, minibody, F(ab')3, tetrabody, triabody, diabody, single-domain antibody, DVD-Ig, Fcab, mAb2, (scFv)2, or scFv-Fc.

In some embodiment, the monoclonal antibodies of the invention or antigen-binding fragments thereof has an engineered Fc region that abolishes immune effector function. For example, the engineered Fc region of the subject antibody may have a "LALA" double mutation (Leu234Ala together with Leu235Ala) and thus have diminished effector function. Such antibodies may have the designation of G1AA for having the LALA double mutation on IgG1.

Other recombinant human IgG antibodies (hIgGs) partially or completely devoid of binding to Fcγ receptors (FcγRs) and complement protein C1q, and thus with abolished immune effector functions, are known in the art, and are of use for various therapeutic applications in order to reduce FcγR activation and Fc-mediated toxicity. Certain such Fc-engineered antibodies/fragments partially achieve this goal, while others completely abolishes FcγR activation and Fc-mediated toxicity. In certain embodiments, the antibody/fragment of the invention has an engineered hIgG Fc domain comprising hIgG1-P329G LALA or hIgG4-P329G SPLE (the human IgG4 S228P/L235E variant of IgG4) mutations, with completely abolish FcγR and C1q interactions, and with unaffected FcRn interactions and Fc stability. The P329G Fc mutation disrupts the formation of a proline sandwich motif with the FcγRs. As this motif is present in the interface of all IgG Fc/FcγR complexes, its disruption can be applied to all human and most of the other mammalian IgG subclasses to create effector silent IgG molecules. Thus in certain embodiments, the subject antibody/fragment has any one IgG subclass with such effector silent Fc mutation.

In certain embodiments, the monoclonal antibody or antigen-binding fragment thereof cross-reacts with mouse Gal9.

In certain embodiments, the monoclonal antibody or antigen-binding fragment thereof binds to human Gal9 with an EC50 of about 0.1-0.2 nM, and/or binds to mouse Gal9 with an EC50 of about 0.5-1.0 nM.

In certain embodiments, the d monoclonal antibody or antigen-binding fragment thereof binds human Gal9 with a Kd of less than about 25 nM, 20 nM, 15 nM, 10 nM, 5 nM, 2 nM, or 1 nM.

In certain embodiments, the monoclonal antibody or antigen-binding fragment thereof of the invention includes one or more point mutations of its amino acid sequence that are designed to improve developability of the antibody. For example, in certain embodiments, the one or more point mutations make the antibody more stable during its expression in a host cell, its purification during the manufacturing, and/or the formulation processes, and/or its administration to a subject patient. In certain embodiments, the one or more point mutations make the antibody less likely to aggregate during the manufacturing and/or formulation processes.

In certain embodiments, the invention provides a therapeutic antibody with minimized or reduced developability issues, such as removed or reduced hydrophobicity and/or optimized charges by replacing one or more amino acids in its sequence (e.g., in one or more of its CDRs).

In certain embodiments, the isolated monoclonal antibody or antigen-binding fragment thereof binds to Gal9 and inhibits Gal9 binding to a Gal9 receptor (e.g., TIM3 or CD44).

In certain embodiments, the isolated monoclonal antibody or antigen-binding fragment thereof neutralizes Gal-9-induced Th1 apoptosis of T cells (such as CD4+ T cells).

In certain embodiments, the isolated monoclonal antibody or antigen-binding fragment thereof suppresses Gal9-induced Treg expansion.

In certain embodiments, the isolated monoclonal antibody or antigen-binding fragment thereof synergistically inhibits tumor growth in vivo and/or prolongs survival in a mouse with a xenograph tumor with an antagonist of an immune checkpoint.

In certain embodiments, the antagonist of the immune checkpoint is an antibody or antigen-binding fragment thereof specific for PD-1 or PD-L1.

Another aspect of the invention provides a method of treating cancer in a patient in need thereof, the method comprising administering to the patient an effective amount of the isolated monoclonal antibody or antigen-binding fragment thereof of the invention, and an antagonist of an immune checkpoint.

In certain embodiments, the immune checkpoint is PD-1/PD-L1 immune checkpoint.

In certain embodiments, the antagonist of the immune checkpoint is an antibody or antigen-binding fragment thereof specific for PD-1 or PD-L1.

In certain embodiments, the antibody is an anti-PD-1 antibody, such as cemiplimab, nivolumab, or pembrolizumab.

In certain embodiments, the antibody is an anti-PD-L1 antibody, such as avelumab, durvalumab, atezolizumab, KN035, or CK-301.

In certain embodiments, the antagonist of the immune checkpoint is a (non-antibody) peptide inhibitor of PD-1/PD-L1, such as AUNP12; a small molecule inhibitor of PD-L1 such as CA-170, or a macrocyclic peptide such as BMS-986189.

In certain embodiments, the cancer is a hematological cancer (such as AML and DLBCL), or a solid tumor (such as breast cancer, head and neck cancer, lung cancer, melanoma (including uveal melanoma), colon cancer, renal carcinoma, ovarian cancer, liver cancer, and prostate cancer).

In certain embodiments, the method further comprises administering to the patient a chemotherapeutic agent, an anti-angiogenesis agent, a growth inhibitory agent, an immune-oncology agent, and/or an anti-neoplastic composition.

Another aspect of the invention provides a polynucleotide encoding the heavy chain or the light chain or the antigen-binding portion thereof of the invention.

In certain embodiments, the polynucleotide is codon optimized for expression in a human cell.

Another aspect of the invention provides a vector comprising the polynucleotide of the invention.

In certain embodiments, the vector is an expression vector (e.g., a mammalian expression vector, a yeast expression vector, an insect expression vector, or a bacterial expression vector).

Another aspect of the invention provides a method of promoting, potentiating, restoring or rescuing effector T cells proliferation, and/or enhancing effector T cell activity in a patient diagnosed with cancer, in risk of developing cancer or having cancer relapse, or a method of identifying and treating a patient having cancer, the method comprising: administering to the patient an effective amount of the isolated monoclonal antibody or antigen-binding fragment thereof of the invention, upon identifying the patient as having a level of Galectin-9 in a sample from the patient higher than a reference level of Galectin-9 in a healthy or a control individual.

In certain embodiments, the method further comprises identifying the patient as having the level of Galectin-9 in the sample higher than the reference level, by comparing the level of Galectin-9 in the sample to the reference level.

In certain embodiments, the method further comprises administering to the patient an antagonist of an immune checkpoint.

In certain embodiments, the immune checkpoint is PD-1/PD-L1 immune checkpoint.

In certain embodiments, the antagonist of the immune checkpoint is an antibody or antigen-binding fragment thereof specific for PD-1 or PD-L1.

In certain embodiments, the antibody is an anti-PD-1 antibody, such as cemiplimab, nivolumab, or pembrolizumab.

In certain embodiments, the antibody is an anti-PD-L1 antibody, such as avelumab, durvalumab, atezolizumab, KN035, or CK-301.

In certain embodiments, the antagonist of the immune checkpoint is a (non-antibody) peptide inhibitor of PD-1/PD-L1, such as AUNP12; a small molecule inhibitor of PD-L1 such as CA-170, or a macrocyclic peptide such as BMS-986189.

In certain embodiments, the cancer is a hematological cancer (such as AML and DLBCL), or a solid tumor (such as breast cancer, head and neck cancer, lung cancer, melanoma (including uveal melanoma), colon cancer, renal carcinoma, ovarian cancer, liver cancer, and prostate cancer).

In certain embodiments, the patient is an FAB M0, M1, M4 or M5 AML patient, or wherein the patient is not an FAB M2 or M3 AML patient.

In certain embodiments, the sample is a blood sample, a plasma sample, or a serum sample.

Another aspect of the invention provides a method of rescuing or promoting effector T cells proliferation and/or enhancing effector T cell activity in a patient diagnosed with AML, in risk of developing AML or having AML relapse, or a method of identifying and treating a patient having AML, the method comprising: administering to the patient an effective amount of the isolated monoclonal antibody or antigen-binding fragment thereof of the invention, upon identifying the patient as having a level of Galectin-9-encoding mRNA in a bone-marrow (BM)-derived mononuclear cell (MNC) sample from the patient statistically significantly higher or lower than a reference level in BM-derived MNC or CD34+ cells in a healthy or a control individual.

In certain embodiments, the level of Galectin-9-encoding mRNA in the BM-derived MNC sample from the patient is significantly higher than the reference level when the patient is an FAB M0, M1, M2, M4, or M5 AML patient.

In certain embodiments, the level of Galectin-9-encoding mRNA in the BM-derived MNC sample from the patient is significantly lower than the reference level when the patient is an FAB M3 AML patient.

Another aspect of the invention provides an antibody, or an antigen-binding portion thereof, directed against or specific for Galectin-9, for use in the treatment of cancer, wherein said antibody or antigen-binding portion thereof rescues effector T cell proliferation, and/or enhances effector T cell activity.

In certain embodiments, the effector T cell is a Th1 cell.

Another aspect of the invention provides a method of rescuing or promoting effector T cell proliferation, and/or enhancing effector T cell activity, comprising contacting said effector T cell with the isolated monoclonal antibody or antigen-binding fragment thereof of the invention.

In certain embodiments, the effector T cell is a Th 1 cell.

Another aspect of the invention provides a method and related compositions for inducing or promoting immune memory that results in anti-tumor (anti-cancer) activity. In certain embodiments, the method comprises administering a composition (such as a pharmaceutical composition comprising an antibody of the invention) to a subject in an amount effective in inducing, stimulating or promoting immune memory that effectively reduces or inhibits tumor or cancer initiation, progression or recurrence in the subject.

It should be understood that any one embodiment of the invention described herein, including those described only in the examples or claims, can be combined with any one or more additional embodiment of the invention unless expressly disclaimed or otherwise improper.

BRIEF DESCRIPTION OF THE DRAWINGS

FIG. 5 shows that the various anti-human Galectin-9 humanized antibodies of the invention can block binding to TIM3 and CDC44.

US 12,649,794 B2

9 with anti-PD1 antibodies led to significantly better/syner-gistic therapeutic efficacy as measured by inhibition of tumor volume increase.

Figure 9:
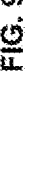
Figure 9:
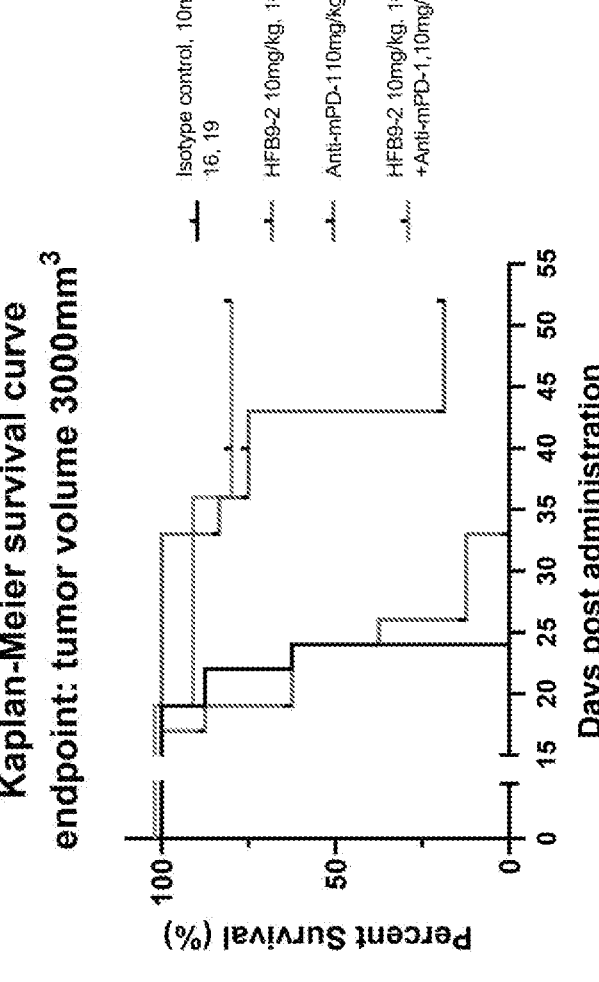

FIG. 9 shows the ability of the various anti-human Galec-tin-9 humanized antibodies of the invention to promote long term survival when used in combination with anti-PD1 antibodies. The data demonstrates that combination therapy with anti-PD1 antibodies led to significantly better/syner-gistic therapeutic efficacy as measured by survival over time.

Figure 10:
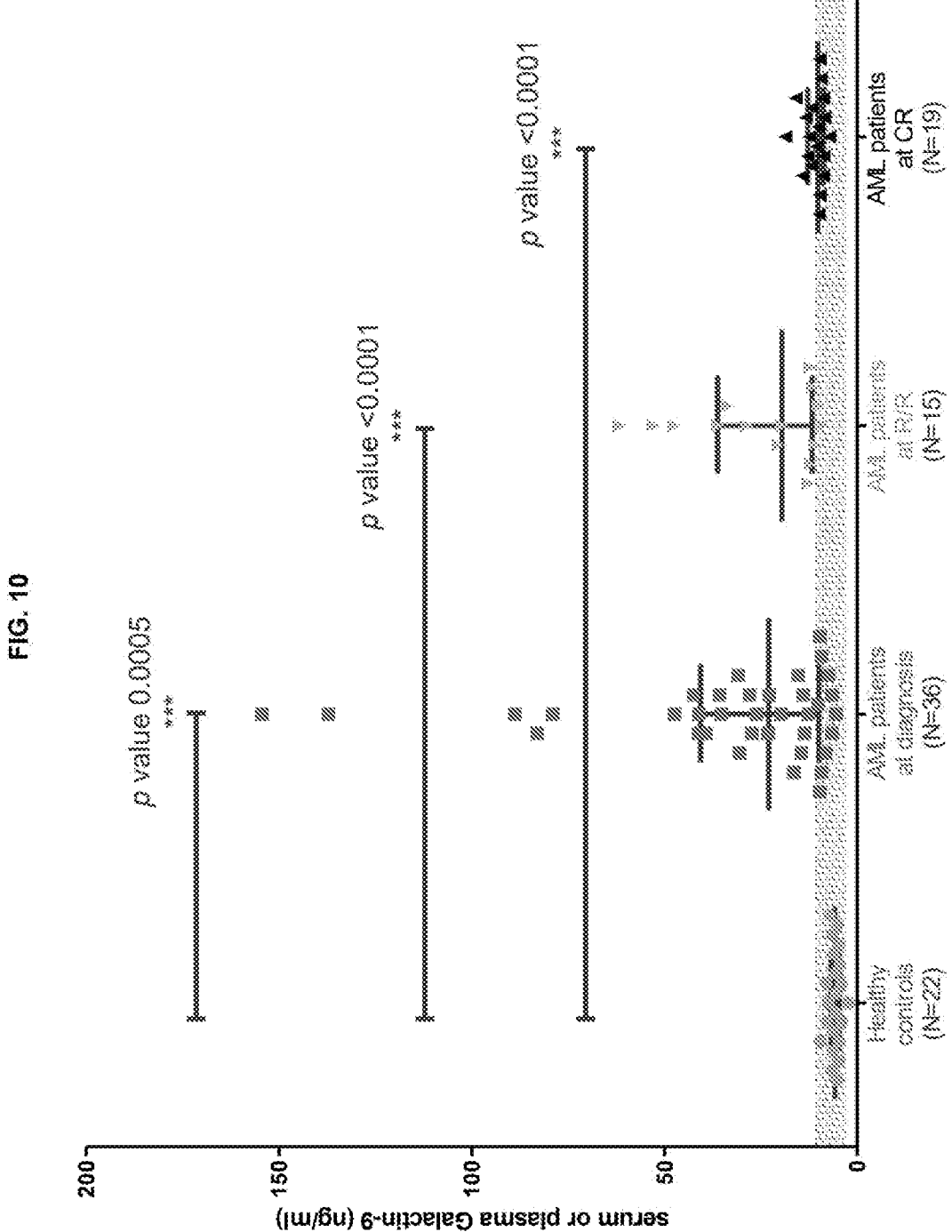

FIG. 10 shows the levels of Galectin-9 in serum or plasma from AML patients and healthy individuals. The data dem-onstrates that Galectin-9 levels in plasma from AML pateints at diagnosis or relapse/refractory (R/R) stages were signifi-cantly higher than in plasma from healthy patients and AML patients at complete remission post chemotherapy treatment.

Figure 11:
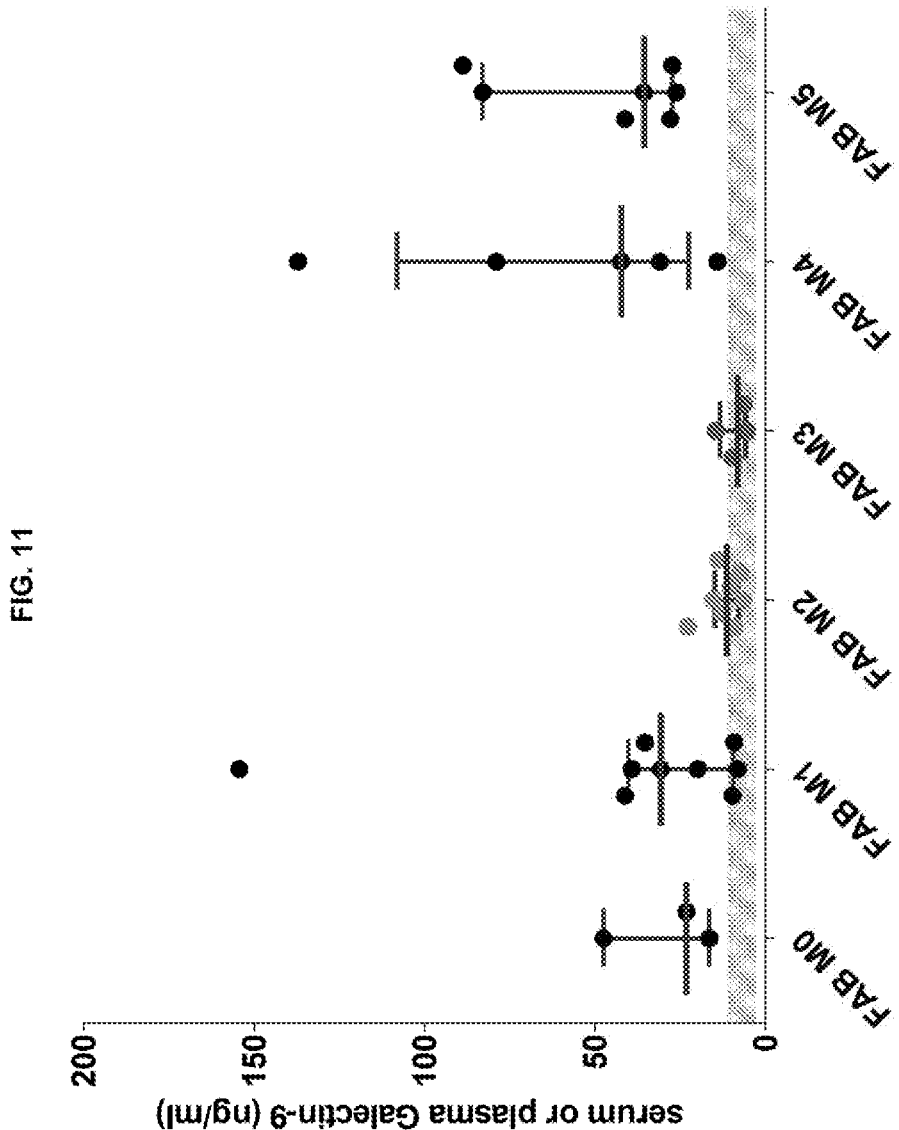

FIG. 11 shows levels of Galectin-9 in plasma or serum from AML patients stratified according to the French-American-British (FAB) classification. The data shows Galectin-9 protein levels in plasma of FAB M2 or FAB M3 AML patients at diagnosis were significantly lower than those observed in plasma from FAB M0, M1, M4 or M5 AML patients. Galectin-9 protein levels in plasma of FAB M3 AML patients at diagnosis were within the normal, physiological range.

Figure 12:
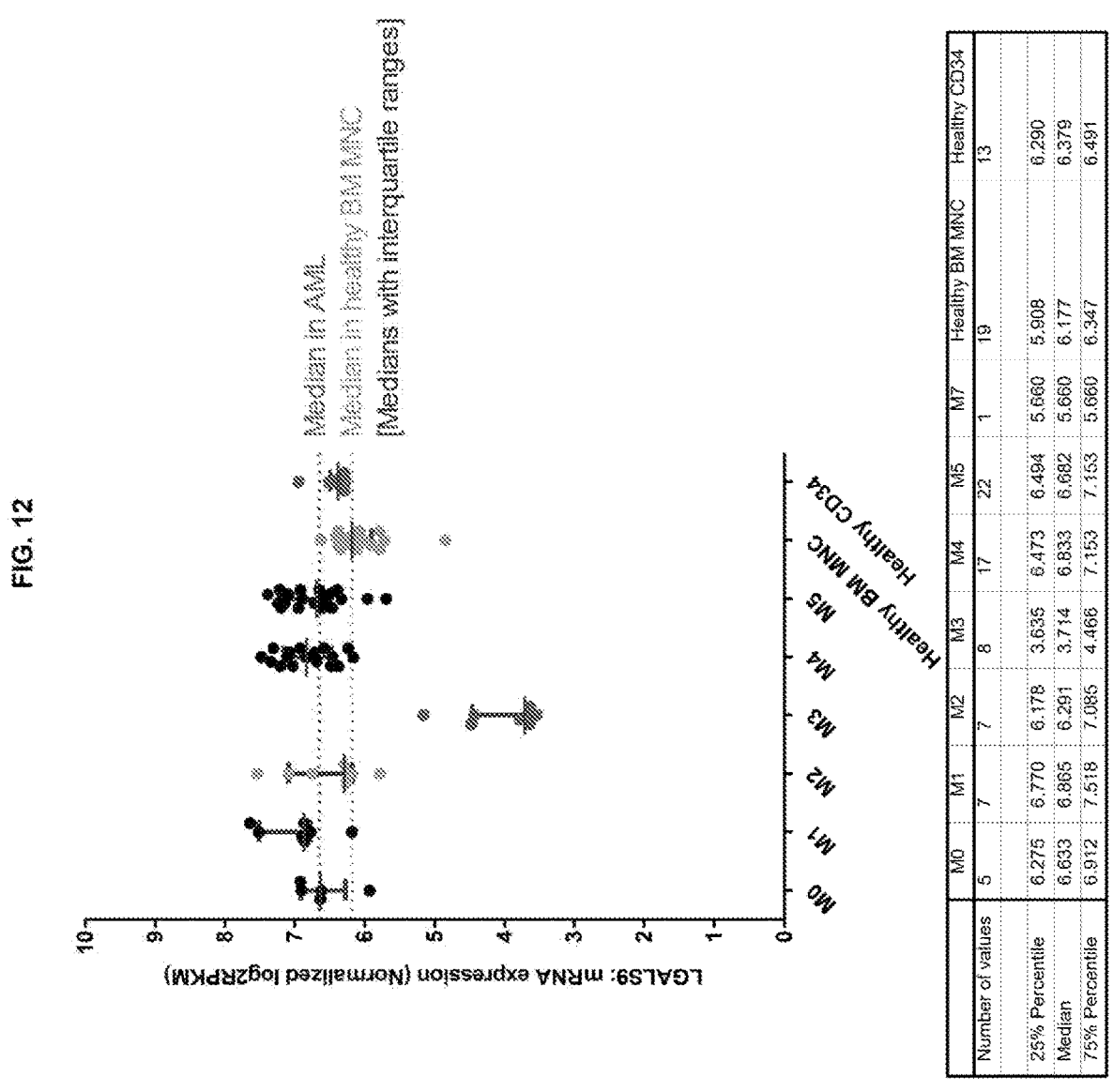

FIG. 12 shows levels of Galactin-9-encoding mRNA (LGALS9) in bone-marrow (BM)-divided mononuclear cells (MNC) from AML patients stratified according to the French-American-British (FAB) classification, or from healthy individuals. The data demonstrates that Galectin-9-encoding mRNA levels in BM-derived MNC from AML patients at diagnosis (all FAB considered) were higher than those observed in BM-derived MNC or CD34$^+$ cells from healthy individuals. Galectin-9-encoding mRNA levels in BM-derived MNC from FAB M3 AML patients at diagnosis were significantly lower than those observed in BM-derived MNC from FAB M0, M1, M4 or M5 AML patients or from BM-derived MNC or CD34 cells from healthy individuals.

Figure 13:
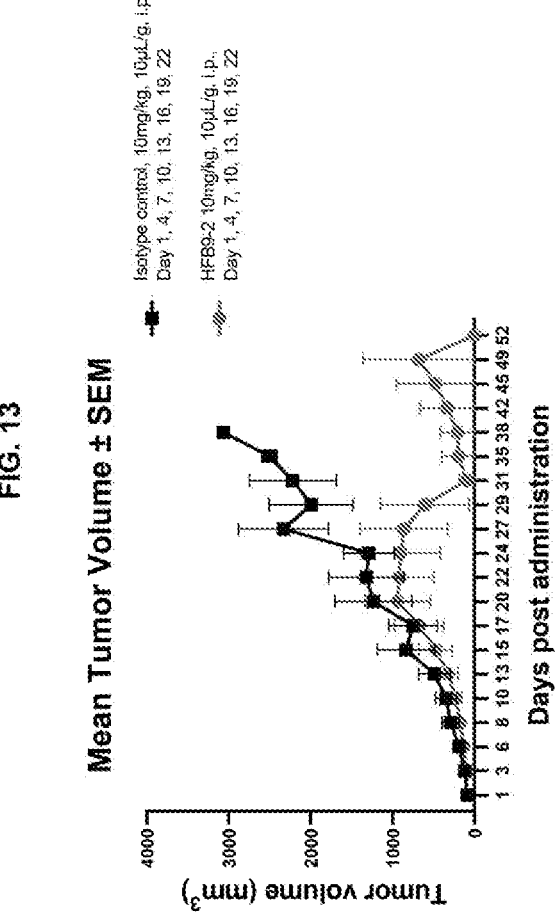

FIG. 13 shows anti-tumor activity of an antibody of the invention as a monotherapy. This experiment demonstrates that the anti-Gal9 monoclonal antibodies of the invention are effective in inhibiting tumor growth in vivo in a xenograph mouse model. In particular, about half million cancer cells were inoculated into experimental mice and the tumor mass was allowed to grow to a pre-determined size. Mice were then randomized and injected intraperitoneally (i.p.) with one of two antibodies: (1) IgG isotype control at a dose of 10 mg/kg, (2) anti-Gal9 antibody HFB9-2 at a dose of 10 mg/kg. The first dose of the antibodies for the various groups were administered on Day 1, and subsequent doses were administered every 3 days, for eight doses in total for any groups with anti-HFB9-2 antibody and the control antibody. Data are presented as mean±s.e.m. (n=10 mice per group). It is apparent that the subject anti-Gal9 antibody exhibited inhibitory effect on tumor growth in vivo.

Figure 14:
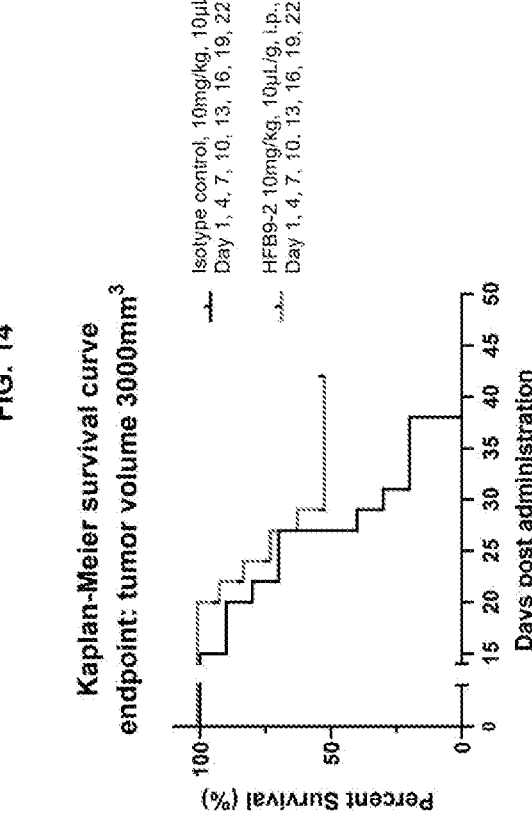

FIG. 14 further shows anti-tumor activity of an antibody of the invention as a monotherapy in terms of survival: all mice in the control group died, and 40% of the mice (4 out of 10) in the HFB9-2 treatment group survived tumor-free at the end of week 6.

Figure 15:
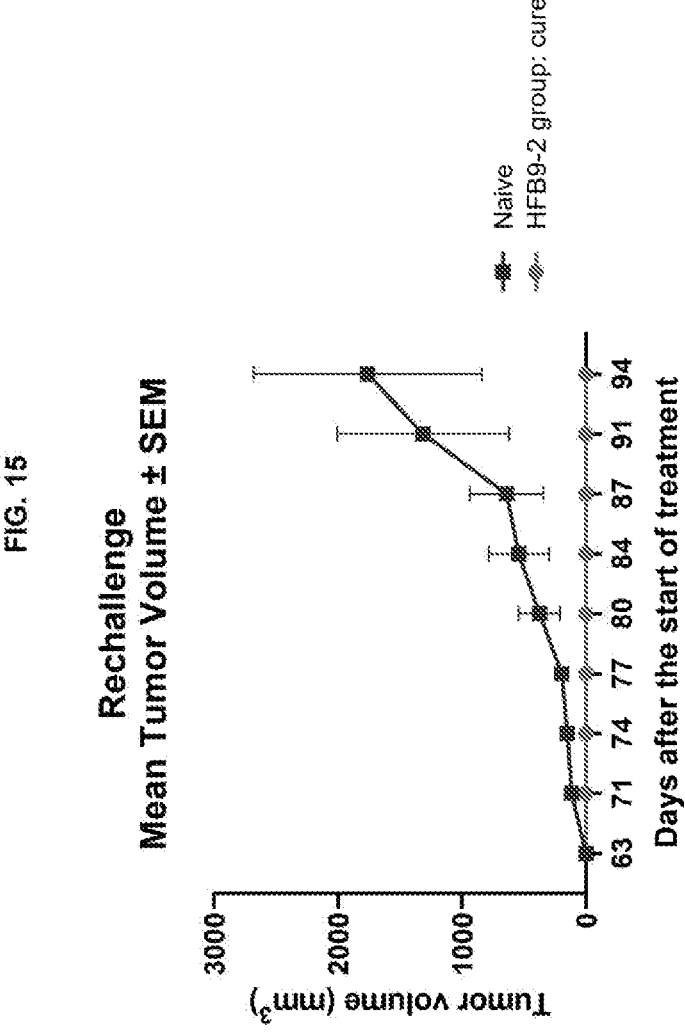

FIG. 15 shows immune memory of the anti-tumor activity of an antibody of the invention. After the first tumor inocu-lation/challenge, naïve animals developed tumors with 2 out of the 4 animals reaching tumor volume of 3000 mm$^3$ humane endpoint in 31 days. Four animals with complete tumor regression, previously treated and cured by HFB9-2, an antibody of the invention, completely rejected a second Wehi-164 tumor challenge inoculated 63 days after the first tumor challenge. These data suggest long-term immune memories induced by HFB9-2 treatment.

DETAILED DESCRIPTION OF THE INVENTION

1. Overview

Although monoclonal antibodies targeting immune checkpoints have demonstrated clinical success in a range of tumor types, sustained responses are only observed in a fraction of patients due to primary or secondary resistance to treatment.

Applicant believes Galectin 9 (Gal-9) is a key factor present in the tumor microenvironment that renders tumors resistant to current immunotherapies. Among other evi-dence, high Gal-9 expression has been reported in different types of cancers, including hematological malignancies such as AML and ALL, and multiple solid tumors.

The invention described herein provides antibodies tar-geting Gal-9 that overcome resistance and improve clinical response in at least a subset of cancer patients. The mono-clonal antibodies of the invention specifically binds to human Gal-9 with sub-nanomolar affinity, recognizes recombinant Gal-9 and Gal-9 produced by human tumor cells, and is cross-reactive with mouse and monkey Gal-9 orthologs. They also block the interaction of Gal-9 with its receptors TIM3 and CD44 in a dose dependent manner. These two receptors have been described to mediate Gal-9-immunosuppressive signals in effector and regulatory T cells. Treatment of human PBMCs from healthy donors with the antibodies of the invention prevents Gal-9-induced Th1 cell apoptosis and suppresses the expansion of regulatory T cells.

Certain humanized version of the antibodies of the inven-tion exhibit further favorable characteristics in terms of stability and pharmacokinetic (PK) profile, and are thus uniquely suitable for further development as a therapeutic antibody. Specifically, such humanized antibodies showed stability for at least 14 days at 40° C., as well as for several hours at low pH, and following several freeze-thaw cycles. Meanwhile, high plasma exposures following a single dose administration of 10 mg/kg to C57BL/6 mice were observed for the humanized antibody.

The antibodies of the invention can be used to treat a number of cancers, such as AML. Gal-9 has been reported to play a dual role in AML, as both a self-renewal factor for leukemic stem cells, and a suppressor of anti-cancer immu-nity. Thus, antagonizing Gal-9 function by using the Gal-9 neutralizing antibodies of the invention represents an attrac-tive therapeutic approach for treating AML.

Collectively, the data presented herein demonstrates that neutralization of Gal-9 with the antibody of the invention blocks key immunosuppressive mechanisms known to limit the efficacy of current immunotherapies.

Detailed aspects of the invention are described further and separately in the various sections below. However, it should be understood that any one embodiment of the invention, including embodiments described only in the examples or drawings, and embodiments described only under one sec-tion below, can be combined with any other embodiment(s) of the invention.

2. Definitions

The term "antibody," in the broadest sense, encompasses various antibody structures, including but not limited to monoclonal antibodies, polyclonal antibodies, and multispe-
cific antibodies (e.g., bispecific antibodies). The term "anti-
body" may also broadly refers to a molecule comprising
complementarity determining region (CDR) 1, CDR2, and
CDR3 of a heavy chain and CDR1, CDR2, and CDR3 of a
light chain, wherein the molecule is capable of binding to an
antigen. The term "antibody" also includes, but is not limited
to, chimeric antibodies, humanized antibodies, human anti-
bodies, and antibodies of various species such as mouse,
human, cynomolgus monkey, etc.

In a narrower sense, however, "antibody" refers to the
various monoclonal antibodies, including chimeric mono-
clonal antibodies, humanized monoclonal antibodies, and
human monoclonal antibodies, particularly humanized
monoclonal antibodies of the invention.

In some embodiments, an antibody comprises a heavy
chain variable region (HCVR) and a light chain variable
region (LCVR). In some embodiments, an antibody com-
prises at least one heavy chain (HC) comprising a heavy
chain variable region and at least a portion of a heavy chain
constant region, and at least one light chain (LC) comprising
a light chain variable region and at least a portion of a light
chain constant region. In some embodiments, an antibody
comprises two heavy chains, wherein each heavy chain
comprises a heavy chain variable region and at least a
portion of a heavy chain constant region, and two light
chains, wherein each light chain comprises a light chain
variable region and at least a portion of a light chain constant
region.

As used herein, a single-chain Fv (scFv), or any other
antibody that comprises, for example, a single polypeptide
chain comprising all six CDRs (three heavy chain CDRs and
three light chain CDRs) is considered to have a heavy chain
and a light chain. In some such embodiments, the heavy
chain is the region of the antibody that comprises the three
heavy chain CDRs and the light chain in the region of the
antibody that comprises the three light chain CDRs.

The term "heavy chain variable region (HCVR)" as used
herein refers to, at a minimum, a region comprising heavy
chain CDR1 (CDR-H1), framework 2 (HFR2), CDR2
(CDR-H2), FR3 (HFR3), and CDR3 (CDR-H3). In some
embodiments, a heavy chain variable region also comprises
at least a portion (e.g., the whole) of an FR1 (HFR1), which
is N-terminal to CDR-H1, and/or at least a portion (e.g., the
whole) of an FR4 (HFR4), which is C-terminal to CDR-H3.

The term "heavy chain constant region" as used herein
refers to a region comprising at least three heavy chain
constant domains, CH1, CH2, and CH3. Non-limiting exem-
plary heavy chain constant regions include $\gamma$, $\delta$, and $\alpha$.
Non-limiting exemplary heavy chain constant regions also
include $\epsilon$ and $\mu$. Each heavy constant region corresponds to
an antibody isotype. For example, an antibody comprising a
$\gamma$ constant region is an IgG antibody, an antibody comprising
a $\delta$ constant region is an IgD antibody, an antibody com-
prising an a constant region is an IgA antibody, an antibody
comprising an $\epsilon$ constant region is an IgE antibody, and an
antibody comprising an $\mu$ constant region is an IgM anti-
body.

Certain isotypes can be further subdivided into sub-
classes. For example, IgG antibodies include, but are not
limited to, IgG1 (comprising a $\gamma$1 constant region), IgG2
(comprising a $\gamma$2 constant region), IgG3 (comprising a $\gamma$3
constant region), and IgG4 (comprising a $\gamma$4 constant region)
antibodies; IgA antibodies include, but are not limited to,
IgA1 (comprising an al constant region) and IgA2 (com-
prising an $\alpha$2 constant region) antibodies; and IgM antibodies include, but are not limited to, IgM1 (comprising an $\mu$1
constant region) and IgM2 (comprising an $\mu$2 constant
region).

The term "heavy chain" as used herein refers to a poly-
peptide comprising at least a heavy chain variable region,
with or without a leader sequence. In some embodiments, a
heavy chain comprises at least a portion of a heavy chain
constant region. The term "full-length heavy chain" as used
herein refers to a polypeptide comprising a heavy chain
variable region and a heavy chain constant region, with or
without a leader sequence, and with or without a C-terminal
lysine.

The term "light chain variable region (LCVR)" as used
herein refers to a region comprising light chain CDR1
(CDR-L1), framework (FR)2 (LFR2), CDR2 (CDR-L2),
FR3 (LFR3), and CDR3 (CDR-L3). In some embodiments,
a light chain variable region also comprises at least a portion
(e.g., the whole) of an FR1 (LFR1) and/or at least a portion
(e.g., the whole) of an FR4 (LFR4).

The term "light chain constant region" as used herein
refers to a region comprising a light chain constant domain,
$C_L$. Non-limiting exemplary light chain constant regions
include $\lambda$ and $\kappa$.

The term "light chain" as used herein refers to a poly-
peptide comprising at least a light chain variable region,
with or without a leader sequence. In some embodiments, a
light chain comprises at least a portion of a light chain
constant region. The term "full-length light chain" as used
herein refers to a polypeptide comprising a light chain
variable region and a light chain constant region, with or
without a leader sequence.

The term "antibody fragment" or "antigen binding por-
tion" (of antibody) includes, but is not limited to, fragments
that are capable of binding antigen, such as Fv, single-chain
Fv (scFv), Fab, Fab', and (Fab')$_2$. In certain embodiments, an
antibody fragment includes Fab, Fab', F(ab')$_2$, Fa, single
chain Fv or scFv, disulfide linked Fv, V-NAR domain, IgNar,
intrabody, IgG$\Delta$CH$_2$, minibody, F(ab')$_3$, tetrabody, triabody,
diabody, single-domain antibody, DVD-Ig, Fcab, mAb$_2$,
(scFv)$_2$, or scFv-Fc.

The term "Fab" refers to an antibody fragment with a
molecular mass of approximately 50,000 daltons, and has an
activity of binding to the antigen. It comprises approxi-
mately half of the N-terminal side of the heavy chain and the
whole of the light chain connected by a disulphide bridge.
The Fab can be obtained in particular by treatment of
immunoglobulin by a protease, papain.

The term "F(ab')$_2$" designates a fragment of approxi-
mately 100,000 daltons and an activity of binding to the
antigen. This fragment is slightly larger than two Fab
fragments connected via a disulphide bridge in the hinge
region. These fragments are obtained by treating an immu-
noglobulin with a protease, pepsin. The Fab fragment can be
obtained from the F(ab')2 fragment by cleaving of the
disulphide bridge of the hinge region.

A single Fv chain "scFv" corresponds to a VH: VL
polypeptide synthesised using the genes coding for the VL
and VH domains and a sequence coding for a peptide
intended to bind these domains. An scFv according to the
invention includes the CDRs maintained in an appropriate
conformation, for example using genetic recombination
techniques.

The dimers of "scFv" correspond to two scFv molecules
connected together by a peptide bond. This Fv chain is
frequently the result of the expression of a fusion gene
including the genes coding for VH and VL connected by a
linker sequence coding a peptide. The human scFv fragment may include CDR regions that are maintained in an appropriate conformation, preferably by means of the use of genetic recombination techniques.

The "dsFv" fragment is a VH-VL heterodimer stabilised by a disulphide bridge; it may be divalent (dsFV$_2$). Fragments of divalent Sc(Fv)$_2$ or multivalent antibodies may form spontaneously by the association of monovalent scFvs or be produced by connecting scFvs fragments by peptide binding sequences.

The Fc fragment is the support for the biological properties of the antibody, in particular its ability to be recognised by immunity effectors or to activate the complement. It consists of constant fragments of the heavy chains beyond the hinge region.

The term "diabodies" signifies small antibody fragments having two antigen fixing sites. These fragments comprise, in the same VH-VL polypeptide chain, a variable heavy chain domain VH connected to a variable light chain domain VL. Using a binding sequence that is too short to allow the matching of two domains of the same chain, the matching with two complementary domains of another chain necessarily occurs and thus two antigen fixing sites are created.

An "antibody that binds to the same epitope" as a reference antibody can be determined by an antibody competition assay. It refers to an antibody that blocks binding of the reference antibody to its antigen in a competition assay by 50% or more, and conversely, the reference antibody blocks binding of the antibody to its antigen in a competition assay by 50% or more. The term "compete" when used in the context of an antibody that compete for the same epitope means competition between antibodies is determined by an assay in which an antibody being tested prevents or inhibits specific binding of a reference antibody to a common antigen.

Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619); solid phase direct labeled assay; solid phase direct labeled sandwich assay (see, e.g., Harlow and Lane, 1988, Antibodies, A Laboratory Manual, Cold Spring Harbor Press); solid phase direct label RIA using I$^{125}$ label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol.).

Typically, such an assay involves the use of purified antigen bound to a solid surface or cells bearing either of these, an unlabeled test antigen binding protein and a labeled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibodies and antibodies binding to an adjacent epitope sufficiently proximal to the epitope bound by the reference antibody for steric hindrance to occur. In some embodiments, when a competing antibody is present in excess, it will inhibit specific binding of a reference antibody to a common antigen by at least 40%, 45%, 50%, 55%, 60%, 65%, 70% or 75%. In some instance, binding is inhibited by at least 80%, 85%, 90%, 95%, or 97% or more.

The term "antigen" refers to a molecule or a portion of a molecule capable of being bound by a selective binding agent, such as an antibody or immunologically functional fragment thereof, and additionally capable of being used in a mammal to produce antibodies capable of binding to that antigen. An antigen may possess one or more epitopes that are capable of interacting with antibodies.

The term "epitope" is the portion of an antigen molecule that is bound by a selective binding agent, such as an antibody or a fragment thereof. The term includes any determinant capable of specifically binding to an antibody. An epitope can be contiguous or non-contiguous (e.g., in a polypeptide, amino acid residues that are not contiguous to one another in the polypeptide sequence but that within in context of the molecule are bound by the antigen binding protein). In some embodiments, epitopes may be mimetic in that they comprise a three dimensional structure that is similar to an epitope used to generate the antibody, yet comprise none or only some of the amino acid residues found in that epitope used to generate the antibody. Epitope determinants may include chemically active surface groupings of molecules such as amino acids, sugar side chains, phosphoryl or sulfonyl groups, and may have specific three dimensional structural characteristics, and/or specific charge characteristics.

In some embodiments, an "epitope" is defined by the method used to determine it. For example, in some embodiments, an antibody binds to the same epitope as a reference antibody, if they bind to the same region of the antigen, as determined by hydrogen-deuterium exchange (HDX).

For example, the epitope sequence of the parent antibodies HFB9-1 and HFB9-2 is disclosed as SEQ ID NO: 9 in US 2017-0283499 A1 (incorporated herein by reference). This sequence corresponds to the P4 peptide and covers the end of the binding peptide and the start of the C-terminal part of Galectin-9. It exists in the three isoforms of Galectin-9 (e.g., amino acids 166 to 178 of the S isoform, amino acids 178 to 190 of the M isoform, amino acids 210 to 222 of the L isoform). The humanized antibodies of the invention can bind at least one, preferably all the isoforms of Galectin-9.

In certain embodiments, an antibody binds to the same epitope as a reference antibody if they bind to the same region of the antigen, as determined by X-ray crystallography.

A "chimeric antibody" as used herein refers to an antibody comprising at least one variable region from a first species (such as mouse, rat, cynomolgus monkey, etc.) and at least one constant region from a second species (such as human, cynomolgus monkey, chicken, etc.). In some embodiments, a chimeric antibody comprises at least one mouse variable region and at least one human constant region. In some embodiments, all of the variable regions of a chimeric antibody are from a first species and all of the constant regions of the chimeric antibody are from a second species.

A "humanized antibody" as used herein refers to an antibody in which at least one amino acid in a framework region of a non-human variable region (such as mouse, rat, cynomolgus monkey, chicken, etc.) has been replaced with the corresponding amino acid from a human variable region. In some embodiments, a humanized antibody comprises at least one human constant region or fragment thereof. In some embodiments, a humanized antibody fragment is an Fab, an scFv, a (Fab')$_2$, etc.

A "CDR-grafted antibody" as used herein refers to a humanized antibody in which one or more complementarity determining regions (CDRs) of a first (non-human) species have been grafted onto the framework regions (FRs) of a second (human) species.

A "human antibody" as used herein refers to antibodies produced in humans, antibodies produced in non-human animals that comprise human immunoglobulin genes, such as XENOMOUSE*, and antibodies selected using in vitro methods, such as phage display, wherein the antibody repertoire is based on a human immunoglobulin sequences.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Non-limiting exemplary mammalian cells include, but are not limited to, NSO cells, PER.C6® cells (Crucell), and 293 and CHO cells, and their derivatives, such as 293-6E and DG44 cells, respectively.

The term "isolated" as used herein refers to a molecule that has been separated from at least some of the components with which it is typically found in nature or has been separated from at least some of the components with which it is typically produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The terms "subject" and "patient" are used interchangeably herein to refer to a mammal such as human. In some embodiments, methods of treating other non-human mammals, including, but not limited to, rodents, simians, felines, canines, equines, bovines, porcines, ovines, caprines, mammalian laboratory animals, mammalian farm animals, mammalian sport animals, and mammalian pets, are also provided. In some instances, a "subject" or "patient" refers to a (human) subject or patient in need of treatment for a disease or disorder.

The term "sample" or "patient sample" as used herein, refers to material that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized.

By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as sputum, cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

A "reference sample," "reference cell," or "reference tissue," as used herein, refers to a sample, cell or tissue obtained from a source known, or believed, not to be afflicted with the disease or condition for which a method or composition of the invention is being used to identify. In one embodiment, a reference sample, reference cell or reference tissue is obtained from a healthy part of the body of the same subject or patient in whom a disease or condition is being identified using a composition or method of the invention. In one embodiment, a reference sample, reference cell or reference tissue is obtained from a healthy part of the body of at least one individual who is not the subject or patient in whom a disease or condition is being identified using a composition or method of the invention. In some embodiments, a reference sample, reference cell or reference tissue was previously obtained from a patient prior to developing a disease or condition or at an earlier stage of the disease or condition.

A "disorder" or "disease" is any condition that would benefit from treatment with one or more Gal-9 antagonists of the invention. This includes chronic and acute disorders or diseases including those pathological conditions that predispose the mammal to the disorder in question. Non-limiting examples of disorders to be treated herein include cancers.

An "illness associated with the suppressor activity of regulatory T lymphocytes" means any illness (not autoimmune) in which the suppressor activity of regulatory T lymphocytes plays a role, in particular by promoting the development or persistence of the illness. In particular, it has been demonstrated that the suppressor activity of regulatory T lymphocytes promotes the development of tumors. The invention therefore aims more particularly at cancers in which the suppressor activity of T lymphocytes plays a role.

The term "cancer" is used herein to refer to a group of cells that exhibit abnormally high levels of proliferation and growth. A cancer may be benign (also referred to as a benign tumor), pre-malignant, or malignant. Cancer cells may be solid cancer cells (i.e., forming solid tumors) or leukemic cancer cells. The term "cancer growth" is used herein to refer to proliferation or growth by a cell or cells that comprise a cancer that leads to a corresponding increase in the size or extent of the cancer.

Examples of cancer include but are not limited to, carcinoma, lymphoma, blastoma, sarcoma, and leukemia. More particular nonlimiting examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer.

The French-American-British (FAB) classification of acute myeloid leukemia (ALM) categorizes ALM into different stages of the disease. FAB subtypes are shown in Table 1.

TABLE 1

| FAB Classification | |
| --- | --- |
| FAB Subtype | Description |
| M0 | Undifferentiated acute myeloblastic leukemia |
| M1 | Acute myeloblastic leukemia with minimal maturation |
| M2 | Acute myeloblastic leukemia with maturation |
| M3 | Acute promyelocytic leukemia (APL) |
| M4 | Acute myelomoncytic leukemia |
| M5 | Acute monocytic leukemia |
| M6 | Acute erythroblastic leukemia |
| M7 | Acure megakaryoblastic leukemia |

In certain embodiments, cancer as used herein includes a hematological cancer (such as AML and DLBCL), or a solid tumor (such as breast cancer, head and neck cancer, lung cancer, melanoma (including uveal melanoma), colon cancer, renal carcinoma, ovarian cancer, liver cancer, and prostate cancer).

A "chemotherapeutic agent" is a chemical compound that can be useful in the treatment of cancer. Examples of chemotherapeutic agents include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem Intl. Ed. Engl. 33:183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; antiadrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Illinois), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above.

Further non-limiting exemplary chemotherapeutic agents include anti-hormonal agents that act to regulate or inhibit hormone action on cancers such as anti-estrogens and selective estrogen receptor modulators (SERMs), including, for example, tamoxifen (including NOLVADEX® tamoxifen), raloxifene, droloxifene, 4-hydroxy tamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4 (5)-imidazoles, aminoglutethimide, MEGASE megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LUR- TOTECAN® topoisomerase 1 inhibitor; ABARELIX® rmRH; and pharmaceutically acceptable salts, acids or derivatives of any of the above.

An "anti-angiogenesis agent" or "angiogenesis inhibitor" refers to a small molecular weight substance, a polynucle-otide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascu-lar permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent, e.g., antibodies to VEGF-A (e.g., bevaci-zumab (AVASTIN®)) or to the VEGF-A receptor (e.g., KDR receptor or Flt-1 receptor), anti-PDGFR inhibitors such as GLEEVEC® (Imatinib Mesylate), small molecules that block VEGF receptor signaling (e.g., PTK787/ZK2284, SU6668, SUTENTR/SU1 1248 (sunitinib malate), AMG706, or those described in, e.g., international patent application WO 2004/113304). Anti-angiogenesis agents also include native angiogenesis inhibitors, e.g., angiostatin, endostatin, etc. See, e.g., Klagsbrun and D'Amore (1991) Annu. Rev. Physiol. 53:217-39; Streit and Detmar (2003) Oncogene 22:3172-3179 (e.g., Table 3 listing anti-angio-genic therapy in malignant melanoma); Ferrara & Alitalo (1999) Nature Medicine 5 (12): 1359-1364; Tonini et al. (2003) Oncogene 22:6549-6556 (e.g., Table 2 listing known anti-angiogenic factors); and, Sato (2003) Int. J. Clin. Oncol. 8:200-206 (e.g., Table 1 listing anti-angiogenic agents used in clinical trials).

A "growth inhibitory agent" as used herein refers to a compound or composition that inhibits growth of a cell (such as a cell expressing VEGF) either in vitro or in vivo. Thus, the growth inhibitory agent may be one that signifi-cantly reduces the percentage of cells (such as a cell express-ing VEGF) in S phase. Examples of growth inhibitory agents include, but are not limited to, agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubi-cin, epirubicin, daunorubicin, etoposide, and bleomycin. Those agents that arrest G1 also spill over into S-phase arrest, for example, DNA alkylating agents such as tamox-ifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Pou-lenc Rorer), derived from the European yew, is a semisyn-thetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhi-bition of mitosis in cells.

The term "anti-neoplastic composition" refers to a com-position useful in treating cancer comprising at least one active therapeutic agent. Examples of therapeutic agents include, but are not limited to, e.g., chemotherapeutic agents, growth inhibitory agents, cytotoxic agents, agents used in radiation therapy, anti-angiogenesis agents, cancer immunotherapeutic agents (also referred to as immuno-oncology agents), apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (TARCEVA®), platelet derived growth factor inhibitors (e.g., GLEEVEC® (Ima-tinib Mesylate)), a COX-2 inhibitor (e.g., celecoxib), inter-ferons, CTLA4 inhibitors (e.g., anti-CTLA antibody ipilim-umab (YERVOY®)), PD-1 inhibitors (e.g., anti-PD1 antibodies, BMS-936558), PDL1 inhibitors (e.g., anti-PDL1 antibodies, MPDL3280A), PDL2 inhibitors (e.g., anti-PDL2 antibodies), VISTA inhibitors (e.g., anti-VISTA antibodies), cytokines, antagonists (e.g., neutralizing antibodies) that bind to one or more of the following targets ErbB2, ErbB3, ErbB4, PDGFR-beta, BlyS, APRIL, BCMA, PD-1, PDL1, PDL2, CTLA4, VISTA, or VEGF receptor(s), TRAIL/Apo2, and other bioactive and organic chemical agents, etc. Com-binations thereof are also included in the invention.

"Treatment" refers to therapeutic treatment, for example, wherein the object is to slow down (lessen) the targeted pathologic condition or disorder as well as, for example, wherein the object is to inhibit recurrence of the condition or disorder. "Treatment" covers any administration or applica-tion of a therapeutic for a disease (also referred to herein as a "disorder" or a "condition") in a mammal, including a human, and includes inhibiting the disease or progression of the disease, inhibiting or slowing the disease or its progres-sion, arresting its development, partially or fully relieving the disease, partially or fully relieving one or more symp-toms of a disease, or restoring or repairing a lost, missing, or defective function; or stimulating an inefficient process. The term "treatment" also includes reducing the severity of any phenotypic characteristic and/or reducing the incidence, degree, or likelihood of that characteristic. Those in need of treatment include those already with the disorder as well as those at risk of recurrence of the disorder or those in whom a recurrence of the disorder is to be prevented or slowed down.

The term "effective amount" or "therapeutically effective amount" refers to an amount of a drug effective to treat a disease or disorder in a subject. In some embodiments, an effective amount refers to an amount effective, at dosages and for periods of time necessary, to achieve the desired therapeutic or prophylactic result. A therapeutically effective amount of Gal9 antagonist of the invention may vary according to factors such as the disease state, age, sex, and weight of the individual, and the ability of the antagonist to elicit a desired response in the individual. A therapeutically effective amount encompasses an amount in which any toxic or detrimental effects of Gal9 antagonist are outweighed by the therapeutically beneficial effects.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a sub-ject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

An "article of manufacture" is any manufacture (e.g., a package or container) or kit comprising at least one reagent, e.g., a medicament for treatment of a disease or disorder, or a probe for specifically detecting a biomarker described herein. In some embodiments, the manufacture or kit is promoted, distributed, or sold as a unit for performing the methods described herein.

3. Methods of Treating Cancer

The invention described herein provides Gal9 antagonists (such as anti-Gal9 antibody) for use in methods of treating humans and other non-human mammals.

In a pathological situation, Tregs may cause an inappropriate immune suppression, which could, for example, promotes tumor growth. Tregs have been associated with reducing the anti-tumoral immune responses, in particular by inappropriately inhibiting the activity of the effector T lymphocytes, thus promoting the development of numerous cancer types.

During activation, Galectin-9 is directly expressed by the Tregs, while it is only very weakly expressed, or not at all, by the effector T lymphocytes. Thus, targeting Galectin-9 by, for example, using a Gal-9-specific antibody, could specifically inhibit the suppressor activity of the regulatory T lymphocytes without risking causing depletion of effector T lymphocytes. The antibodies according to the invention, directed against Galectin-9 and inhibiting the suppressor activity of regulatory T lymphocytes, can therefore be used in the treatment of disease or conditions associated with the suppressor activity of regulatory T lymphocytes, in particular the treatment of cancers.

In some embodiments, methods for treating or preventing a cancer are provided, comprising administering an effective amount of Gal9 antagonist to a subject in need of such treatment.

In some embodiments, methods of treating cancer are provided, wherein the methods comprise administering Gal9 antagonist to a subject with cancer.

In some embodiments, use of Gal9 antagonist for treating cancer is provided.

The cancers treatable by the method/use of the invention include those in which the regulatory T lymphocytes exert their suppressor activity, such as those cancers in which relatively large amount of the regulatory T lymphocytes are present in the tumoral tissue or in the circulation. Expansion of the regulatory T lymphocytes (which can be measured by frequency of Tregs) is generally correlated with an increase of Tregs activation. The frequency of the regulatory T lymphocytes can be assessed by any method known in the art, for example by a flow cytometry (FACS) analysis of the intra-tumoral lymphocytes or circulating lymphocytes, or by an immuno-histological staining of the tumoral tissue.

Non-limiting exemplary cancers that may be treated with Gal9 antagonists are provided herein, including carcinoma, lymphoma, blastoma, sarcoma, and leukemia. More particular non-limiting examples of such cancers include melanoma, cervical cancer, squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, ovarian cancer, liver cancer, bladder cancer, hepatoma, breast cancer, colon cancer, colorectal cancer, endometrial or uterine carcinoma, salivary gland carcinoma, kidney cancer, renal cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer.

In certain embodiment, the method/use of the invention can be used to treat cancers in which there are known high levels of regulatory T lymphocytes, and/or which cancers/tumors are clearly associated with poor prognosis, including: chronic myeloid leukaemia (CML), colon cancer, melanoma, cancer of the uterus, breast cancer, pancreatic cancer, gastric cancers, ovarian cancer, primary lymphoma of the central nervous system, multiple myelomas, prostate cancer, Hodgkin's lymphoma, or hepatocellular carcinoma.

In certain embodiment, the method/use of the invention can be used to treat cancers that produce large quantities of exosomes carrying Galectin-9 fulfilling an immune suppressor role. Non-limitative examples of such cancers include: viro-induced cancers, for example nasopharyngeal carcinomas associated with the EBV (Epstein-Barr virus) or hepatocellular carcinomas (CHCs) related to the HCV (hepatitis C virus) or HBV (hepatitis B virus).

In some embodiments, the cancer is a hematological cancer (such as AML and DLBCL), or a solid tumor (such as breast cancer, head and neck cancer, lung cancer, melanoma (including uveal melanoma), colon cancer, renal carcinoma, ovarian cancer, liver cancer, and prostate cancer).

In certain embodiment, the method/use of the invention can be used to treat recurrence of fibrosis resulting from hepatitis C, since it has also been demonstrated that increasing the frequency of the regulatory T lymphocytes is a factor predicting recurrence of such fibrosis.

In some embodiments, the Gal9 antagonist is an anti-Gal9 antibody, or simply "Gal9 antibody."

In some embodiments, the Gal9 antagonist for treating cancer may be a non-antibody protein, such as a soluble version of the Gal9 protein or a portion thereof (e.g., the ECD) that inhibits the interaction between Gal9 and its ligand, optionally further comprising a fusion partner and in the form of a fusion molecule. Various exemplary Gal9 antagonists are described in more detail in the sections that follow.

In some embodiments, the Gal9 antagonist of the invention can be used alone, or alternatively used in combination with any other suitable compound known to be able to treat the disease or indication.

Thus according to a particular embodiment of the invention, an antibody directed against Galectin-9 and inhibiting the suppressor activity of regulatory T lymphocytes as previously defined is used in combination with a second therapeutic agent for treating a disease associated with the suppressor activity of regulatory T lymphocytes, for example an anticancer agent.

That is, when the use is the treatment of a cancer, the antibody can be used in combination with known therapies against cancer such as for example surgery, radiotherapy, chemotherapy or combinations thereof. For example, the antibody can be used in combination with an adoptive immunotherapy, consisting one or more injections of effector lymphocytes against tumoral antigens, in particular EBV antigens. According to some aspects, other anticancer agents used in combination with the antibody directed against Galectin-9 according to the invention for cancer therapy comprise anti-angiogenics. According to certain aspects, the antibody can be co-administered with a cytokine, for example a cytokine that stimulates an anti-tumoral immune response.

In such combination therapy, the antibody of the invention can be used before, after, or concurrently with the second therapeutic agent. See further section below concerning combination therapy.

4. Routes of Administration and Carriers

In various embodiments, Gal9 antagonists (e.g., Gal9 Ab) may be administered subcutaneously or intravenously. For simplicity, "Gal9 antagonist" here, in the narrow sense, refers to Gal1 antibody of the invention, e.g. the humanized Gal9 antibody of the invention.

In some embodiments, Gal9 antagonist may be administered in vivo by various routes, including, but not limited to, oral, intra-arterial, parenteral, intranasal, intramuscular, intracardiac, intraventricular, intratracheal, buccal, rectal, intraperitoneal, by inhalation, intradermal, topical, transdermal, and intrathecal, or otherwise, e.g., by implantation.

In some embodiments, Gal9 antagonist is an anti-Gal9 antibody or antigen-binding fragment thereof, and is administered intravenously (i.v.) or subcutaneously (s.c.).

The subject compositions may be formulated into preparations in solid, semi-solid, liquid, or gaseous forms; including, but not limited to, tablets, capsules, powders, granules, ointments, solutions, suppositories, enemas, injections, inhalants, and aerosols.

In various embodiments, compositions comprising Gal9 antagonist are provided in formulations with a wide variety of pharmaceutically acceptable carriers (see, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Nonlimiting exemplary carriers include saline, buffered saline, dextrose, water, glycerol, ethanol, and combinations thereof.

In various embodiments, compositions comprising Gal9 antagonist may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives.

In various embodiments, the compositions may be formulated for inhalation, for example, using pressurized acceptable propellants such as dichlorodifluoromethane, propane, nitrogen, and the like.

The compositions may also be formulated, in various embodiments, into sustained release microcapsules, such as with biodegradable or non-biodegradable polymers. A non-limiting exemplary biodegradable formulation includes poly lactic acid-glycolic acid (PLGA) polymer. A non-limiting exemplary non-biodegradable formulation includes a polyglycerin fatty acid ester. Certain methods of making such formulations are described, for example, in EP 1125584 A1.

Pharmaceutical dosage packs comprising one or more containers, each containing one or more doses of Gal9 antagonist, are also provided. In some embodiments, a unit dosage is provided wherein the unit dosage contains a predetermined amount of a composition comprising Gal9 antagonist, with or without one or more additional agents. In some embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in some embodiments, the composition may be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition of the invention comprises heparin and/or a proteoglycan.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated.

In some embodiments, Gal9 antagonist may be administered in an amount in the range of about 50 μg/kg body weight to about 50 mg/kg body weight per dose. In some embodiments. Gal9 antagonist may be administered in an amount in the range of about 100 μg/kg body weight to about 50 mg/kg body weight per dose. In some embodiments, Gal9 antagonist may be administered in an amount in the range of about 100 μg/kg body weight to about 20 mg/kg body weight per dose. In some embodiments, Gal9 antagonist may be administered in an amount in the range of about 0.5 mg/kg body weight to about 20 mg/kg body weight per dose.

In some embodiments, Gal9 antagonist may be administered in an amount in the range of about 10 mg to about 1,000 mg per dose. In some embodiments, Gal9 antagonist may be administered in an amount in the range of about 20 mg to about 500 mg per dose. In some embodiments, Gal9 antagonist may be administered in an amount in the range of about 20 mg to about 300 mg per dose. In some embodiments, Gal9 antagonist may be administered in an amount in the range of about 20 mg to about 200 mg per dose.

The Gal9 antagonist compositions may be administered as needed to subjects. In some embodiments, an effective dose of Gal9 antagonist is administered to a subject one or more times. In various embodiments, an effective dose of Gal9 antagonist is administered to the subject once a month, less than once a month, such as, for example, every two months, every three months, or every six months. In other embodiments, an effective dose of Gal9 antagonist is administered more than once a month, such as, for example, every two weeks, every week, twice per week, three times per week, daily, or multiple times per day. An effective dose of Gal9 antagonist is administered to the subject at least once. In some embodiments, the effective dose of Gal9 antagonist may be administered multiple times, including for periods of at least a month, at least six months, or at least a year. In some embodiments, Gal9 antagonist is administered to a subject as-needed to alleviate one or more symptoms of a condition.

5. Combination Therapy

Gal9 antagonists of the invention, including any antibodies and functional fragments thereof, may be administered to a subject in need thereof in combination with other biologically active substances or other treatment procedures for the treatment of diseases. For example, Gal9 antagonists may be administered alone or with other modes of treatment. They may be provided before, substantially contemporaneous with, or after other modes of treatment, such as radiation therapy.

For treatment of cancer, the Gal9 antagonist may be administered in conjunction with one or more of anti-cancer agents, such as the immune checkpoint inhibitor, chemotherapeutic agent, growth inhibitory agent, anti-angiogenesis agent or anti-neoplastic composition.

In certain embodiments, Gal9 antagonist specifically binds to Gal9 (a "Gal9-binding antagonist"), e.g., Gal9 antagonist antibody or antigen-binding fragment thereof, is administered with a second antagonist such as an immune checkpoint inhibitor (e.g., an inhibitor of the PD-1 or PD-L1 pathway), to a subject having a disease in which the stimulation of the immune system would be beneficial, e.g., cancer or infectious diseases. The two antagonists may be administered simultaneously or consecutively, e.g., as described below for the combination of Gal9 antagonist with an immuno-oncology agent. One or more additional therapeutics, e.g., checkpoint modulators may be added to a treatment with Gal9 binding antagonist for treating cancer or infectious diseases.

In certain embodiments, Gal9 antagonist is administered with another treatment, either simultaneously, or consecutively, to a subject, e.g., a subject having cancer. For example, Gal9 antagonist may be administered with one of more of: radiotherapy, surgery, or chemotherapy, e.g., targeted chemotherapy or immunotherapy.

Immunotherapy, e.g., cancer immunotherapy includes cancer vaccines and immuno-oncology agents. Gal9 antagonist may be, e.g., a protein, an antibody, antibody fragment or a small molecule, that binds to Gal9. Gal9 antagonist may be an antibody or antigen binding fragment thereof that specifically binds to Gal9.

In certain embodiments, a method of treatment of a subject having cancer comprises administering to the subject having the cancer Gal9 antagonist, e.g., Gal9 antibody, and one or more immuno-oncology agents, such as immune checkpoint inhibitor.

Immunotherapy, e.g., therapy with an immuno-oncology agent, is effective to enhance, stimulate, and/or upregulate immune responses in a subject. In one aspect, the administration of Gal9 antagonist with an immuno-oncology agent (such as a PD-1 inhibitor) has a synergic effect in the treatment of cancer, e.g., in inhibiting tumor growth.

In one aspect, Gal9 antagonist is sequentially administered prior to administration of the immuno-oncology agent. In one aspect, Gal9 antagonist is administered concurrently with the immunology-oncology agent (such as PD-1 inhibitor). In yet one aspect, Gal9 antagonist is sequentially administered after administration of the immuno-oncology agent (such as PD-1 inhibitor). The administration of the two agents may start at times that are, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks apart, or administration of the second agent may start, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks after the first agent has been administered.

In certain aspects, Gal9 antagonist and an immuno-oncology agent (e.g., PD-1 inhibitor) are administered simultaneously, e.g., are infused simultaneously, e.g., over a period of 30 or 60 minutes, to a patient. Gal9 antagonist may be co-formulated with an immuno-oncology agent (such as PD-1 inhibitor).

Immuno-oncology agents include, for example, a small molecule drug, antibody or fragment thereof, or other biologic or small molecule. Examples of biologic immuno-oncology agents include, but are not limited to, antibodies, antibody fragments, vaccines and cytokines. In one aspect, the antibody is a monoclonal antibody. In certain aspects, the monoclonal antibody is humanized or human antibody.

In one aspect, the immuno-oncology agent is (i) an agonist of a stimulatory (including a co-stimulatory) molecule (e.g., receptor or ligand) or (ii) an antagonist of an inhibitory (including a co-inhibitory) molecule (e.g., receptor or ligand) on immune cells, e.g., T cells, both of which result in amplifying antigen-specific T cell responses. In certain aspects, an immuno-oncology agent is (i) an agonist of a stimulatory (including a co-stimulatory) molecule (e.g., receptor or ligand) or (ii) an antagonist of an inhibitory (including a co-inhibitory) molecule (e.g., receptor or ligand) on cells involved in innate immunity, e.g., NK cells, and wherein the immuno-oncology agent enhances innate immunity. Such immuno-oncology agents are often referred to as immune checkpoint regulators, e.g., immune checkpoint inhibitor or immune checkpoint stimulator.

In certain embodiments, the immuno-oncology agent may be an agent that targets (or binds specifically to) a member of the B7 family of membrane-bound ligands, which includes B7-1, B7-2, B7-H1 (PD-L1), B7-DC (PD-L2), B7-H2 (ICOS-L), B7-H3, B7-H4, B7-H5, and B7-H6, or a co-stimulatory or co-inhibitory receptor binding specifically to a B7 family member. An immuno-oncology agent may be an agent that targets a member of the TNF family of membrane bound ligands or a co-stimulatory or co-inhibitory receptor binding specifically thereto, e.g., a TNF receptor family member. Exemplary TNF and TNER family members that may be targeted by immuno-oncology agents include CD40 and CD40L, OX-40, OX-40L, GITR, GITRL, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fnl4, TWEAK, BAFFR, EDAR, XEDAR, TACI, APRIL, BCMA, LTßR, LIGHT, DCR3, HVEM, VEGI/TL1A, TRAMP/DR3, EDAR, EDA1, XEDAR, EDA2, TNFR1, Lymphotoxin α/TNPβ. TNFR2, TNFa, LTßR, Lymphotoxin a 182, FAS, FASL, RELT, DR6, TROY and NGFR. An immuno-oncology agent that may be used in combination with Gal9 antagonist agent for treating cancer may be an agent, e.g., an antibody, targeting a B7 family member, a B7 receptor family member, a TNF family member or a TNFR family member, such as those described above.

In one aspect, Gal9 antagonist is administered with one or more of (i) an antagonist of a protein that inhibits T cell activation (e.g., immune checkpoint inhibitor) such as CTLA-4, PD-1, PD-L1, PD-L2, LAG-3, TIM3, CEACAM-1, BTLA, CD69, Galectin-1, TIGIT, CD113, GPR56, VISTA, B7-H3, B7-H4, 2B4, CD48, GARP, PDIH, LAIR1, TIM-1, TIM-4, and PSGL-1 and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, CD40L, DR3 and CD28H.

In one aspect, an immuno-oncology agent is an agent that inhibits (i.e., an antagonist of) a cytokine that inhibits T cell activation (e.g., IL-6, IL-10, TGF-β, VEGF, and other immunosuppressive cytokines) or is an agonist of a cytokine, such as IL-2, IL-7, IL-12, IL-15, IL-21 and IFNα (e.g., the cytokine itself) that stimulates T cell activation, and stimulates an immune response.

Other agents that can be combined with Gal9 antagonist for stimulating the immune system, e.g., for the treatment of cancer and infectious diseases, include antagonists of inhibitory receptors on NK cells or agonists of activating receptors on NK cells. For example, Anti-Gal9 antagonist can be combined with an antagonist of KIR.

Yet other agents for combination therapies include agents that inhibit or deplete macrophages or monocytes, including but not limited to CSF-IR antagonists such as CSF-IR antagonist antibodies including RG7155 (WO11/70024, WO11/107553, WO11/131407, WO13/87699. WO13/119716, WO13/132044) or FPA008 (WO11/140249; WO13169264; WO14/036357).

Immuno-oncology agents also include agents that inhibit TGF-β signaling.

Additional agents that may be combined with Gal9 antagonist include agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Yet other therapies that may be combined with Gal9 antagonist include therapies that deplete or block Treg cells, e.g., an agent that specifically binds to CD25.

Another therapy that may be combined with Gal9 antagonist is a therapy that inhibits a metabolic enzyme such as indoleamine dioxigenase (IDO), dioxigenase, arginase, or nitric oxide synthetase.

Another class of agents that may be used includes agents that inhibit the formation of adenosine or inhibit the adenosine A2A receptor.

Other therapies that may be combined with Gal9 antagonist for treating cancer include therapies that reverse/prevent T cell anergy or exhaustion and therapies that trigger an innate immune activation and/or inflammation at a tumor site.

Gal9 antagonist may be combined with more than one immuno-oncology agent (such as immune checkpoint inhibitor), and may be, e.g., combined with a combinatorial approach that targets multiple elements of the immune pathway, such as one or more of the following: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/ PD-LJ/PD-L2 pathway and/or depleting or blocking Treg or other immune suppressing cells; a therapy that stimulates positive immune regulation, e.g., with agonists that stimulate the CD-137, OX-40 and/or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); a therapy that inhibits a metabolic enzyme such as indoleamine dioxigenase (IDO), dioxigenase, arginase or nitric oxide synthetase; a therapy that reverses/prevents T cell anergy or exhaustion; a therapy that triggers an innate immune activation and/or inflammation at a tumor site; administration of immune stimulatory cytokines or blocking of immuno repressive cytokines.

For example, Gal9 antagonist can be used with one or more agonistic agents that ligate positive costimulatory receptors; one or more antagonists (blocking agents) that attenuate signaling through inhibitory receptors, such as antagonists that overcome distinct immune suppressive pathways within the tumor microenvironment (e.g., block PD-L1/PD-1/PD-L2 interactions); one or more agents that increase systemically the frequency of anti-tumor immune cells, such as T cells, deplete or inhibit Tregs (e.g., by inhibiting CD25); one or more agents that inhibit metabolic enzymes such as IDO; one or more agents that reverse/ prevent T cell anergy or exhaustion; and one or more agents that trigger innate immune activation and/or inflammation at tumor sites.

In one embodiment, a subject having a disease that may benefit from stimulation of the immune system, e.g., cancer or an infectious disease, is treated by administration to the subject of Gal9 antagonist and an immuno-oncology agent, wherein the immuno-oncology agent is a CTLA-4 antagonist, such as an antagonistic CTLA-4 antibody. Suitable CTLA-4 antibodies include, for example, YERVOY (ipilimumab) or tremelimumab.

In one embodiment, a subject having a disease that may benefit from stimulation of the immune system, e.g., cancer or an infectious disease, is treated by administration to the subject of Gal9 antagonist and an immuno-oncology agent, wherein the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011). Another approach to target the PD-1 receptor is the recombinant protein composed of the extracellular domain of PD-L2 (B7-DC) fused to the Fc portion of IgG1, called AMP-224.

In one embodiment, a subject having a disease that may benefit from stimulation of the immune system, e.g., cancer or an infectious disease, is treated by administration to the subject of Gal9 antagonist and an immuno-oncology agent, wherein the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), MSB0010718C (WO2013/79174) or rHigM12B7.

In one embodiment, a subject having a disease that may benefit from stimulation of the immune system, e.g., cancer or an infectious disease, is treated by administration to the subject of Gal9 antagonist and an immuno-oncology agent, wherein the immuno-oncology agent is a LAG-3 antagonist, such as an antagonistic LAG-3 antibody. Suitable LAG3 antibodies include, for example, BMS-986016 (WOlO/ 19570, WO 14/08218), or IMP-731 or IMP-321 (WO08/ 132601, WO09/44273).

In one embodiment, a subject having a disease that may benefit from stimulation of the immune system, e.g., cancer or an infectious disease, is treated by administration to the subject of Gal9 antagonist and an immuno-oncology agent, wherein the immuno-oncology agent is a CD137 (4-1BB) agonist, such as an agonistic CD137 antibody. Suitable CD137 antibodies include, for example, urelumab or PF-05082566 (WO12/32433).

In one embodiment, a subject having a disease that may benefit from stimulation of the immune system, e.g., cancer or an infectious disease, is treated by administration to the subject of Gal9 antagonist and an immuno-oncology agent, wherein the immuno-oncology agent is a GITR agonist, such as an agonistic GITR antibody. Suitable GITR antibodies include, for example, TRX-518 (WO06/105021, WO09/009116), MK-4166 (WO 11/028683) or a GITR antibody disclosed in WO2015/031667.

In one embodiment, a subject having a disease that may benefit from stimulation of the immune system, e.g., cancer or an infectious disease, is treated by administration to the subject of Gal9 antagonist and an immuno-oncology agent, wherein the immuno-oncology agent is an OX40 agonist, such as an agonistic OX40 antibody. Suitable OX40 antibodies include, for example, MEDI-6383, MEDI-6469 or MOXR0916 (RG7888; WO06/029879).

In one embodiment, a subject having a disease that may benefit from stimulation of the immune system, e.g., cancer or an infectious disease, is treated by administration to the subject of Gal9 antagonist and an immuno-oncology agent, wherein the immuno-oncology agent is a CD40 agonist, such as an agonistic CD40 antibody. In certain embodiments, the immuno-oncology agent is a CD40 antagonist, such as an antagonistic CD40 antibody. Suitable CD40 antibodies include, for example, lucatumumab (HCD122), dacetuzumab (SGN-40), CP-870,893 or Chi Lob 7/4.

In one embodiment, a subject having a disease that may benefit from stimulation of the immune system, e.g., cancer or an infectious disease, is treated by administration to the subject of Gal9 antagonist and an immuno-oncology agent, wherein the immuno-oncology agent is a CD27 agonist, such as an agonistic CD27 antibody. Suitable CD27 antibodies include, for example, varlilumab (CDX-1127).

In one embodiment, a subject having a disease that may benefit from stimulation of the immune system, e.g., cancer or an infectious disease, is treated by administration to the subject of Gal9 antagonist and an immuno-oncology agent, wherein the immuno-oncology agent is MGA271 (to B7H3) (WO11/109400).

In one embodiment, a subject having a disease that may benefit from stimulation of the immune system, e.g., cancer or an infectious disease, is treated by administration to the subject of Gal9 antagonist and an immuno-oncology agent, wherein the immuno-oncology agent is a KIR antagonist, such as lirilumab.

In one embodiment, a subject having a disease that may benefit from stimulation of the immune system, e.g., cancer or an infectious disease, is treated by administration to the subject of Gal9 antagonist and an immuno-oncology agent, wherein the immuno-oncology agent is an IDO antagonist. Suitable IDO antagonists include, for example, INCB-024360 (WO2006/122150, WO07/75598, WO08/36653, WO08/36642), indoximod, NLG-919 (WO09/73620, WO09/1156652, WO11/56652, WO 12/142237) or F001287.

In one embodiment, a subject having a disease that may benefit from stimulation of the immune system, e.g., cancer or an infectious disease, is treated by administration to the subject of Gal9 antagonist and an immuno-oncology agent, wherein the immuno-oncology agent is a Toll-like receptor agonist, e.g., a TLR2/4 agonist (e.g., *Bacillus* Calmette-Guerin); a TLR7 agonist (e.g., Hiltonol or Imiquimod); a TLR7/8 agonist (e.g., Resiquimod); or a TLR9 agonist (e.g., CpG7909).

In one embodiment, a subject having a disease that may benefit from stimulation of the immune system, e.g., cancer or an infectious disease, is treated by administration to the subject of Gal9 antagonist and an immuno-oncology agent, wherein, the immuno-oncology agent is a TGF-β inhibitor, e.g., GC1008, LY2157299, TEW7197 or IMC-TR1.

6. Exemplary Gal9 Antagonists

In some embodiments, an Gal9 antagonist is a Gal9 antibody. In some embodiments, an Gal9 antagonist for treating cancer may be a non-antibody protein, such as a soluble Gal9 or a portion thereof (e.g., the ECD) that inhibits the interaction between Gal9 and its ligand, optionally further comprising a fusion partner and in the form of a fusion molecule. The antagonist, in other embodiments, may also be a small molecule or small peptide.

Gal9 Antibodies

In some embodiments, antibodies that block binding of Gal9 and its ligand are provided. In some embodiments, antibodies that inhibit Gal9-mediated signaling are provided. In some such embodiments, the antibody is Gal9 antibody. In some embodiments, the Gal9 antibody inhibits binding of Gal9 to its ligand. In some embodiments, Gal9 antibody inhibits Gal9-mediated signaling.

In some embodiments, Gal9 antibody of the invention has a dissociation constant ($K_d$) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M) for Gal9, e.g., for human Gal9. In certain embodiments, Gal9 antibody has a dissociation constant ($K_d$) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M) for Gal9, e.g., for human Gal9.

In some embodiments, a Gal9 antibody having any the characteristics provided herein inhibits at least 25%, 50%, 75%, 80%, 90% or 100% of the signaling of Gal9.

In some embodiments, an antibody binds to Gal9 from multiple species. For example, in some embodiments, an antibody binds to human Gal9, and also binds to Gal9 from at least one non-human mammal selected from mouse, rat, dog, guinea pig, and cynomolgus monkey.

In some embodiments, multispecific antibodies are provided. In some embodiments, bispecific antibodies are provided. Non-limiting exemplary bispecific antibodies include antibodies comprising a first arm comprising a heavy chain/light chain combination that binds a first antigen and a second arm comprising a heavy chain/light chain combination that binds a second antigen. A further non-limiting exemplary multispecific antibody is a dual variable domain antibody. In some embodiments, a bispecific antibody comprises a first arm that inhibits binding of Gal9 and a second arm that stimulates T cells, e.g., by binding CD3. In some embodiments, the first arm binds Gal9.

In certain embodiments, the monoclonal antibodies of the invention or antigen-binding fragments thereof, including humanized monoclonal antibodies or antigen-binding fragments thereof, include one or more point mutations of in amino acid sequences that are designed to improve developability of the antibody. For example, Raybould et al. (Five computational developability guidelines for therapeutic antibody profiling, *PNAS* 116(10): 4025-4030, 2019) described Therapeutic Antibody Profiler (TAP), a computational tool that builds downloadable homology models of variable domain sequences, tests them against five developability guidelines, and reports potential sequence liabilities and canonical forms. The authors further provide TAP as freely available at opig.stats.ox.ac.uk/webapps/sabdab-sabpred/TAP.php.

There are many barriers to therapeutic mAb development, besides achieving the desired affinity to the antigen. These include intrinsic immunogenicity, chemical and conformational instability, self-association, high viscosity, polyspecificity, and poor expression. For example, high levels of hydrophobicity, particularly in the highly variable complementarity-determining regions (CDRs), have repeatedly been implicated in aggregation, viscosity, and polyspecificity. Asymmetry in the net charge of the heavy- and light-chain variable domains is also correlated with self-association and viscosity at high concentrations. Patches of positive and negative charge in the CDRs are linked to high rates of clearance and poor expression levels. Product heterogeneity (e.g., through oxidation, isomerization, or glycosylation) often results from specific sequence motifs liable to post- or co-translational modification. Computational tools are available to facilitate the identification of sequence liabilities Warszawski et al. (Optimizing antibody affinity and stability by the automated design of the variable light-heavy chain interfaces. *PLOS Comput Biol* 15(8): e1007207. https://doi.org/10.1371/journal.pcbi.1007207) also described methods of optimizing antibody affinity and stability by an automated design of the variable light-heave chain interfaces. Additional methods are available to identify potential developability issues of a candidate antibody, and in preferred embodiments of this invention, one or more point mutations can be introduced, via conventional methods, to the candidate antibody to address such issues to lead to an optimized therapeutic antibody of the invention.

The sequences of certain representative antibodies, including the light chain (LC) and heavy chain (HC) variable regions, the CDR regions, and the framework regions (FR), are listed below.

```
HFB9-1hz1-hG1AA
VH-CDR1:
                                        (SEQ ID NO: 2)
GYTFTDYTIH

VH-CDR2:
                                        (SEQ ID NO: 4)
WFYPGSHSIKYAQKFQGR

VH-CDR3:
                                        (SEQ ID NO: 6)
HGGYDGFDY

HCVR:
                                        (SEQ ID NO: 8)
QVQLVQSGAEVKKPGASVKVSCKASGYTFTDYTIHWVRQAPGQGLEWMGWF
YPGSHSIKYAQKFQGRVTMTADTSISTAYMELSRLRSDDTAVYFCTRHGGY
DGFDYWGQGTLVTVSS

VL-CDR1:
                                        (SEQ ID NO: 10)
KSSQSLFYSTNQKNYLA

VL-CDR2:
                                        (SEQ ID NO: 12)
WASTRES

VL-CDR3:
                                        (SEQ ID NO: 14)
QQYYYFPYT

LCVR:
                                        (SEQ ID NO: 16)
DIVMTQSPDSLAVSLGERATINCKSSQSLFYSTNQKNYLAWYQQKPGQPPK
LLIYWASTRESGVPDRFSGSGSGTDFTLTISSLQAEDVAVYYCQQYYYFPY
TFGQGTKLEIK
```

For all the antibody heavy chain sequences, the framework region sequences HFR1-HFR4 are defined by the VH-CDR sequences. For example, HFR1 is the sequence of HCVR that is N-terminal to VH-CDR1. HFR2 is the sequence of HCVR that is between VH-CDR1 and VH-CDR2. HFR3 is the sequence of HCVR that is between VH-CDR2 and VH-CDR3. HFR4 is the most C-terminal sequence of HCVR.

Likewise, for all the antibody light chain sequences, the framework region sequences LFR1-LFR4 are defined by the VL-CDR sequences. For example, LFR1 is the sequence of LCVR that is N-terminal to VL-CDR1. LFR2 is the sequence of LCVR that is between VL-CDR1 and VL-CDR2. LFR3 is the sequence of LCVR that is between VL-CDR2 and VL-CDR3. LFR4 is the most C-terminal sequence of LCVR.

The HFR1-HFR4 sequences of HFB9-1hz1-hG1AA is SEQ ID NOs: 1, 3, 5, and 7. The LFR1-LFR4 sequences of HFB9-1hz1-hG1AA is SEQ ID NOs: 9, 11, 13, and 15.

```
HFB9-1hz2-hG1AA
VH-CDR1:
                                        (SEQ ID NO: 18)
GYTFTDYTIH

VH-CDR2:
                                        (SEQ ID NO: 20)
WFYPGSHSIKYAQKFQGR

VH-CDR3:
                                        (SEQ ID NO: 22)
HGGYDGFDY (SEQ ID NO: 24)
QVQLVQSGAEVKKPGSSVKVSCKASGYTFTDYTIH

WVRQAPGQGLEWMGWFYPGSHSIKYAQKFQGRVTT

TADKSTSTAYMELSSLRSEDTAVYFCTRHGGYDGF

DYWGQGTLVTVSS

VL-CDR1:
                                        (SEQ ID NO: 26)
KSSQSLFYSTNQKNYLA

VL-CDR2:
                                        (SEQ ID NO: 28)
WASTRES

VL-CDR3:
                                        (SEQ ID NO: 30)
QQYYYFPYT (SEQ ID NO: 32)
DIVMTQSPDSLAVSLGERATINCKSSQSLFYSTNQ

KNYLAWYQQKPGQPPKLLIYWASTRESGVPDRFSG

SGSGTDFTLTISSLQAEDVAVYYCQQYYYFPYTFG

QGTKLEIK
```

The HFR1-HFR4 sequences of HFB9-1hz2-hG1AA is SEQ ID NOs: 17, 19, 21, and 23. The LFR1-LFR4 sequences of HFB9-1hz2-hG1AA is SEQ ID NOs: 25, 27, 29, and 31.

```
HFB-hz-hG1AA
VH-CDR1:
                                        (SEQ ID NO: 34)
GYTFTDYTIH

VH-CDR2:
                                        (SEQ ID NO: 36)
WFYPGSHSIKYAQKFQGR
```

-continued

```
VH-CDR3:
                              (SEQ ID NO: 38)
HGGYDGFDY (SEQ ID NO: 40)
QVQLVQSGAEVKKPGSSVKVSCKASGYTFTDYTIH

WVRQAPGQGLEWMGWFYPGSHSIKYAQKFQGRVTI

TADKSTSTAYMELSSLRSEDTAVYYCTRHGGYDGF

DYWGQGTLVTVSS

VL-CDR1:
                              (SEQ ID NO: 42)
KSSQSLFYSTNQKNYLA

VL-CDR2:
                              (SEQ ID NO: 44)
WASTRES

VL-CDR3:
                              (SEQ ID NO: 46)
QQYYYFPYT (SEQ ID NO: 48)
DIVMTQSPDSLAVSLGERATINCKSSQSLFYSTNQ

KNYLAWYQQKPGQPPKLLIYWASTRESGPDRFSGS

GSGTDFTLTISSLQAEIVAVYYCQQYYYFPYTFGQ

GTKLEIK
```

The HFR1-HFR4 sequences of HFB9-1hz3-hG1AA is SEQ ID NOs: 33, 35, 37, and 39. The LFR1-LFR4 sequences of HFB9-1hz3-hG1AA is SEQ ID NOs: 41, 43, 45, and 47.

```
HFB9-1hz4-hG1AA
VH-CDR1:
                              (SEQ ID NO: 50)
GYTFTDYTIH

VH-CDR2:
                              (SEQ ID NO: 52)
WFYPGSHSIKYAQKFQGR

VH-CDR3:
                              (SEQ ID NO: 54)
HGGYDGFDY (SEQ ID NO: 56)
QVQLVQSGAEVKKPGSSVKVSCKASGYTFTDYTIH

WVRQAPGQGLEWMGWFYPGSHSIKYAQKFQGRVTI

TADKSTSTAYMELSSLRSEDTAVYYCARHGGYDGF

DYWGQGTLVTVSS

VL-CDR1:
                              (SEQ ID NO: 58)
KSSQSLFYSTNQKNYLA

VL-CDR2:
                              (SEQ ID NO: 60)
WASTRES

VL-CDR3:
                              (SEQ ID NO: 62)
QQYYYFPYT (SEQ ID NO: 64)
DIVMTQSPDSLAVSLGERATINCKSSQSLFYSTNQ

KNYLAWYQQKPGQPPKLLIYWASTRESGVPDRFSG

SGSGTDFTLTISSLQAEDVAVYYCQQYYYFPYTFG

QGTKLEIK
```

The HFR1-HFR4 sequences of HFB9-1hz4-hG1AA is SEQ ID NOs: 49, 51, 53, and 55. The LFR1-LFR4 sequences of HFB9-1hz4-hG1AA is SEQ ID NOs: 57, 59, 61, and 63.

```
HFB9-2hz11-hG1AA
VH-CDR1:
                              (SEQ ID NO: 66)
GYTFTEYTIH

VH-CDR2:
                              (SEQ ID NO: 68)
WPYPGSGSTEYAQKFQG

VH-CDR3:
                              (SEQ ID NO: 70)
HGGYDGFDY (SEQ ID NO: 72)
QVQLVQSGAEVKKPGASVKVSCKASGYTFTEYTIH

WVRQAPGQGLEWMGWFYPGSGSTEYAQRFQGRVTM

TADTSISTAYMELSRLRSDDTAVYFCERHGGYDGF

DYWGQGTTVTVSS

VL-CDR1:
                              (SEQ ID NO: 74)
KSSQSLLYSNNQKNYLA

VL-CDR2:
                              (SEQ ID NO: 76)
WASTRGS

VL-CDR3:
                              (SEQ ID NO: 78)
QQYYSYPFT (SEQ ID NO: 80)
DIVMTQSPDSLAVSLGERATINCKSSQSLLYSNNQ

KNYLAWYQQKPGQPIKLLIYWASTRGSGVPDRFSG

SGSGTDFTLTISSLQAEDVAVYYCQQYYSYPFTFG

GGTKVEIK
```

The HFR1-HFR4 sequences of HFB9-2hz11-hG1AA is SEQ ID NOs: 65, 67, 69, and 71. The LFR1-LFR4 sequences of HFB9-2hz11-hG1AA is SEQ ID NOs: 73, 75, 77, and 79.

```
HFB9-2hz12-hG1AA
VH-CDR1:
                              (SEQ ID NO: 82)
GYTFTEYTIH

VH-CDR2:
                              (SEQ ID NO: 84)
WFYPGSGSAEYAQKFQG

VH-CDR3:
                              (SEQ ID NO: 86)
HGGYDGFDY (SEQ ID NO: 88)
QVQLVQSGAEVKKPGSSVKVSCKASGYTFTEYTIH

WVRQAPGQGLEWMGWFYPGSGSAEYAQKFQGRVTI

TADESTSTAYMELSSLRSEDTAVYYCERHGGYDGF

DYWGQGTTVTVSS

VL-CDR1:
                              (SEQ ID NO: 90)
KSSQSLLYSNNQKNYLA
```

-continued

```
VL-CDR2:
                                      (SEQ ID NO: 92)
WASTRGS

VL-CDR3:
                                      (SEQ ID NO: 94)
QQYYSYPFT (SEQ ID NO: 96)
DIVMTQSPDSLAVSLGERATINCKSSQSLLYSNNQ

KNYLAWYQQKPGQPPKLLIYWASTRGSGVPDRFSG

SGSGTDFTLTISSLQAEDVAVYYCQQYYSYPFTFG

GGTKVEIK
```

The HFR1-HFR4 sequences of HFB9-2hz12-hG1AA is SEQ ID NOs: 81, 83, 85, and 87. The LFR1-LFR4 sequences of HFB9-2hz12-hG1AA is SEQ ID NOs: 89, 91, 93, and 95.

```
HFB9-2hz13-hG1AA
VH-CDR1:
                                      (SEQ ID NO: 98)
GYTFTEYTIH

VH-CDR2:
                                      (SEQ ID NO: 100)
WFYPGSGSTEYAQKFQG

VH-CDR3:
                                      (SEQ ID NO: 102)
HGGYDGFDY (SEQ ID NO: 104)
QVQLVQSGAEVKKPGASVKVSCKASGYTFTEYTIH

WVRQAPGQGLEWMGWFYPGSGSTEYAQKFQGRVTM

TADTSTSTVYMELSSLRSEDTAVYYCERHGGYDGF

DYWGQGTTVTVSS

VL-CDR1:
                                      (SEQ ID NO: 106)
KSSQSLLYSNNQKNYLA

VL-CDR2:
                                      (SEQ ID NO: 108)
WASTRGS

VL-CDR3:
                                      (SEQ ID NO: 110)
QQYYSYPFT (SEQ ID NO: 112)
DIVMTQSPDSLAVSLGERATINCKSSQSLLYSNNQ

KNYLAWYQQKPGQPPKLLIYWASTRGSGPDRPSGS

GSGTDFTLTISSLQAEDVAVYYCQQYYSYPFTFGG

GTKVEIK
```

The HFR1-HFR4 sequences of HFB9-2hz13-hG1AA is SEQ ID NOs: 97, 99, 101, and 103. The LFR1-LFR4 sequences of HFB9-2hz13-hG1AA is SEQ ID NOs: 105, 107, 109, and 111.

```
HFB9-2hz14-hG1AA
VH-CDR1:
                                      (SEQ ID NO: 114)
GYTFTEYTIH
```

-continued

```
VH-CDR2:
                                      (SEQ ID NO: 116)
WFYPGSGSTEYSPSFQG

VH-CDR3:
                                      (SEQ ID NO: 118)
HGGYDGFDY (SEQ ID NO: 120)
EVQLVQSGAEVKKPGESLKISCKGSGYTFTEYTIH

WVRQMPGKGLEWMGWFYPGSGSTEYSPSFQGQVTI

SADKSISTAYLQWSSLKASDTAMYYCERHGGYDGF

DYWGQGTTVTVSS

VL-CDR1:
                                      (SEQ ID NG: 122)
KSSQSLLYSNNQKNYLA

VL-CDR2:
                                      (SEQ ID NO: 124)
WASTRGS

VL-CDR3:
                                      (SEQ ID NO: 126)
QQYYSYPFT (SEQ ID NO: 128)
DIVMTQSPDSLAVSLGERATINCKSSQSLLYSNNQ

KNYLAWYQQKPGQPPKLLIYWASTRGSGVPDRFSG

SGSGTDFTLTISSLQAEDVAVYYCQQYYSYPFTFG

GGTKVEIK
```

The HFR1-HFR4 sequences of HFB9-2hz14-hG1AA is SEQ ID NOs: 113, 115, 117, and 119. The LFR1-LFR4 sequences of HFB9-2hz14-hG1AA is SEQ ID NOs: 121, 123, 125, and 127.

7. Humanized Antibodies

In some embodiments, the Gal9 antibody is a humanized antibody. Humanized antibodies are useful as therapeutic molecules because humanized antibodies reduce or eliminate the human immune response to non-human antibodies (such as the human anti-mouse antibody (HAMA) response), which can result in an immune response to an antibody therapeutic, and decreased effectiveness of the therapeutic.

An antibody may be humanized by any standard method. Non-limiting exemplary methods of humanization include methods described, e.g., in U.S. Pat. Nos. 5,530,101; 5,585,089; 5,693,761; 5,693,762; 6,180,370; Jones et al., Nature 321:522-525 (1986); Riechmann et al, Nature 332:323-27 (1988); Verhoeyen et al, Science 239:1534-36 (1988); and U.S. Publication No. US 2009/0136500. All incorporated by reference.

A humanized antibody is an antibody in which at least one amino acid in a framework region of a non-human variable region has been replaced with the amino acid from the corresponding location in a human framework region. In some embodiments, at least two, at least three, at least four, at least five, at least six, at least seven, at least eight, at least nine, at least 10, at least 11, at least 12, at least 15, or at least 20 amino acids in the framework regions of a non-human variable region are replaced with an amino acid from one or more corresponding locations in one or more human framework regions.

In some embodiments, some of the corresponding human amino acids used for substitution are from the framework regions of different human immunoglobulin genes. That is, in some such embodiments, one or more of the non-human amino acids may be replaced with corresponding amino acids from a human framework region of a first human antibody or encoded by a first human immunoglobulin gene, one or more of the non-human amino acids may be replaced with corresponding amino acids from a human framework region of a second human antibody or encoded by a second human immunoglobulin gene, one or more of the non-human amino acids may be replaced with corresponding amino acids from a human framework region of a third human antibody or encoded by a third human immunoglobulin gene, etc. Further, in some embodiments, all of the corresponding human amino acids being used for substitution in a single framework region, for example, FR2, need not be from the same human framework. In some embodiments, however, all of the corresponding human amino acids being used for substitution are from the same human antibody or encoded by the same human immunoglobulin gene.

In some embodiments, an antibody is humanized by replacing one or more entire framework regions with corresponding human framework regions. In some embodiments, a human framework region is selected that has the highest level of homology to the non-human framework region being replaced. In some embodiments, such a humanized antibody is a CDR-grafted antibody.

In some embodiments, following CDR-grafting, one or more framework amino acids are changed back to the corresponding amino acid in a mouse framework region. Such "back mutations" are made, in some embodiments, to retain one or more mouse framework amino acids that appear to contribute to the structure of one or more of the CDRs and/or that may be involved in antigen contacts and/or appear to be involved in the overall structural integrity of the antibody. In some embodiments, ten or fewer, nine or fewer, eight or fewer, seven or fewer, six or fewer, five or fewer, four or fewer, three or fewer, two or fewer, one, or zero back mutations are made to the framework regions of an antibody following CDR grafting.

In some embodiments, a humanized antibody also comprises a human heavy chain constant region and/or a human light chain constant region.

8. Human Antibodies

In some embodiments, the Gal9 antibody is a human antibody. Human antibodies can be made by any suitable method. Non-limiting exemplary methods include making human antibodies in transgenic mice that comprise human immunoglobulin loci. See, e.g., Jakobovits et al., Proc. Natl. Acad. Sci. USA 90:2551-55 (1993); Jakobovits et al, Nature 362:255-8 (1993); onberg et al, Nature 368:856-9 (1994); and U.S. Pat. Nos. 5,545,807; 6,713,610; 6,673,986; 6,162, 963; 5,545,807; 6,300,129; 6,255,458; 5,877,397; 5,874, 299; and 5,545,806.

Non-limiting exemplary methods also include making human antibodies using phage display libraries. See, e.g., Hoogenboom et al., J. Mol. Biol. 227:381-8 (1992); Marks et al, J. Mol. Biol. 222:581-97 (1991); and PCT Publication No. WO 99/10494.

Human Antibody Constant Regions

In some embodiments, a humanized, chimeric, or human antibody described herein comprises one or more human constant regions. In some embodiments, the human heavy chain constant region is of an isotype selected from IgA, IgG, and IgD. In some embodiments, the human light chain constant region is of an isotype selected from K and 2. In some embodiments, an antibody described herein comprises a human IgG constant region, for example, human IgG1, IgG2, IgG3, or IgG4. In some embodiments, an antibody or Fc fusion partner comprises a C237S mutation, for example, in an IgG1 constant region. In some embodiments, an antibody described herein comprises a human IgG2 heavy chain constant region. In some such embodiments, the IgG2 constant region comprises a P331S mutation, as described in U.S. Pat. No. 6,900,292. In some embodiments, an antibody described herein comprises a human IgG4 heavy chain constant region. In some such embodiments, an antibody described herein comprises an S241P mutation in the human IgG4 constant region. See, e.g., Angal et al. Mol. Immunol. 30 (1): 105-108 (1993). In some embodiments, an antibody described herein comprises a human IgG4 constant region and a human k light chain.

The choice of heavy chain constant region can determine whether or not an antibody will have effector function in vivo. Such effector function, in some embodiments, includes antibody-dependent cell-mediated cytotoxicity (ADCC) and/or complement-dependent cytotoxicity (CDC), and can result in killing of the cell to which the antibody is bound. Typically, antibodies comprising human IgG1 or IgG3 heavy chains have effector function.

In some embodiments, effector function is not desirable. For example, in some embodiments, effector function may not be desirable in treatments of inflammatory conditions and/or autoimmune disorders. In some such embodiments, a human IgG4 or IgG2 heavy chain constant region is selected or engineered. In some embodiments, an IgG4 constant region comprises an S241P mutation.

Any of the antibodies described herein may be purified by any suitable method. Such methods include, but are not limited to, the use of affinity matrices or hydrophobic interaction chromatography. Suitable affinity ligands include the antigen and/or epitope to which the antibody binds, and ligands that bind antibody constant regions. For example, a Protein A, Protein G, Protein A/G, or an antibody affinity column may be used to bind the constant region and to purify an antibody.

In some embodiments, hydrophobic interactive chromatography (HIC), for example, a butyl or phenyl column, is also used for purifying some polypeptides. Many methods of purifying polypeptides are known in the art.

Alternatively, in some embodiments, an antibody described herein is produced in a cell-free system. Nonlimiting exemplary cell-free systems are described, e.g., in Sitaraman et al., Methods Mol. Biol. 498:229-44 (2009); Spirin, Trends Biotechnol. 22:538-45 (2004); Endo et al, Biotechnol. Adv. 21:695-713 (2003).

9. Nucleic Acid Molecules Encoding Gal9 Antagonists

The invention also provides nucleic acid molecules comprising polynucleotides that encode one or more chains of an antibody described herein, such as Gal9 antibody. In some embodiments, a nucleic acid molecule comprises a polynucleotide that encodes a heavy chain or a light chain of an antibody described herein. In some embodiments, a nucleic acid molecule comprises both a polynucleotide that encodes a heavy chain and a polynucleotide that encodes a light chain, of an antibody described herein. In some embodiments, a first nucleic acid molecule comprises a first polynucleotide that encodes a heavy chain and a second nucleic acid molecule comprises a second polynucleotide that encodes a light chain.

In some such embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an antibody described herein comprises a nucleotide sequence that encodes a leader sequence, which, when translated, is located at the N-terminus of the heavy chain or light chain. As discussed above, the leader sequence may be the native heavy or light chain leader sequence, or may be another heterologous leader sequence.

Nucleic acid molecules may be constructed using recombinant DNA techniques conventional in the art. In some embodiments, a nucleic acid molecule is an expression vector that is suitable for expression in a selected host cell, such as a mammalian cell.

10. Vectors

Vectors comprising polynucleotides that encode heavy chains and/or light chains of the antibodies described herein are provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NSO cells. Exemplary such vectors are described, e.g., in Running Deer et al., Biotechnol. Prog. 20:880-889 (2004). In some embodiments, a vector is chosen for in vivo expression of Gal9 antagonist in animals, including humans. In some such embodiments, expression of the polypeptide or polypeptides is under the control of a promoter or promoters that function in a tissue-specific manner. For example, liver-specific promoters are described, e.g., in PCT Publication No. WO 2006/076288.

11. Host Cells

In various embodiments, heavy chains and/or light chains of the antibodies described herein may be expressed in prokaryotic cells, such as bacterial cells; or in eukaryotic cells, such as fungal cells (such as yeast), plant cells, insect cells, and mammalian cells. Such expression may be carried out, for example, according to procedures known in the art.

Exemplary eukaryotic cells that may be used to express polypeptides include, but are not limited to, COS cells, including COS 7 cells; 293 cells, including 293-6E cells; CHO cells, including CHO-S and DG44 cells; PER.C6® cells (Crucell); and NSO cells. In some embodiments, heavy chains and/or light chains of the antibodies described herein may be expressed in yeast. See, e.g., U.S. Publication No. US 2006/0270045 A1. In some embodiments, a particular eukaryotic host cell is selected based on its ability to make desired post-translational modifications to the heavy chains and/or light chains of Gal9 antibody. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc., Nonlimiting exemplary methods are described, e.g., in Sambrook et al., Molecular Cloning, A Laboratory Manual, 3rd ed. Cold Spring Harbor Laboratory Press (2001). Nucleic acids may be transiently or stably transfected in the desired host cells, according to any suitable method.

In some embodiments, one or more polypeptides may be produced in vivo in an animal that has been engineered or transfected with one or more nucleic acid molecules encoding the polypeptides, according to any suitable method.

EXAMPLES

Example 1 Humanized Anti-Gal-9 Antibodies have High Binding Affinity for Human and Mouse Galectin-9

This example demonstrates that the various anti-human Gal-9 humanized antibodies of the invention have high binding affinity towards both human and mouse Gal-9.

Antibody binding affinity was measured using the commercially available Octet system from ForteBio (Creative Biolabs). According to the Creative Biolabs description, the Octet platform is based on bio-layer interferometry (BLI) technology that utilizes a whole set of system including instruments, biosensors, reagents and assay kits to support the evaluation of biomolecular interactions in 96- or 384-well microplates. Octet system uses Dip-and-Read assay mode to avoid the need of microfluidics, and enables the real-time, label-free analysis of affinity as well as kinetics. There are three biosensor-based assay orientations that can be used to explore antibody interaction: tandem blocking, premix blocking and classical sandwich. Compared to Biacore, Octet's dip-and-read assay allows longer analyte-binding steps and favors the rebinding of analyte to the ligand-coated sensors. Meanwhile, faster association time consumes less sample, which saves your precious proteins.

Also according to the Creative Biolabs description, the principle of BLI technology is based on the optical interference pattern of white light reflected from two surfaces—a layer of immobilized protein and an internal reference layer. The binding between a ligand immobilized on the biosensor tip surface and an analyte in solution produces an increase in optical thickness at the biosensor tip, which results in a shift in the interference pattern measured in nanometers. The wavelength shift ($\Delta\lambda$) is a direct measure of the change in optical thickness of the biological layer. When this shift is measured over a period of time, and its magnitude plotted as a function of time, a classic association/dissociation curve is obtained. This interaction is measured in real-time, providing the ability to monitor binding specificity, association rate and dissociation rate, and concentration with outstanding precision and accuracy.

Using this system, antibody affinity towards recombinant human and mouse Gal-9 were measured for selected humanized antibodies of the invention, and the results are summarized in the table below. The data shows that the tested humanized antibodies have mid- to low-nM range high affinity towards both the human and mouse Gal-9 protein/antigen.

| Antibody | Gal-9 | $K_D$ (M) | $K_D$ Error | Ka (1/Ms) | Ka Error | $K_{dis}$ (1/s) | $K_{dis}$ Error | Full $R^2$ |
|---|---|---|---|---|---|---|---|---|
| HFB9-2hz11-hG1AA ref batch | hGal9M | 4.84E−09 | 2.21E−10 | 7.28E+04 | 2.75E+03 | 3.52E−04 | 9.13E−06 | 0.9509 |
| | mGal9M | 3.66E−09 | 3.72E−11 | 1.66E+05 | 1.41E+03 | 6.06E−04 | 3.40E−06 | 0.9886 |
| HFB9-2hz11-hG1AA MF20191024 | hGal9M | 1.96E−09 | 1.22E−10 | 9.14E+04 | 3.04E+03 | 1.79E−04 | 9.45E−06 | 0.949 |
| | mGal9M | 1.15E−09 | 1.03E−11 | 4.02E+05 | 2.53E+03 | 4.62E−04 | 2.93E−06 | 0.9826 |

\* hGal9M-human Galectin 9; mGal9M-mouse Galectin 9.

Figure 1:
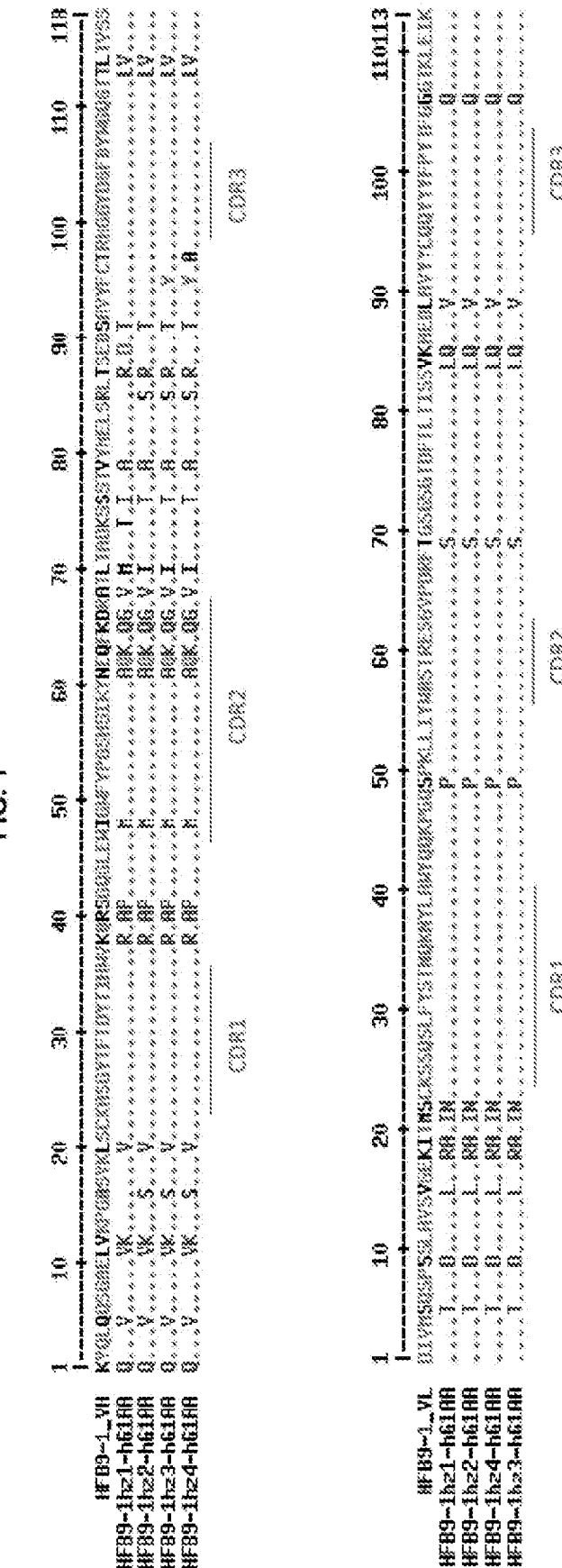
FIG. 1 shows a sequence alignment of various anti-human Galectin-9 humanized antibodies. HFB9-1_VH (SEQ ID NO:129), HFB9-1hz1-hG1AA VH (SEQ ID NO:8), HFB9-1hz2-hG1AA VH (SEQ ID NO:24); HFB9-1hz3-hG1AA VH (SEQ ID NO:40); HFB9-1hz4-hG1AA VH (SEQ ID NO:56); HFB9-1_VL (SEQ ID NO:130), HFB9-1hz1-hG1AA VL (SEQ ID NO: 16), HFB9-1hz2-hG1AA VL (SEQ ID NO:32); HFB9-1hz3-hG1AA VL (SEQ ID NO: 48); HFB9-1hz4-hG1AA VL (SEQ ID NO:64).
Figure 2:
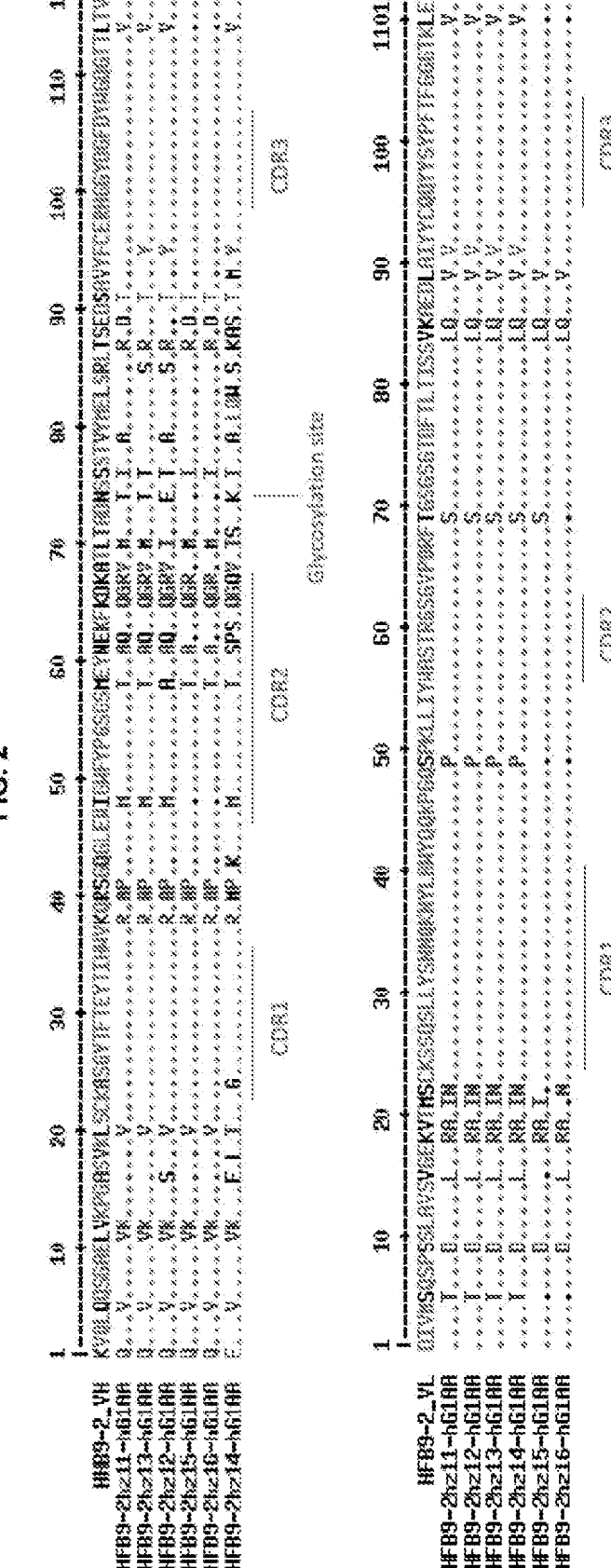
FIG. 2 shows a sequence alignment of various anti-human Galectin-9 humanized antibodies. HFB9-2_VH (SEQ ID NO:131), HFB9-2hz11-hG1AA VH (SEQ ID NO:72), HFB9-2hz12-hG1AA VH (SEQ ID NO:88); HFB9-2hz13-hG1AA VH (SEQ ID NO:104); HFB9-2hz14-hG1AA VH (SEQ ID NO: 120); HFB9-2hz15-hG1AA VH (SEQ ID NO:133); HFB9-2hz16-hG1AA VH (SEQ ID NO:135); HFB9-2_VL (SEQ ID NO:132), HFB9-2hz11-hG1AA VL (SEQ ID NO:80), HFB9-2hz12-hG1AA VL (SEQ ID NO:96); HFB9-2hz13-hG1AA VL (SEQ ID NO:112); HFB9-2hz14-hG1AA VL (SEQ ID NO:128); HFB9-2hz15-hG1AA VL (SEQ ID NO:134); HFB9-2hz16-hG1AA VL (SEQ ID NO:136).

Sequence alignments for selected humanized antibodies of the invention were performed using standard sequence alignment software, and the results are shown in FIGS. 1 and 2. Specifically, in FIG. 1, the $V_H$ and $V_L$ regions of the 4 humanized antibodies were aligned to show the changes in amino acid residues compared to the original $V_H$ and $V_L$ regions, respectively, of the human-mouse chimeric antibody HFB9-1. Humanization mostly changed amino acid sequences in the framework regions of the heavy and light chain variable regions (HCVR and LCVR). However, extensive changes also occurred within the heavy chain CDR2 sequence (see FIG. 1).

Similarly, in FIG. 2, the $V_H$ and $V_L$ regions of the 6 humanized antibodies were aligned to show the changes in amino acid residues compared to the original VH and VL regions, respectively, of the human-mouse chimeric antibody HFB9-2. Humanization mostly changed amino acid sequences in the framework regions of the heavy and light chain variable regions (HCVR and LCVR). However, extensive changes also occurred within the heavy chain CDR2 sequence, and one residue within the heavy chain CDR1 sequence for one humanized antibody (see FIG. 2).

Example 2 Anti-Gal9 Antibodies Exhibit Sub-Nanomolar (nM) Affinity for Gal9

This experiment demonstrates that the humanized antibodies of the invention exhibit very high (sub-nanomolar) affinity for recombinant human Gal9, and cross-react with recombinant mouse Gal9 as well as monkey Gal9 (data not shown). EC50 values for each tested humanized antibodies were measured over increasing concentrations of each antibody, and the results were tabulated in the table in FIG. 3 for binding to recombinant human Gal9, and in FIG. 4 for binding to recombinant mouse Gal9.

Figure 3:
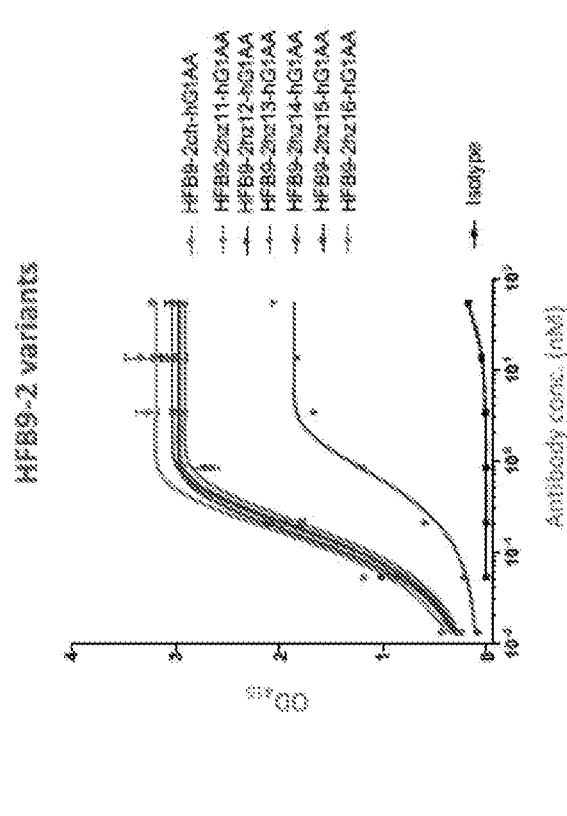
FIG. 3 shows binding affinity (measured as $EC_{50}$ in nM) of the various anti-human Galectin-9 humanized antibodies towards recombinant human Gal-9. An isotype matched antibody against a different antigen is used as a negative control. In one case, the original human-mouse chimeric antibody is also included for comparison.
Figure 4:
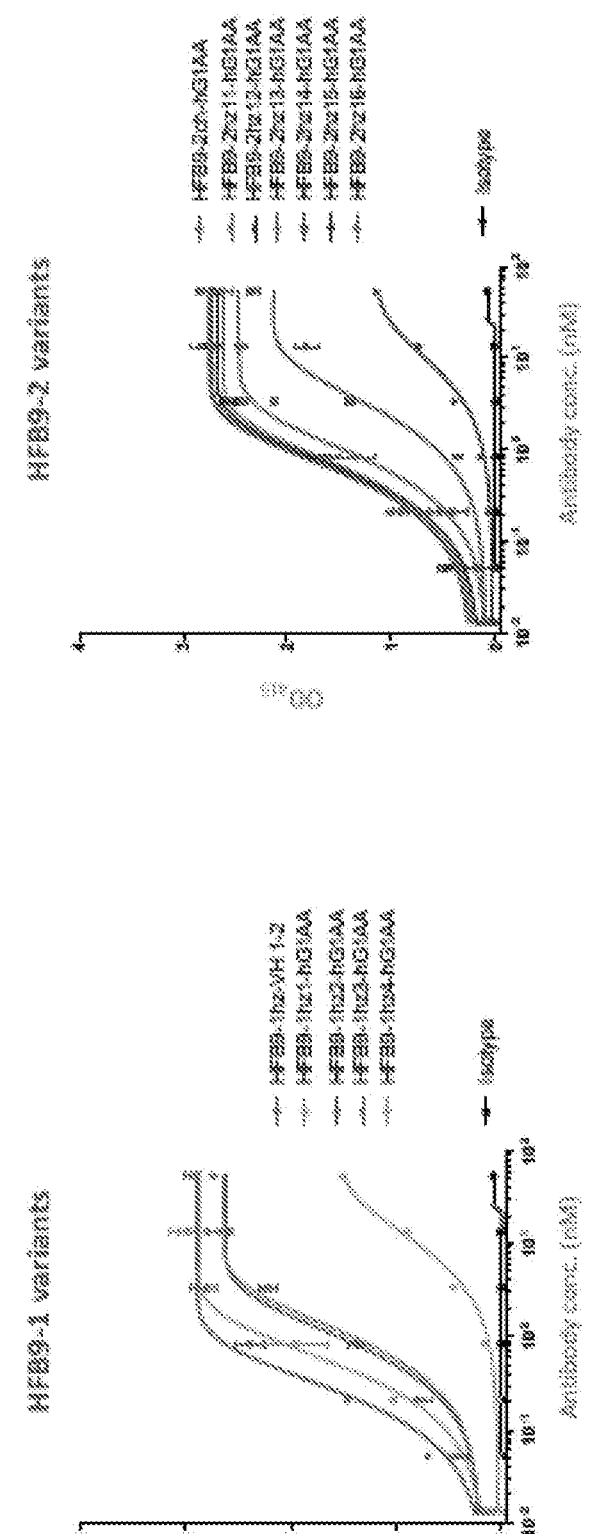
FIG. 4 shows binding affinity (measured as $EC_{50}$ in nM) of the various anti-human Galectin-9 humanized antibodies towards recombinant mouse Gal-9. An isotype matched antibody against a different antigen is used as a negative control. In one case, the original human-mouse chimeric antibody is also included for comparison.

It is apparent that, other than the 1hz4 antibody, all three humanized variants of the HFB9-1 exhibited sub-nM level of affinity for both the human and mouse Gal-9 (see FIGS. 3 and 4). Meanwhile, 5 of the 6 humanized HFB9-2 antibodies (except for 2hz12) exhibited sub-nM level of affinity for human Gal9, but only 4 of the 5 (except for 2h14) maintained sub-nM level of affinity for mouse Gal9.

Strong cross-reactivity against the monkey ortholog Gal9 was also observed (data not shown).

The sequences of these representative antibodies, including the light chain (LC) and heavy chain (HC) variable regions, the CDR regions, and the framework regions (FR), are listed below.

```
HFB9-1hz1-hG1AA
VH-CDR1:
                                          (SEQ ID NO: 2)

GYTFTDYTIH
```

```
                    -continued
VH-CDR2:
                                          (SEQ ID NO: 4)
WFYPGSHSIKYAQKFQGR

VH-CDR3:
                                          (SEQ ID NO: 6)
HGGYDGFDY

HCVR:
                                          (SEQ ID NO: 8)
QVQLVQSGAEVKKPGASVKVSCKASGYTFTDYTIH

WVRQAPGQGLEWMGWFYPGSHSIKYAQKFQGRVTM

TADTSISTAYMELSRLRSDDTAVYFCTRHGGYDGF

DYWGQGTLVTVSS (SEQ ID NO: 10)
VL-CDR1:
KSSQSLFYSTNQKNYLA

VL-CDR2:
                                          (SEQ ID NO: 12)
WASTRES

VL-CDR3:
                                          (SEQ ID NO: 14)
QQYYYFPYT

VL-LCVR:
                                          (SEQ ID NO: 16)
DIVMTQSPDSLAVSLGERATINCKSSQSLFYSTNQ

KNYLAWYQQKPGQPPKLLTYWASTRESGVPDRFSG

SGSGTDFTLTISSLQAEDVAVYYCQQYYYFPYTFG

QGTKLEIK
```

For all the antibody heavy chain sequences, the framework region sequences HFR1-HFR4 are defined by the VH-CDR sequences. For example, HFR1 is the sequence of HCVR that is N-terminal to VH-CDR1. HFR2 is the sequence of HCVR that is between VH-CDR1 and VH-CDR2. HFR3 is the sequence of HCVR that is between VH-CDR2 and VH-CDR3. HFR4 is the most C-terminal sequence of HCVR.

Likewise, for all the antibody light chain sequences, the framework region sequences LFR1-LFR4 are defined by the VL-CDR sequences. For example, LFR1 is the sequence of LCVR that is N-terminal to VL-CDR1. LFR2 is the sequence of LCVR that is between VL-CDR1 and VL-CDR2. LFR3 is the sequence of LCVR that is between VL-CDR2 and VL-CDR3. LFR4 is the most C-terminal sequence of LCVR.

The HFR1-HFR4 sequences of HFB9-1hz1-hG1AA is SEQ ID NOs: 1, 3, 5, and 7. The LFR1-LFR4 sequences of HFB9-1hz1-hG1AA is SEQ ID NOs: 9, 11, 13, and 15.

```
HFB9-1hz2-hG1AA
VH-CDR1:
                              (SEQ ID NO: 18)
GYTFTDYTIH

VH-CDR2:
                              (SEQ ID NO: 20)
WFYPGSHSIKYAQKFQGR

VH-CDR3:
                              (SEQ ID NO: 22)
HGGYDGFDY (SEQ ID NO: 24)
QVQLVQSGAEVKKPGSSVKVSCKASGYTFTDYTIH

WVRQAPGQGLEWMGWFYPGSHSIKYAQKFQGRVTI

TADKSTSTAYMELSSLRSEDTAVYFCTRHGGYDGF

DYWGQGTLVTVSS

VL-CDR1:
                              (SEQ ID NO: 26)
KSSQSLFYSTNQKNYLA

VL-CDR2:
                              (SEQ ID NO: 28)
WASTRES

VL-CDR3:
                              (SEQ ID NO: 30)
QQYYYFPYT (SEQ ID NO: 32)
DIVMTQSPDSLAVSLGERATINCKSSQSLFYSTNQ

KNYLAWYQQKPGQPPKLLIYWASTRESGVPDRFSG

SGSGTDFTLTISSLQAEDVAVYYCQQYYYFPYTFG

QGTKLEIE
```

The HFR1-HFR4 sequences of HEB9-1hz2-bG1AA is SEQ ID NOs. 17, 19, 21, and 23. The LFR1-LFR4 sequences of HFB9-1hz2-hG1AA is SEQ ID NOs: 25, 27, 29, and 31.

```
HFB9-1hz3-hG1AA
VH-CDR1:
                              (SEQ ID NO: 34)
GYTFTDYTIH

VH-CDR2:
                              (SEQ ID NO: 36)
WPYPGSHSIKYAOKFQGR

VH-CDR3:
                              (SEQ ID NO: 38)
HGGYDGFDY (SEQ ID NO: 40)
QVQLVQSGAEVKKPGSSVKVSCKASGYTFTDYTIH

WVRQAPGQGLEWMGWFYPGSHSIKYAQKFQGRVTI

TADKSTSTAYMELSSLRSEDTAVYYCTRHGGYDGF

DYWGQGTLVTVSS
```

```
-continued
VL-CDR1:
                              (SEQ ID NO: 42)
KSSQSLFYSTNQKNYLA

VL-CDR2:
                              (SEQ ID NO: 44)
WASTRES

VL-CDR3:
                              (SEQ ID NO: 46)
QQYYYFPYT (SEQ ID NO: 48)
DIVMTQSPDSLAVSLGERATINCKSSQSLFYSTNQ

KNYLAWYQQKPGQPPKLLIYWASTRESGVPDRFSG

SGSGTDFTLTISSLQAEDVAVYYCQQYYYFPYTFG

QGTKLEIK
```

The HFR1-HFR4 sequences of HFB9-1hz3-hG1AA is SEQ ID NOs: 33, 35, 37, and 39. The LFR1-LFR4 sequences of HFB9-1hz3-hG1AA is SEQ ID NOs: 41, 43, 45, and 47.

```
HFB9-1hz4-hG1AA
VH-CDR1:
                              (SEQ ID NO: 50)
GYTFTDYTIH

VH-CDR2:
                              (SEQ ID NO: 52)
WFYPGSHSIKYAQKFQGR

VH-CDR3:
                              (SEQ ID NO: 54)
HGGYDGFDY (SEQ ID NO: 56)
QVQLVQSGAEVKKPGSSVKVSCKASGYTFTDYTIHW

VRQAPGQGLEWMGWFYPGSHSIKYAQKFQGRVTIT

ADKSTSTAYMELSSLRSEDTAVYYCARHGGYDGFD

YWGQGTLVTVSS

VL-CDR1:
                              (SEQ ID NO: 58)
KSSQSLFYSTNOKNYLA

VL-CDR2:
                              (SEQ ID NO: 60)
WASTRES

VL-CDR3:
                              (SEQ ID NO: 62)
QQYYYFPYT (SEQ ID NO: 64)
DIVMTQSPDSLAVSLGERATINCKSSQSLFYSTNQ

KNYLAWYQQKPGQPPKLLIYWASTRESGVPDRPSG

SGSGTDFTLTISSLQAEDVAVYYCQQYYYFPYTFG

QGTKLEIK
```

The HFR1-HER4 sequences of HFB9-1hz4-hG1AA is SEQ ID NOs: 49, 51, 53, and 55. The LFR1-LFR4 sequences of HFB9-1hz4-hG1AA is SEQ ID NOs: 57, 59, 61, and 63.

```
HFB9-2hz11-hG1AA
VH-CDR1:
```

-continued (SEQ ID NO: 66)
GYTFTEYTIH

VH-CDR2:
(SEQ ID NO: 68)
WFYPGSGSTEYAQKFQG

VH-CDR3:
(SEQ ID NO: 70)
HGGYDGFDY (SEQ ID NO: 72)
QVQLVQSGAEVKKPGASVKVSCKASGYTFTEYTLH

WVRQAPGQGLEWMGWFYPGSGSTEYAQKFQGRVTM

TADTSISTAYMELSRLRSDDTAVYFCERHGGYDGF

DYWGQGTTVTVSS

VL-CDR1:
(SEQ ID NO: 74)
KSSQSLLYSNNQKNYLA

VL-CDR2:
(SEQ ID NO: 76)
WASTRGS

VL-CDR3:
(SEQ ID NO: 78)
QQYYSYPPT (SEQ ID NO: 80)
DIVMTQSPDSLAVSLGERATINCKSSQSLLYSNNQ

KNYLAWYQQKPGQPPKLLIYWASTRGSGVPDRFSG

SGSGTDFTLTISSLQAEDVAVYYCQQYYSYPFTFG

GGTKVEIK

The HFR1-HFR4 sequences of HFB9-2hz11-hG1AA is SEQ ID NOs: 65, 67, 69, and 71. The LFR1-LFR4 sequences of HFB9-2hz11-hG1AA is SEQ ID NOs: 73, 75, 77, and 79.

HFB9-2hz12-hG1AA
VH-CDR1:
(SEQ ID NO: 82)
GYTFTEYTIH

VH-CDR2:
(SEQ ID NO: 84)
WPYPGSGSAEYAQKFQG

VH-CDR3:
(SEQ ID NO: 86)
HGGYDGFDY (SEQ ID NO: 88)
QVQLVQSGAEVKKPGSSVKVSCKASGYTFTEYTIH

WVRQAPGQGLEWMGWFYPGSGSAEYAQKFQGRVTI

TADESTSTAYMELSSLRSEDTAVYYCERRGGYDGF

DYWGQGTTVTVSS

VL-CDR1:
(SEQ ID NO: 90)
KSSQSLLYSNNQKNYLA

VL-CDR2:
(SEQ ID NO: 92)
WASTRGS

VL-CDR3:
(SEQ ID NO: 94)
QQYYSYPFT

-continued (SEQ ID NO: 96)
DIVMTQSPDSLAVSLGERATINCKSSQSLLYSNNQ

KNYLAWYQQKPGQPPKLLIYWASTRGSGVPDRFSG

SGSGTDFTLTISSLQAEDVAVYYCQQYYSYPFTFG

GGTKVEIK

The HFR1-HFR4 sequences of HFB9-2hz12-hG1AA is SEQ ID NOs: 81, 83, 85, and 87. The LFR1-LFR4 sequences of HFB9-2hz12-hG1AA is SEQ ID NOs: 89, 91, 93, and 95.

HFB9-2hz13-hG1AA
VH-CDR1:
(SEQ ID NO: 98)
GYTFTEYTIH

VH-CDR2:
(SEQ ID NO: 100)
WFYPGSGSTEYAQKFQG

VH-CDR3:
(SEQ ID NO: 102)
HGGYDGFDY (SEQ ID NO: 104)
QVQLVQSGAEVKKPGASVKVSCKASGYTFTEYTIH

WVRQAPGQGLEWMGWFYPGSGSTEYAQKFQGRVTM

TADTSTSTVYMELSSLRSEDTAVYYCERHGGYDGF

DYWGQGTTVTVSS

VL-CDR1:
(SEQ ID NO: 106)
KSSQSLLYSNNQKNYLA

VL-CDR2:
(SEQ ID NO: 108)
WASTRGS

VL-CDR3:
(SEQ ID NO: 110)
QQYYSYPFT (SEQ ID NO: 112)
DIVMTQSPDSLAVSLGERATINCKSSQSLLYSNNQ

KNYLAWYQQKPGQPPKLLIYWASTRGSGVPDRFSG

SGSGTDFTLTISSLQAEDVAVYYCQQYYSYPFTFG

GGTKVEIK

The HFR1-HFR4 sequences of HFB9-2hz13-hG1AA is SEQ ID NOs: 97, 99, 101, and 103. The LFR1-LFR4 sequences of HFB9-2hz13-hG1AA is SEQ ID NOs: 105, 107, 109, and 111.

HFB9-2hz14-hG1AA
(SEQ ID NO: 114)
VH-CDR1:
GYTFTEYTIH

VH-CDR2:
(SEQ ID NO: 116)
WFYPGSGSTEYSPSFQG

VH-CDR3:
(SEQ ID NO: 118)
HGGYDGFDY

-continued

```
                              (SEQ ID NO: 120)
EVQLVQSGAEVKKPGESLKISCKGSGYTFTEYTIH

WVRQMPGKGLEWMGWFYPGSGSTEYSPSFQGQVTI

SADKSISTAYLQWSSLKASDTAMYYCERHGGYDGF

DYWGQGTTVTVSS

VL-CDR1:
                              (SEQ ID NO: 122)
KSSQSLLYSNNQKNYLA

VL-CDR2:
                              (SEQ ID NO: 124)
WASTRGS

VL-CDR3:
                              (SEQ ID NO: 126)
QQYYSYPFT (SEQ ID NO: 128)
DIVMTQSPDGLAVSLGBRATINCKSSQSLLYSNNQ

KNYLAWYQQKPGQPPKLLIYWASTRGSGVPDRFSG

SGSGTDFTLTISSLQAEDVAVYYCQQYYSYPFTFG

GGTKVEIK
```

The HFR1-HFR4 sequences of HFB9-2hz14-hG1AA is SEQ ID NOs: 113, 115, 117, and 119. The LFR1-LFR4 sequences of HFB9-2hz14-hG1AA is SEQ ID NOs: 121, 123, 125, and 127.

Example 3 Binding by Anti-Gal9 Antibodies Blocks Gal9 Binding to Receptors TIM3 and CD44

This experiment demonstrates that the anti-Gal9 antibodies of the invention can block Gal-9 binding to its receptors TIM3 and CD44, thus antagonizing downstream signaling from Gal-9.

The data in FIG. 5 clearly showed that the humanized antibodies of the invention blocked Gal9 binding to both the TIM3 and CD44 receptors in a dose-dependent manner.

Example 4 Anti-Gal9 Antibodies Neutralize Gal9-Induced Th1 Apoptosis

Yang et al. (*Inflammation* 40 (3): 1062-1071, 2017) reported that elevated Galectin-9 suppresses Th 1 effector function and induces apoptosis of activated CD4$^+$ T cells in osteoarthritis. This experiment demonstrates that the anti-Gal9 antibodies of the invention neutralize Gal9-induced Th1 apoptosis.

Figure 6:
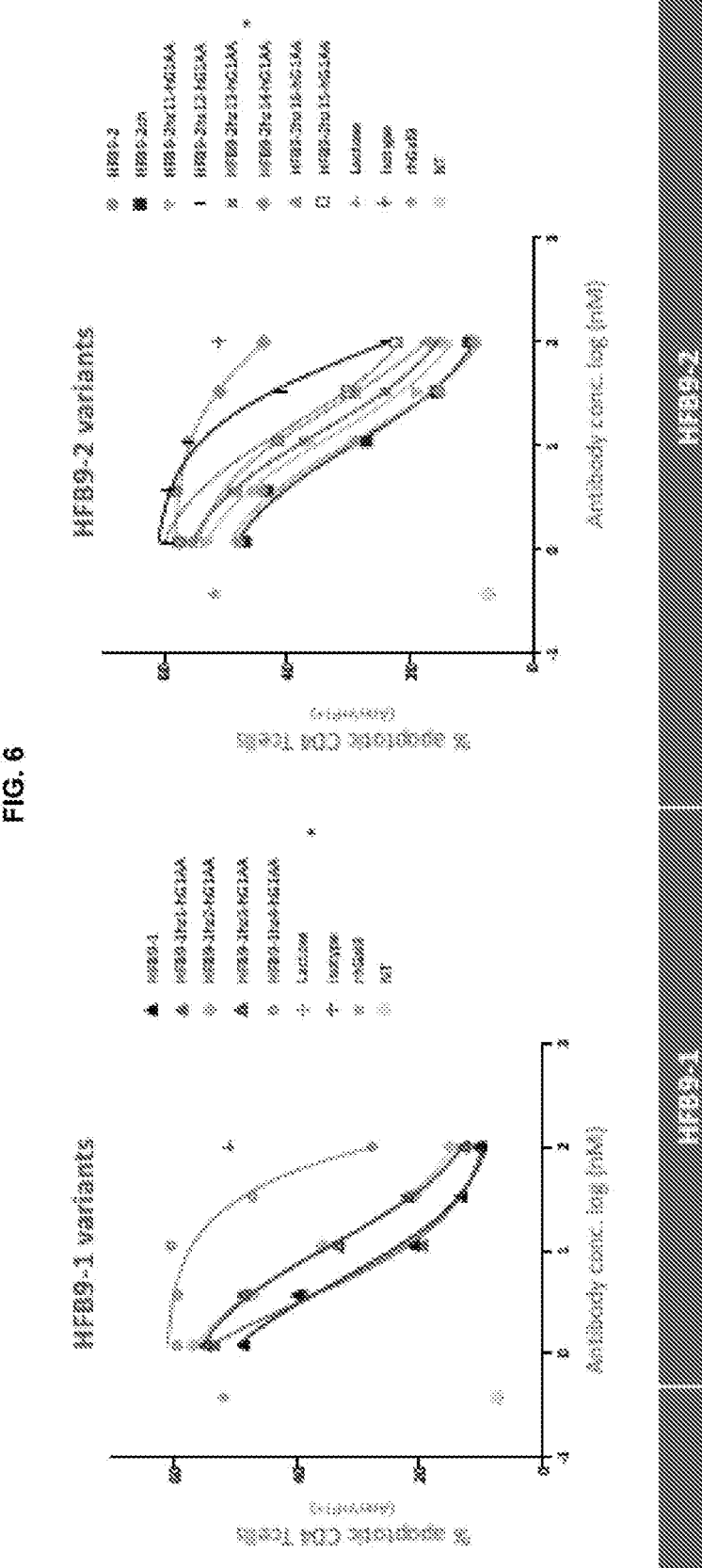
FIG. 6 shows the ability of the various anti-human Galectin-9 humanized antibodies of the invention to neutralize Gal-9-induced Th1 cell apoptosis.

Specifically, human PBMCs were isolated from healthy donors, and were incubated with increasing concentrations of the antibodies of the invention at the presence of an amount of Gal9 that induces T cell apoptosis in the absence of antibody. The percentages of apoptotic CD4+ T cells were determined over the antibody concentration range to determine EC50 values for the antibodies. The results were summarized in FIG. 6. The data clearly showed that treatment of human PBMCs from healthy donors with the antibodies of the invention prevented Gal-9-induced Th1 cell apoptosis in a dose dependent manner.

Example 5 Anti-Gal9 Antibodies Suppress Gal9-Induced Treg Expansion

As discussed above, Galectin-9 is directly expressed by Tregs, which activation is associated with increased expression of Gal9. This experiment demonstrates that inhibition of Galectin-9 by the anti-Gal9 antibody of the invention suppresses Treg expansion.

Figure 7:
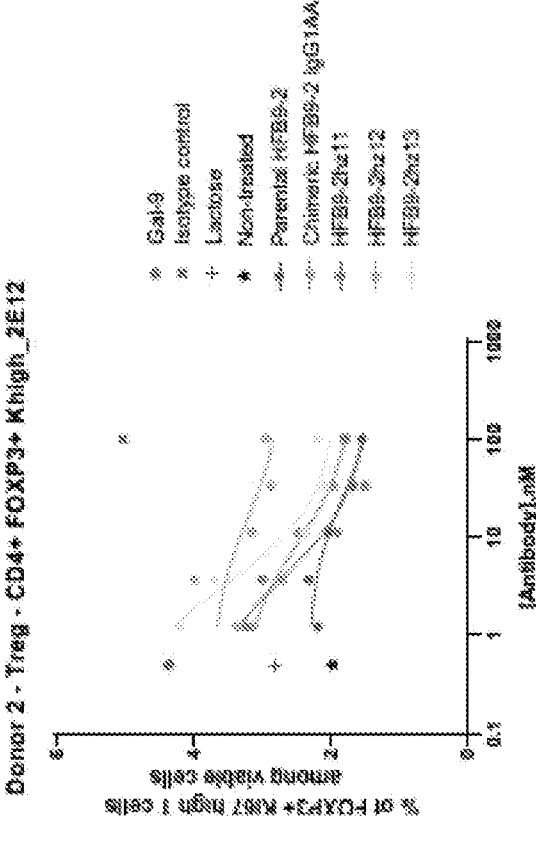
FIG. 7 shows the ability of the various anti-human Galectin-9 humanized antibodies of the invention to neutralize Gal-9-induced Tregs expansion.
Figure 7:
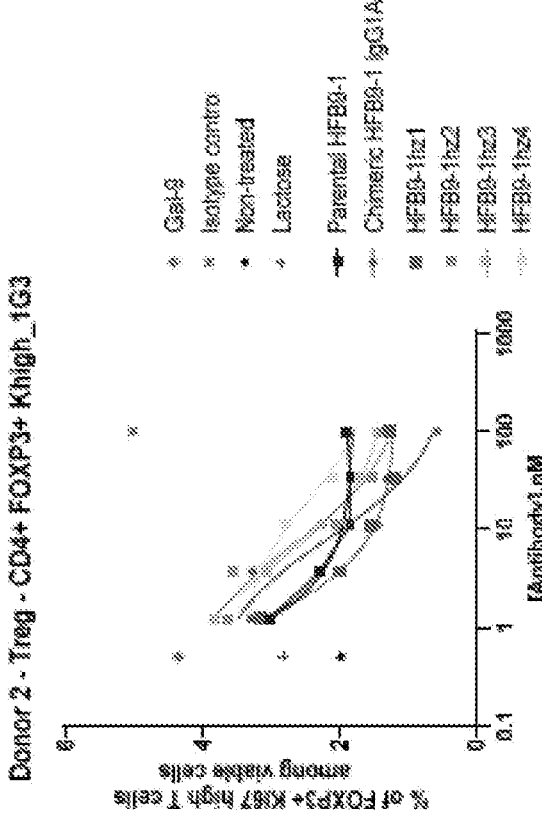

Specifically, human PBMCs were isolated from healthy donors, and were incubated with increasing concentrations of the antibodies of the invention at the presence of an amount of Gal9 that stimulates Treg expansion in the absence of antibody. The percentages of Foxp3$^+$Ki67$^{high}$ T cells among all viable cells were determined over the antibody concentration range to determine EC50 values for the antibodies. The results were summarized in FIG. 7. The data clearly showed that treatment of human PBMCs from healthy donors with the antibodies of the invention suppressed Gal-9-induced Treg expansion in a dose dependent manner, in that higher antibody concentrations were associated with lower percentages of expanded Tregs based on the Foxp3 and Ki67 marker genes expression.

Example 6 Combination Treatment with Anti-Gal9 Antibody and Anti-PD-1 Antibody Showed Synergistic Effect in Inhibiting Tumor Growth In Vivo and Prolonging Survival This experiment demonstrates that the anti-Gal9 monoclonal antibodies of the invention and anti-PD-1 antibody have synergistic effect in inhibiting tumor growth in vivo in a xenograph mouse model.

In particular, about half million cancer cells were innoculated into experimental mice and the tumor mass was allowed to grow to a pre-determined size. Mice were then randomized and injected intraperitoneally (i.p.) with one of four antibody or antibody combinations: (1) IgG isotype control at a dose of 10 mg/kg, (2) anti-Gal9 antibody HFB9-2 (clone RMP1-14) at a dose of 10 mg/kg. (3) anti-mPD-1 antibody at a dose of 10 mg/kg, or (4) a combination of anti-mPD-1 antibody at 10 mg/kg and anti-HFB9-2 antibody at 10 mg/kg.

Figure 8:
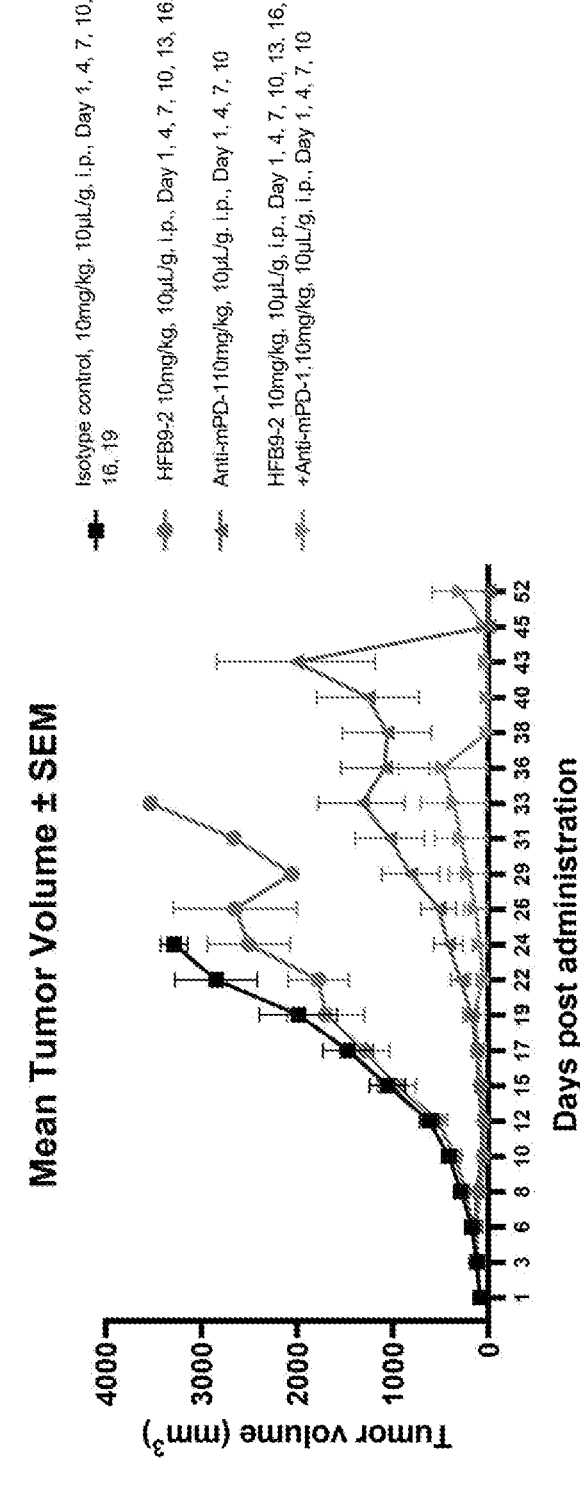
FIG. 8 shows the ability of the various anti-human Galectin-9 humanized antibodies of the invention to promote long term survival when used in combination with anti-PD1 antibodies. The data demonstrates that combination therapy

The first dose of the antibodies for the various groups were administered on Day 1, and subsequent doses were administered every 3 days, for four doses in total for any groups with anti-mPD-1 antibody, and for seven doses in total for any groups with anti-HFB9-2 antibody and the control antibody. Data are presented as mean±s.e.m. (n=8 mice per group) (FIG. 8).

It is apparent that the subject anti-Gal9 antibody and anti-mPD-1 antibody exhibited synergistic effect in inhibiting tumor growth in vivo, in that the combination therapy essentially completely suppressed tumor growth to no more than 500 mm$^3$ during the 7-week study period. Meanwhile, tumor growth in the control group and the anti-HFB9-2 group exceeded this level as early as 2 weeks, and the anti-mPD-1 group exceeded this level as early as 4 weeks.

Furthermore, in terms of survival (FIG. 9), all mice in the control group died around the end of week 3, all mice in the anti-HFB9-2 antibody group died around the end of week 5, and only 25% of the mice (2 out of 8) in the anti-mPD-1 group survived tumor-free at the end of week 7. By the same time, however, the combination therapy group had 75% survival rate, including 5 out of 8 mice tumor-free, and one with about 100 mm$^3$ tumor.

This surprising finding strongly suggests that simultaneously inhibiting Gal-9 function and the PD-1/PD-L1 immune checkpoint can synergistically inhibit tumor growth in vivo and prolong survival.

Example 7 Anti-Gal9 Antibodies are Stable

In order to confirm that the subject humanized anti-Gal9 antibodies are stable in storage, thus suitable for further development as a therapeutic agent, a variety of develop-ability assays were run for selected humanized antibodies.

In the first experiment, 1-2.75 mg/mL of the subject humanized antibodies, HFB9-1hz1-hG1AA, HFB9-1hz2-hG1AA, HFB9-1hz3-hG1AA, HFB9-2hz11-hG1AA, and HFB9-2hz13-hG1AA, were stored at 25 or 40° C. in PBS (pH7.4), and the stability of the various antibodies were determined on Days 0, 3, 7, and 14. The results (not show) demonstrated that all tested antibodies were stable at the conditions tested.

In the second experiment, the same antibodies were tested for stability under low pH conditions (100 mM AcH, pH3.5, 25° C.), for 0, 3, and 6 hours. The results (not show) again demonstrated that all tested antibodies were stable at the conditions tested.

In the third experiment, the same antibodies were subject to 1, 2, or 3 freeze-thaw cycles. The results (not show) again demonstrated that all tested antibodies were stable at the conditions tested.

Example 8 Galectin-9 Levels in Plasma and Serum from AML Patients

To determine the levels of Gal-9 in patient plasma and serum, peripheral blood samples from AML patients were obtained from the Clinical Hematology Department of the Gustave Roussy Institute (Villejuif, FRANCE), in accordance to Institutional Review Board-approved protocols. Informed consent was obtained from all patients, in accordance with the Declaration of Helsinki. Patients were stratified according to the French-American-British (FAB) classification criteria. Peripheral blood-derived plasma or serum from AML patients were prepared following standard procedures. For Healthy Donors, plasma or serum samples were obtained from commercial sources.

Galectin-9 protein levels in plasma or serum were assessed by ELISA, using the "Quantikine® ELISA Human Galectin-9" from R&D SYSTEMS® and statistical analyses (unpaired, two-tailed t-tests) were performed using the PRISM® 5 for Windows software.

As shown in FIG. 10, Galectin-9 protein levels in plasma of AML patients at the diagnosis or relapse/refractory stages (R/R) of the disease were significantly higher than those observed in plasma from healthy individuals. Galectin-9 protein levels in plasma of AML patients at complete remission post chemotherapy were close to the normal, physiological range.

As shown in FIG. 11, Galectin-9 protein levels in plasma of FAB M2 or FAB M3 AML patients at diagnosis were significantly lower than those observed in plasma from FAB M0, MI, M4 or M5 AML patients. Galectin-9 protein levels in plasma of FAB M3 AML patients at diagnosis were within the normal, physiological range.

Additionally, the LGALS9 mRNA expression levels were examined in AML patients and healthy individuals. LGALS9 mRNA expression levels were extracted from the publicly available "AML_Ohsu_Nature 2018" dataset deposited by Tyner et al (see PMID 30333627 for a complete description of the study). Data are expressed as normalized log 2 RPKM in FIG. 12. Dotted lines represent the medians of LGALS9 levels in BM-derived MNC from healthy individuals or AML patients, respectively.

As shown in FIG. 12, Galectin-9-encoding mRNA levels in BM-derived MNC from AML patients at diagnosis (all FAB considered) were higher than those observed in BM-derived MNC or CD34+ cells from healthy individuals. Additionally, Galectin-9-encoding mRNA levels in BM-derived MNC from FAB M3 AML patients at diagnosis were significantly lower than those observed in BM-derived MNC from FAB M0, MI, M4 or M5 AML patients or from BM-derived MNC or CD34+ cells from healthy individuals.

What is claimed is:

1. An isolated monoclonal antibody, or an antigen-binding fragment thereof, wherein said monoclonal antibody or antigen-binding fragment thereof is specific for Galectin-9, and wherein said monoclonal antibody comprises:

(1a) a heavy chain variable region (HCVR), comprising the HCVR CDR1 sequence of SEQ ID NO: 2, the HCVR CDR2 sequence of SEQ ID NO: 4, and the HCVR CDR3 sequence of SEQ ID NO: 6; and, (1b) a light chain variable region (LCVR), comprising the LCVR CDR1 sequence of SEQ ID NO: 10, the LCVR CDR2 sequence of SEQ ID NO: 12, and the LCVR CDR3 sequence of SEQ ID NO: 14; or (2a) a heavy chain variable region (HCVR), comprising the HCVR CDR1 sequence of SEQ ID NO: 18, the HCVR CDR2 sequence of SEQ ID NO: 20, and the HCVR CDR3 sequence of SEQ ID NO: 22; and, (2b) a light chain variable region (LCVR), comprising the LCVR CDR1 sequence of SEQ ID NO: 26, the LCVR CDR2 sequence of SEQ ID NO: 28, and the LCVR CDR3 sequence of SEQ ID NO: 30; or (3a) a heavy chain variable region (HCVR), comprising the HCVR CDR1 sequence of SEQ ID NO: 34, the HCVR CDR2 sequence of SEQ ID NO: 36, and the HCVR CDR3 sequence of SEQ ID NO: 38; and, (3b) a light chain variable region (LCVR), comprising the LCVR CDR1 sequence of SEQ ID NO: 42, the LCVR CDR2 sequence of SEQ ID NO: 44, and the LCVR CDR3 sequence of SEQ ID NO: 46; or (4a) a heavy chain variable region (HCVR), comprising the HCVR CDR1 sequence of SEQ ID NO: 50, the HCVR CDR2 sequence of SEQ ID NO: 52, and the HCVR CDR3 sequence of SEQ ID NO: 54; and, (4b) a light chain variable region (LCVR), comprising the LCVR CDR1 sequence of SEQ ID NO: 58, the LCVR CDR2 sequence of SEQ ID NO: 60, and the LCVR CDR3 sequence of SEQ ID NO: 62; or (5a) a heavy chain variable region (HCVR), comprising the HCVR CDR1 sequence of SEQ ID NO: 66, the HCVR CDR2 sequence of SEQ ID NO: 68, and the HCVR CDR3 sequence of SEQ ID NO: 70; and, (5b) a light chain variable region (LCVR), comprising the LCVR CDR1 sequence of SEQ ID NO: 74, the LCVR CDR2 sequence of SEQ ID NO: 76, and the LCVR CDR3 sequence of SEQ ID NO: 78; or (6a) a heavy chain variable region (HCVR), comprising the HCVR CDR1 sequence of SEQ ID NO: 82, the HCVR CDR2 sequence of SEQ ID NO: 84, and the HCVR CDR3 sequence of SEQ ID NO: 86; and, (6b) a light chain variable region (LCVR), comprising the LCVR CDR1 sequence of SEQ ID NO: 90, the LCVR CDR2 sequence of SEQ ID NO: 92, and the LCVR CDR3 sequence of SEQ ID NO: 94; or (7a) a heavy chain variable region (HCVR), comprising the HCVR CDR1 sequence of SEQ ID NO: 98, the HCVR CDR2 sequence of SEQ ID NO: 100, and the HCVR CDR3 sequence of SEQ ID NO: 102; and, (7b) a light chain variable region (LCVR), comprising the LCVR CDR1 sequence of SEQ ID NO: 106, the LCVR CDR2 sequence of SEQ ID NO: 108, and the LCVR CDR3 sequence of SEQ ID NO: 110; or (8a) a heavy chain variable region (HCVR), comprising the HCVR CDR1 sequence of SEQ ID NO: 114, the HCVR CDR2 sequence of SEQ ID NO: 116, and the HCVR CDR3 sequence of SEQ ID NO: 118; and, (8b) a light chain variable region (LCVR), comprising the LCVR CDR1 sequence of SEQ ID NO: 122, the LCVR CDR2 sequence of SEQ ID NO: 124, and the LCVR CDR3 sequence of SEQ ID NO: 126.

2. The isolated monoclonal antibody or antigen-binding fragment thereof of claim 1, wherein:

(1c) the antibody or antigen-binding fragment thereof of (1a) and (1b) further comprises the heavy chain framework region 3 (HFR3) sequence of SEQ ID NO: 5, and optionally further comprises the HFR1 sequence of SEQ ID NO: 1; or (2c) the antibody or antigen-binding fragment thereof of (2a) and (2b) further comprises the HFR3 sequence of SEQ ID NO: 21, and optionally further comprises the HFR1 sequence of SEQ ID NO: 17; or (3c) the antibody or antigen-binding fragment thereof of (3a) and (3b) further comprises the HFR3 sequence of SEQ ID NO: 37, and optionally further comprises the HFR1 sequence of SEQ ID NO: 33; or (4c) the antibody or antigen-binding fragment thereof of (4a) and (4b) further comprises the HFR3 sequence of SEQ ID NO: 53, and optionally further comprises the HFR1 sequence of SEQ ID NO: 49; or (5c) the antibody or antigen-binding fragment thereof of (5a) and (5b) further comprises the HFR3 sequence of SEQ ID NO: 69, and optionally further comprises the HFR1 sequence of SEQ ID NO: 65; or (6c) the antibody or antigen-binding fragment thereof of (6a) and (6b) further comprises the HFR3 sequence of SEQ ID NO: 85, and optionally further comprises the HFR1 sequence of SEQ ID NO: 81; or (7c) the antibody or antigen-binding fragment thereof of (7a) and (7b) further comprises the HFR3 sequence of SEQ ID NO: 101, and optionally further comprises the HFR1 sequence of SEQ ID NO: 97; or (8c) the antibody or antigen-binding fragment thereof of (8a) and (8b) further comprises the HFR3 sequence of SEQ ID NO: 117, and optionally further comprises the HFR1 sequence of SEQ ID NO: 113.

3. The isolated monoclonal antibody or antigen-binding fragment thereof of claim 1, wherein:

(1A) the HCVR sequence is SEQ ID NO: 8; and/or, (1B) the LCVR sequence is SEQ ID NO: 16, or, (2A) the HCVR sequence is SEQ ID NO: 24; and/or, (2B) the LCVR sequence is SEQ ID NO: 32, or, (3A) the HCVR sequence is SEQ ID NO: 40; and/or, (3B) the LCVR sequence is SEQ ID NO: 48, or, (4A) the HCVR sequence is SEQ ID NO: 56; and/or, (4B) the LCVR sequence is SEQ ID NO: 64, or, (5A) the HCVR sequence is SEQ ID NO: 72; and/or, (5B) the LCVR sequence is SEQ ID NO: 80, or, (6A) the HCVR sequence is SEQ ID NO: 88; and/or, (6B) the LCVR sequence is SEQ ID NO: 96, or (7A) the HCVR sequence is SEQ ID NO: 104; and/or, (7B) the LCVR sequence is SEQ ID NO: 112, or (8A) the HCVR sequence is SEQ ID NO: 120; and/or, (8B) the LCVR sequence is SEQ ID NO: 128.

4. The isolated monoclonal antibody or antigen-binding fragment thereof according to claim 1, which is a humanized antibody, and comprises:

(1) the HCVR sequence of SEQ ID NO: 8 and the LCVR sequence of SEQ ID NO: 16; or, (2) the HCVR sequence of SEQ ID NO: 72 and the LCVR sequence of SEQ ID NO: 80.

5. The isolated monoclonal antibody or antigen-binding fragment thereof according to claim 1, wherein said antigen-binding fragment thereof is an Fab, Fab', F(ab')$_2$, F$_d$, single chain Fv or scFv, disulfide linked Fv, intrabody, IgG$\Delta$CH$_2$, minibody, F(ab')$_3$, tetrabody, triabody, diabody, single-domain antibody, DVD-Ig, Fcab, mAb$_2$, (scFv)$_2$, or scFv-Fc.

6. The isolated monoclonal antibody or antigen-binding fragment thereof of claim 1, wherein said monoclonal antibody or antigen-binding fragment thereof cross-reacts with mouse Gal9.

7. The isolated monoclonal antibody or antigen-binding fragment thereof of claim 1, wherein said monoclonal antibody or antigen-binding fragment thereof binds to human Gal9 with an EC50 of about 0.1-0.2 nM, and/or binds to mouse Gal9 with an EC50 of about 0.5-1.0 nM.

8. The isolated monoclonal antibody or antigen-binding fragment thereof of claim 1, wherein said monoclonal antibody or antigen-binding fragment thereof binds human Gal9 with a K$_d$ of less than about 25 nM, 20 nM, 15 nM, 10 nM, 5 nM, 2 nM, or 1 nM.

9. The isolated monoclonal antibody or antigen-binding fragment thereof of claim 1, which binds to Gal9 and inhibits Gal9 binding to a Gal9 receptor.

10. The isolated monoclonal antibody or antigen-binding fragment thereof of claim 1, which neutralizes Gal-9-induced Th1 apoptosis of T cells.

11. The isolated monoclonal antibody or antigen-binding fragment thereof of claim 1, which suppresses Gal9-induced Treg expansion.

12. The isolated monoclonal antibody or antigen-binding fragment thereof of claim 1, which synergistically inhibits tumor growth in vivo and/or prolongs survival in a mouse with a xenograph tumor with an antagonist of an immune checkpoint.

13. The isolated monoclonal antibody or antigen-binding fragment thereof of claim 12, wherein the antagonist of the immune checkpoint is an antibody or antigen-binding fragment thereof specific for PD-1 or PD-L1.

14. A method of treating cancer in a patient in need thereof, the method comprising administering to the patient an effective amount of the isolated monoclonal antibody or antigen-binding fragment thereof of claim 1, and an antagonist of an immune checkpoint.

15. The method of claim 14, wherein the immune checkpoint is PD-1/PD-L1 immune checkpoint, wherein the antagonist of the immune checkpoint is an antibody or antigen-binding fragment thereof specific for PD-1 or PD-L1.

16. The method of claim 14, wherein the cancer is a hematological cancer, or a solid tumor.

17. The method of claim 14, further comprising administering to the patient a chemotherapeutic agent, an anti-angiogenesis agent, a growth inhibitory agent, an immune-oncology agent, and/or an anti-neoplastic composition.

18. A method of rescuing or promoting effector T cells proliferation and/or enhancing effector T cell activity in a patient diagnosed with cancer, in risk of developing cancer or having cancer relapse, or a method of identifying and treating a patient having cancer, the method comprising: administering to the patient an effective amount of the isolated monoclonal antibody or antigen-binding fragment thereof of claim 1 and an antagonist of an immune checkpoint, upon identifying the patient as having a level of Galectin-9 in a sample from the patient higher than a reference level of Galectin-9 in a healthy or a control individual.

19. The method of claim 18, further comprising identifying the patient as having the level of Galectin-9 in the sample higher than the reference level, by comparing the level of Galectin-9 in the sample to the reference level.

20. The method of claim 18, wherein the immune checkpoint is PD-1/PD-L1 immune checkpoint.

21. The method of claim 20, wherein the antagonist of the immune checkpoint is an antibody or antigen-binding fragment thereof specific for PD-1 or PD-L1.

22. The method of claim 18, wherein the cancer is a hematological cancer or a solid tumor.

23. The method of claim 22, wherein the patient is a French-American-British (FAB) M0, M1, M4 or M5 AML patient, or wherein the patient is not an FAB M2 or M3 AML patient.

24. The method of claim 18, wherein the sample is a blood sample, a plasma sample, or a serum sample.

25. A method of rescuing or promoting effector T cells proliferation and/or enhancing effector T cell activity in a patient diagnosed with AML, in risk of developing AML or having AML relapse, or a method of identifying and treating a patient having AML, the method comprising: administering to the patient an effective amount of the isolated monoclonal antibody or antigen-binding fragment thereof of claim 1 and an antagonist of an immune checkpoint, upon identifying the patient as having a level of Galectin-9-encoding mRNA in a bone-marrow (BM)-derived mononuclear cell (MNC) sample from the patient statistically significantly higher or lower than a reference level in BM-derived MNC or CD34$^+$ cells in a healthy or a control individual.

26. The method of claim 25, wherein (1) the level of Galectin-9-encoding mRNA in the BM-derived MNC sample from the patient is significantly higher than the reference level when the patient is an FAB M0, M1, M2, M4, or M5 AML patient, or (2) the level of Galectin-9-encoding mRNA in the BM-derived MNC sample from the patient is significantly lower than the reference level when the patient is an FAB M3 AML patient.

* * * * *

SEQUENCE LISTING

```
<160> NUMBER OF SEQ ID NOS: 136

<210> SEQ ID NO 1
<211> LENGTH: 25
<212> TYPE: PRT
<213> ORGANISM: Artificial Sequence
<220> FEATURE:
<223> OTHER INFORMATION: HFR1

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 2
<211> LENGTH: 10
<212> TYPE: PRT
<213> ORGANISM: Artificial Sequence
<220> FEATURE:
<223> OTHER INFORMATION: VH-CDR1

<400> SEQUENCE: 2

Gly Tyr Thr Phe Thr Asp Tyr Thr Ile His
1               5                   10

<210> SEQ ID NO 3
<211> LENGTH: 14
```

<212> TYPE: PRT
<213> ORGANISM: Artificial Sequence
<220> FEATURE:
<223> OTHER INFORMATION: HFR2

<400> SEQUENCE: 3

Trp Val Arg Gln Ala Pro Gly Gln Gly Leu Glu Trp Met Gly
1               5                   10

<210> SEQ ID NO 4
<211> LENGTH: 18
<212> TYPE: PRT
<213> ORGANISM: Artificial Sequence
<220> FEATURE:
<223> OTHER INFORMATION: VH-CDR2

<400> SEQUENCE: 4

Trp Phe Tyr Pro Gly Ser His Ser Ile Lys Tyr Ala Gln Lys Phe Gln
1               5                   10                  15

Gly Arg

<210> SEQ ID NO 5
<211> LENGTH: 31
<212> TYPE: PRT
<213> ORGANISM: Artificial Sequence
<220> FEATURE:
<223> OTHER INFORMATION: HFR3

<400> SEQUENCE: 5

Val Thr Met Thr Ala Asp Thr Ser Ile Ser Thr Ala Tyr Met Glu Leu
1               5                   10                  15

Ser Arg Leu Arg Ser Asp Asp Thr Ala Val Tyr Phe Cys Thr Arg
            20                  25                  30

<210> SEQ ID NO 6
<211> LENGTH: 9
<212> TYPE: PRT
<213> ORGANISM: Artificial Sequence
<220> FEATURE:
<223> OTHER INFORMATION: VH-CDR3

<400> SEQUENCE: 6

His Gly Gly Tyr Asp Gly Phe Asp Tyr
1               5

<210> SEQ ID NO 7
<211> LENGTH: 11
<212> TYPE: PRT
<213> ORGANISM: Artificial Sequence
<220> FEATURE:
<223> OTHER INFORMATION: HFR4

<400> SEQUENCE: 7

Trp Gly Gln Gly Thr Leu Val Thr Val Ser Ser
1               5                   10

<210> SEQ ID NO 8
<211> LENGTH: 118
<212> TYPE: PRT
<213> ORGANISM: Artificial Sequence
<220> FEATURE:
<223> OTHER INFORMATION: HCVR

<400> SEQUENCE: 8

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Asp Tyr
         20              25              30

Thr Ile His Trp Val Arg Gln Ala Pro Gly Gln Gly Leu Glu Trp Met
         35              40              45

Gly Trp Phe Tyr Pro Gly Ser His Ser Ile Lys Tyr Ala Gln Lys Phe
    50              55              60

Gln Gly Arg Val Thr Met Thr Ala Asp Thr Ser Ile Ser Thr Ala Tyr
65              70              75              80

Met Glu Leu Ser Arg Leu Arg Ser Asp Asp Thr Ala Val Tyr Phe Cys
             85              90              95

Thr Arg His Gly Gly Tyr Asp Gly Phe Asp Tyr Trp Gly Gln Gly Thr
         100             105             110

Leu Val Thr Val Ser Ser
        115
```

<210> SEQ ID NO 9
<211> LENGTH: 23
<212> TYPE: PRT
<213> ORGANISM: Artificial Sequence
<220> FEATURE:
<223> OTHER INFORMATION: LFR1

<400> SEQUENCE: 9

```
Asp Ile Val Met Thr Gln Ser Pro Asp Ser Leu Ala Val Ser Leu Gly
1               5               10              15

Glu Arg Ala Thr Ile Asn Cys
            20
```

<210> SEQ ID NO 10
<211> LENGTH: 17
<212> TYPE: PRT
<213> ORGANISM: Artificial Sequence
<220> FEATURE:
<223> OTHER INFORMATION: VL-CDR1

<400> SEQUENCE: 10

```
Lys Ser Ser Gln Ser Leu Phe Tyr Ser Thr Asn Gln Lys Asn Tyr Leu
1               5               10              15

Ala
```

<210> SEQ ID NO 11
<211> LENGTH: 15
<212> TYPE: PRT
<213> ORGANISM: Artificial Sequence
<220> FEATURE:
<223> OTHER INFORMATION: LFR2

<400> SEQUENCE: 11

```
Trp Tyr Gln Gln Lys Pro Gly Gln Pro Pro Lys Leu Leu Ile Tyr
1               5               10              15
```

<210> SEQ ID NO 12
<211> LENGTH: 7
<212> TYPE: PRT
<213> ORGANISM: Artificial Sequence
<220> FEATURE:
<223> OTHER INFORMATION: VL-CDR2

<400> SEQUENCE: 12

```
Trp Ala Ser Thr Arg Glu Ser
1               5
```

```
<210> SEQ ID NO 13
<211> LENGTH: 32
<212> TYPE: PRT
<213> ORGANISM: Artificial Sequence
<220> FEATURE:
<223> OTHER INFORMATION: LFR3

<400> SEQUENCE: 13

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 14
<211> LENGTH: 9
<212> TYPE: PRT
<213> ORGANISM: Artificial Sequence
<220> FEATURE:
<223> OTHER INFORMATION: VL-CDR3

<400> SEQUENCE: 14

Gln Gln Tyr Tyr Tyr Phe Pro Tyr Thr
1               5

<210> SEQ ID NO 15
<211> LENGTH: 10
<212> TYPE: PRT
<213> ORGANISM: Artificial Sequence
<220> FEATURE:
<223> OTHER INFORMATION: LFR4

<400> SEQUENCE: 15

Phe Gly Gln Gly Thr Lys Leu Glu Ile Lys
1               5                   10

<210> SEQ ID NO 16
<211> LENGTH: 113
<212> TYPE: PRT
<213> ORGANISM: Artificial Sequence
<220> FEATURE:
<223> OTHER INFORMATION: LCVR

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Tyr Ser
            20                  25                  30

Thr Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Tyr Phe Pro Tyr Thr Phe Gly Gln Gly Thr Lys Leu Glu Ile
            100                 105                 110

Lys

<210> SEQ ID NO 17
<211> LENGTH: 25
<212> TYPE: PRT
```

<213> ORGANISM: Artificial Sequence
<220> FEATURE:
<223> OTHER INFORMATION: HFR1

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 18
<211> LENGTH: 10
<212> TYPE: PRT
<213> ORGANISM: Artificial Sequence
<220> FEATURE:
<223> OTHER INFORMATION: VH-CDR1

<400> SEQUENCE: 18

Gly Tyr Thr Phe Thr Asp Tyr Thr Ile His
1               5                   10

<210> SEQ ID NO 19
<211> LENGTH: 14
<212> TYPE: PRT
<213> ORGANISM: Artificial Sequence
<220> FEATURE:
<223> OTHER INFORMATION: HFR2

<400> SEQUENCE: 19

Trp Val Arg Gln Ala Pro Gly Gln Gly Leu Glu Trp Met Gly
1               5                   10

<210> SEQ ID NO 20
<211> LENGTH: 18
<212> TYPE: PRT
<213> ORGANISM: Artificial Sequence
<220> FEATURE:
<223> OTHER INFORMATION: VH-CDR2

<400> SEQUENCE: 20

Trp Phe Tyr Pro Gly Ser His Ser Ile Lys Tyr Ala Gln Lys Phe Gln
1               5                   10                  15

Gly Arg

<210> SEQ ID NO 21
<211> LENGTH: 31
<212> TYPE: PRT
<213> ORGANISM: Artificial Sequence
<220> FEATURE:
<223> OTHER INFORMATION: HFR3

<400> SEQUENCE: 21

Val Thr Ile Thr Ala Asp Lys Ser Thr Ser Thr Ala Tyr Met Glu Leu
1               5                   10                  15

Ser Ser Leu Arg Ser Glu Asp Thr Ala Val Tyr Phe Cys Thr Arg
            20                  25                  30

<210> SEQ ID NO 22
<211> LENGTH: 9
<212> TYPE: PRT
<213> ORGANISM: Artificial Sequence
<220> FEATURE:
<223> OTHER INFORMATION: VH-CDR3

<400> SEQUENCE: 22

-continued

```
His Gly Gly Tyr Asp Gly Phe Asp Tyr
1               5

<210> SEQ ID NO 23
<211> LENGTH: 11
<212> TYPE: PRT
<213> ORGANISM: Artificial Sequence
<220> FEATURE:
<223> OTHER INFORMATION: HFR4

<400> SEQUENCE: 23

Trp Gly Gln Gly Thr Leu Val Thr Val Ser Ser
1               5                   10

<210> SEQ ID NO 24
<211> LENGTH: 118
<212> TYPE: PRT
<213> ORGANISM: Artificial Sequence
<220> FEATURE:
<223> OTHER INFORMATION: HCVR

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Thr Ile His Trp Val Arg Gln Ala Pro Gly Gln Gly Leu Glu Trp Met
        35                  40                  45

Gly Trp Phe Tyr Pro Gly Ser His Ser Ile Lys Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Thr Arg His Gly Gly Tyr Asp Gly Phe Asp Tyr Trp Gly Gln Gly Thr
            100                 105                 110

Leu Val Thr Val Ser Ser
        115

<210> SEQ ID NO 25
<211> LENGTH: 23
<212> TYPE: PRT
<213> ORGANISM: Artificial Sequence
<220> FEATURE:
<223> OTHER INFORMATION: LFR1

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 26
<211> LENGTH: 17
<212> TYPE: PRT
<213> ORGANISM: Artificial Sequence
<220> FEATURE:
<223> OTHER INFORMATION: VL-CDR1

<400> SEQUENCE: 26

Lys Ser Ser Gln Ser Leu Phe Tyr Ser Thr Asn Gln Lys Asn Tyr Leu
1               5                   10                  15
```

Ala

<210> SEQ ID NO 27
<211> LENGTH: 15
<212> TYPE: PRT
<213> ORGANISM: Artificial Sequence
<220> FEATURE:
<223> OTHER INFORMATION: LFR2

<400> SEQUENCE: 27

Trp Tyr Gln Gln Lys Pro Gly Gln Pro Pro Lys Leu Leu Ile Tyr
1               5                   10                  15

<210> SEQ ID NO 28
<211> LENGTH: 7
<212> TYPE: PRT
<213> ORGANISM: Artificial Sequence
<220> FEATURE:
<223> OTHER INFORMATION: VL-CDR2

<400> SEQUENCE: 28

Trp Ala Ser Thr Arg Glu Ser
1               5

<210> SEQ ID NO 29
<211> LENGTH: 32
<212> TYPE: PRT
<213> ORGANISM: Artificial Sequence
<220> FEATURE:
<223> OTHER INFORMATION: LFR3

<400> SEQUENCE: 29

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 30
<211> LENGTH: 9
<212> TYPE: PRT
<213> ORGANISM: Artificial Sequence
<220> FEATURE:
<223> OTHER INFORMATION: VL-CDR3

<400> SEQUENCE: 30

Gln Gln Tyr Tyr Tyr Phe Pro Tyr Thr
1               5

<210> SEQ ID NO 31
<211> LENGTH: 10
<212> TYPE: PRT
<213> ORGANISM: Artificial Sequence
<220> FEATURE:
<223> OTHER INFORMATION: LFR4

<400> SEQUENCE: 31

Phe Gly Gln Gly Thr Lys Leu Glu Ile Lys
1               5                   10

<210> SEQ ID NO 32
<211> LENGTH: 113
<212> TYPE: PRT
<213> ORGANISM: Artificial Sequence
<220> FEATURE:
<223> OTHER INFORMATION: LCVR

<400> SEQUENCE: 32

-continued

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Tyr Ser
            20                  25                  30

Thr Asn Gln Lys Asn Tyr Leu Ala Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Tyr Phe Pro Tyr Thr Phe Gly Gln Gly Thr Lys Leu Glu Ile
            100                 105                 110

Lys
```

```
<210> SEQ ID NO 33
<211> LENGTH: 25
<212> TYPE: PRT
<213> ORGANISM: Artificial Sequence
<220> FEATURE:
<223> OTHER INFORMATION: HFR1

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser
            20                  25
```

```
<210> SEQ ID NO 34
<211> LENGTH: 10
<212> TYPE: PRT
<213> ORGANISM: Artificial Sequence
<220> FEATURE:
<223> OTHER INFORMATION: VH-CDR1

<400> SEQUENCE: 34

Gly Tyr Thr Phe Thr Asp Tyr Thr Ile His
1               5                   10
```

```
<210> SEQ ID NO 35
<211> LENGTH: 14
<212> TYPE: PRT
<213> ORGANISM: Artificial Sequence
<220> FEATURE:
<223> OTHER INFORMATION: HFR2

<400> SEQUENCE: 35

Trp Val Arg Gln Ala Pro Gly Gln Gly Leu Glu Trp Met Gly
1               5                   10
```

```
<210> SEQ ID NO 36
<211> LENGTH: 18
<212> TYPE: PRT
<213> ORGANISM: Artificial Sequence
<220> FEATURE:
<223> OTHER INFORMATION: VH-CDR2

<400> SEQUENCE: 36

Trp Phe Tyr Pro Gly Ser His Ser Ile Lys Tyr Ala Gln Lys Phe Gln
1               5                   10                  15
```

-continued

Gly Arg

<210> SEQ ID NO 37
<211> LENGTH: 31
<212> TYPE: PRT
<213> ORGANISM: Artificial Sequence
<220> FEATURE:
<223> OTHER INFORMATION: HFR3

<400> SEQUENCE: 37

Val Thr Ile Thr Ala Asp Lys Ser Thr Ser Thr Ala Tyr Met Glu Leu
1               5                   10                  15

Ser Ser Leu Arg Ser Glu Asp Thr Ala Val Tyr Tyr Cys Thr Arg
            20                  25                  30

<210> SEQ ID NO 38
<211> LENGTH: 9
<212> TYPE: PRT
<213> ORGANISM: Artificial Sequence
<220> FEATURE:
<223> OTHER INFORMATION: VH-CDR3

<400> SEQUENCE: 38

His Gly Gly Tyr Asp Gly Phe Asp Tyr
1               5

<210> SEQ ID NO 39
<211> LENGTH: 11
<212> TYPE: PRT
<213> ORGANISM: Artificial Sequence
<220> FEATURE:
<223> OTHER INFORMATION: HFR4

<400> SEQUENCE: 39

Trp Gly Gln Gly Thr Leu Val Thr Val Ser Ser
1               5                   10

<210> SEQ ID NO 40
<211> LENGTH: 118
<212> TYPE: PRT
<213> ORGANISM: Artificial Sequence
<220> FEATURE:
<223> OTHER INFORMATION: HCVR

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Thr Ile His Trp Val Arg Gln Ala Pro Gly Gln Gly Leu Glu Trp Met
        35                  40                  45

Gly Trp Phe Tyr Pro Gly Ser His Ser Ile Lys Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg His Gly Gly Tyr Asp Gly Phe Asp Tyr Trp Gly Gln Gly Thr
                100                 105                 110

Leu Val Thr Val Ser Ser
        115

```
<210> SEQ ID NO 41
<211> LENGTH: 23
<212> TYPE: PRT
<213> ORGANISM: Artificial Sequence
<220> FEATURE:
<223> OTHER INFORMATION: LFR1

<400> SEQUENCE: 41

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 42
<211> LENGTH: 17
<212> TYPE: PRT
<213> ORGANISM: Artificial Sequence
<220> FEATURE:
<223> OTHER INFORMATION: VL-CDR1

<400> SEQUENCE: 42

Lys Ser Ser Gln Ser Leu Phe Tyr Ser Thr Asn Gln Lys Asn Tyr Leu
1               5                   10                  15

Ala

<210> SEQ ID NO 43
<211> LENGTH: 15
<212> TYPE: PRT
<213> ORGANISM: Artificial Sequence
<220> FEATURE:
<223> OTHER INFORMATION: LFR2

<400> SEQUENCE: 43

Trp Tyr Gln Gln Lys Pro Gly Gln Pro Pro Lys Leu Leu Ile Tyr
1               5                   10                  15

<210> SEQ ID NO 44
<211> LENGTH: 7
<212> TYPE: PRT
<213> ORGANISM: Artificial Sequence
<220> FEATURE:
<223> OTHER INFORMATION: VL-CDR2

<400> SEQUENCE: 44

Trp Ala Ser Thr Arg Glu Ser
1               5

<210> SEQ ID NO 45
<211> LENGTH: 32
<212> TYPE: PRT
<213> ORGANISM: Artificial Sequence
<220> FEATURE:
<223> OTHER INFORMATION: LFR3

<400> SEQUENCE: 45

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
                20                  25                  30

<210> SEQ ID NO 46
<211> LENGTH: 9
<212> TYPE: PRT
<213> ORGANISM: Artificial Sequence
<220> FEATURE:
<223> OTHER INFORMATION: VL-CDR3
```

<400> SEQUENCE: 46

```
Gln Gln Tyr Tyr Tyr Phe Pro Tyr Thr
1               5
```

<210> SEQ ID NO 47
<211> LENGTH: 10
<212> TYPE: PRT
<213> ORGANISM: Artificial Sequence
<220> FEATURE:
<223> OTHER INFORMATION: LFR4

<400> SEQUENCE: 47

```
Phe Gly Gln Gly Thr Lys Leu Glu Ile Lys
1               5                   10
```

<210> SEQ ID NO 48
<211> LENGTH: 113
<212> TYPE: PRT
<213> ORGANISM: Artificial Sequence
<220> FEATURE:
<223> OTHER INFORMATION: LCVR

<400> SEQUENCE: 48

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Tyr Ser
            20                  25                  30

Thr Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Tyr Phe Pro Tyr Thr Phe Gly Gln Gly Thr Lys Leu Glu Ile
                100                 105                 110

Lys
```

<210> SEQ ID NO 49
<211> LENGTH: 25
<212> TYPE: PRT
<213> ORGANISM: Artificial Sequence
<220> FEATURE:
<223> OTHER INFORMATION: HFR1

<400> SEQUENCE: 49

```
Gln Val Gln Leu Val Gln Ser Gly Ala Glu Val Lys Lys Pro Gly Ser
1               5                   10                  15

Ser Val Lys Val Ser Cys Lys Ala Ser
            20                  25
```

<210> SEQ ID NO 50
<211> LENGTH: 10
<212> TYPE: PRT
<213> ORGANISM: Artificial Sequence
<220> FEATURE:
<223> OTHER INFORMATION: VH-CDR1

<400> SEQUENCE: 50

```
Gly Tyr Thr Phe Thr Asp Tyr Thr Ile His
```

-continued

```
1               5                    10
```

<210> SEQ ID NO 51
<211> LENGTH: 14
<212> TYPE: PRT
<213> ORGANISM: Artificial Sequence
<220> FEATURE:
<223> OTHER INFORMATION: HFR2

<400> SEQUENCE: 51

```
Trp Val Arg Gln Ala Pro Gly Gln Gly Leu Glu Trp Met Gly
1               5                    10
```

<210> SEQ ID NO 52
<211> LENGTH: 18
<212> TYPE: PRT
<213> ORGANISM: Artificial Sequence
<220> FEATURE:
<223> OTHER INFORMATION: VH-CDR2

<400> SEQUENCE: 52

```
Trp Phe Tyr Pro Gly Ser His Ser Ile Lys Tyr Ala Gln Lys Phe Gln
1               5                    10                    15

Gly Arg
```

<210> SEQ ID NO 53
<211> LENGTH: 31
<212> TYPE: PRT
<213> ORGANISM: Artificial Sequence
<220> FEATURE:
<223> OTHER INFORMATION: HFR3

<400> SEQUENCE: 53

```
Val Thr Ile Thr Ala Asp Lys Ser Thr Ser Thr Ala Tyr Met Glu Leu
1               5                    10                    15

Ser Ser Leu Arg Ser Glu Asp Thr Ala Val Tyr Tyr Cys Ala Arg
           20                    25                    30
```

<210> SEQ ID NO 54
<211> LENGTH: 9
<212> TYPE: PRT
<213> ORGANISM: Artificial Sequence
<220> FEATURE:
<223> OTHER INFORMATION: VH-CDR3

<400> SEQUENCE: 54

```
His Gly Gly Tyr Asp Gly Phe Asp Tyr
1               5
```

<210> SEQ ID NO 55
<211> LENGTH: 11
<212> TYPE: PRT
<213> ORGANISM: Artificial Sequence
<220> FEATURE:
<223> OTHER INFORMATION: HFR4

<400> SEQUENCE: 55

```
Trp Gly Gln Gly Thr Leu Val Thr Val Ser Ser
1               5                    10
```

<210> SEQ ID NO 56
<211> LENGTH: 118
<212> TYPE: PRT
<213> ORGANISM: Artificial Sequence
<220> FEATURE:
<223> OTHER INFORMATION: HCVR

<400> SEQUENCE: 56

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Thr Ile His Trp Val Arg Gln Ala Pro Gly Gln Gly Leu Glu Trp Met
        35                  40                  45

Gly Trp Phe Tyr Pro Gly Ser His Ser Ile Lys Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Asp Gly Phe Asp Tyr Trp Gly Gln Gly Thr
            100                 105                 110

Leu Val Thr Val Ser Ser
        115
```

<210> SEQ ID NO 57
<211> LENGTH: 23
<212> TYPE: PRT
<213> ORGANISM: Artificial Sequence
<220> FEATURE:
<223> OTHER INFORMATION: LFR1

<400> SEQUENCE: 57

```
Asp Ile Val Met Thr Gln Ser Pro Asp Ser Leu Ala Val Ser Leu Gly
1               5                   10                  15

Glu Arg Ala Thr Ile Asn Cys
            20
```

<210> SEQ ID NO 58
<211> LENGTH: 17
<212> TYPE: PRT
<213> ORGANISM: Artificial Sequence
<220> FEATURE:
<223> OTHER INFORMATION: VL-CDR1

<400> SEQUENCE: 58

```
Lys Ser Ser Gln Ser Leu Phe Tyr Ser Thr Asn Gln Lys Asn Tyr Leu
1               5                   10                  15

Ala
```

<210> SEQ ID NO 59
<211> LENGTH: 15
<212> TYPE: PRT
<213> ORGANISM: Artificial Sequence
<220> FEATURE:
<223> OTHER INFORMATION: LFR2

<400> SEQUENCE: 59

```
Trp Tyr Gln Gln Lys Pro Gly Gln Pro Pro Lys Leu Leu Ile Tyr
1               5                   10                  15
```

<210> SEQ ID NO 60
<211> LENGTH: 7
<212> TYPE: PRT
<213> ORGANISM: Artificial Sequence
<220> FEATURE:
<223> OTHER INFORMATION: VL-CDR2

```
<400> SEQUENCE: 60

Trp Ala Ser Thr Arg Glu Ser
1               5

<210> SEQ ID NO 61
<211> LENGTH: 32
<212> TYPE: PRT
<213> ORGANISM: Artificial Sequence
<220> FEATURE:
<223> OTHER INFORMATION: LFR3

<400> SEQUENCE: 61

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 62
<211> LENGTH: 9
<212> TYPE: PRT
<213> ORGANISM: Artificial Sequence
<220> FEATURE:
<223> OTHER INFORMATION: VL-CDR3

<400> SEQUENCE: 62

Gln Gln Tyr Tyr Tyr Phe Pro Tyr Thr
1               5

<210> SEQ ID NO 63
<211> LENGTH: 10
<212> TYPE: PRT
<213> ORGANISM: Artificial Sequence
<220> FEATURE:
<223> OTHER INFORMATION: LFR4

<400> SEQUENCE: 63

Phe Gly Gln Gly Thr Lys Leu Glu Ile Lys
1               5                   10

<210> SEQ ID NO 64
<211> LENGTH: 113
<212> TYPE: PRT
<213> ORGANISM: Artificial Sequence
<220> FEATURE:
<223> OTHER INFORMATION: LCVR

<400> SEQUENCE: 64

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Tyr Ser
            20                  25                  30

Thr Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Tyr Phe Pro Tyr Thr Phe Gly Gln Gly Thr Lys Leu Glu Ile
            100                 105                 110

Lys
```

-continued

```
<210> SEQ ID NO 65
<211> LENGTH: 25
<212> TYPE: PRT
<213> ORGANISM: Artificial Sequence
<220> FEATURE:
<223> OTHER INFORMATION: HFR1

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 66
<211> LENGTH: 10
<212> TYPE: PRT
<213> ORGANISM: Artificial Sequence
<220> FEATURE:
<223> OTHER INFORMATION: VH-CDR1

<400> SEQUENCE: 66

Gly Tyr Thr Phe Thr Glu Tyr Thr Ile His
1               5                   10

<210> SEQ ID NO 67
<211> LENGTH: 14
<212> TYPE: PRT
<213> ORGANISM: Artificial Sequence
<220> FEATURE:
<223> OTHER INFORMATION: HFR2

<400> SEQUENCE: 67

Trp Val Arg Gln Ala Pro Gly Gln Gly Leu Glu Trp Met Gly
1               5                   10

<210> SEQ ID NO 68
<211> LENGTH: 17
<212> TYPE: PRT
<213> ORGANISM: Artificial Sequence
<220> FEATURE:
<223> OTHER INFORMATION: VH-CDR2

<400> SEQUENCE: 68

Trp Phe Tyr Pro Gly Ser Gly Ser Thr Glu Tyr Ala Gln Lys Phe Gln
1               5                   10                  15

Gly

<210> SEQ ID NO 69
<211> LENGTH: 32
<212> TYPE: PRT
<213> ORGANISM: Artificial Sequence
<220> FEATURE:
<223> OTHER INFORMATION: HFR3

<400> SEQUENCE: 69

Arg Val Thr Met Thr Ala Asp Thr Ser Ile Ser Thr Ala Tyr Met Glu
1               5                   10                  15

Leu Ser Arg Leu Arg Ser Asp Asp Thr Ala Val Tyr Phe Cys Glu Arg
            20                  25                  30

<210> SEQ ID NO 70
<211> LENGTH: 9
<212> TYPE: PRT
<213> ORGANISM: Artificial Sequence
```

```
<220> FEATURE:
<223> OTHER INFORMATION: VH-CDR3

<400> SEQUENCE: 70

His Gly Gly Tyr Asp Gly Phe Asp Tyr
1               5

<210> SEQ ID NO 71
<211> LENGTH: 11
<212> TYPE: PRT
<213> ORGANISM: Artificial Sequence
<220> FEATURE:
<223> OTHER INFORMATION: HFR4

<400> SEQUENCE: 71

Trp Gly Gln Gly Thr Thr Val Thr Val Ser Ser
1               5                   10

<210> SEQ ID NO 72
<211> LENGTH: 118
<212> TYPE: PRT
<213> ORGANISM: Artificial Sequence
<220> FEATURE:
<223> OTHER INFORMATION: HCVR

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Ile His Trp Val Arg Gln Ala Pro Gly Gln Gly Leu Glu Trp Met
            35                  40                  45

Gly Trp Phe Tyr Pro Gly Ser Gly Ser Thr Glu Tyr Ala Gln Lys Phe
        50                  55                  60

Gln Gly Arg Val Thr Met Thr Ala Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Glu Arg His Gly Gly Tyr Asp Gly Phe Asp Tyr Trp Gly Gln Gly Thr
            100                 105                 110

Thr Val Thr Val Ser Ser
        115

<210> SEQ ID NO 73
<211> LENGTH: 23
<212> TYPE: PRT
<213> ORGANISM: Artificial Sequence
<220> FEATURE:
<223> OTHER INFORMATION: LFR1

<400> SEQUENCE: 73

Asp Ile Val Met Thr Gln Ser Pro Asp Ser Leu Ala Val Ser Leu Gly
1               5                   10                  15

Glu Arg Ala Thr Ile Asn Cys
                20

<210> SEQ ID NO 74
<211> LENGTH: 17
<212> TYPE: PRT
<213> ORGANISM: Artificial Sequence
<220> FEATURE:
<223> OTHER INFORMATION: VL-CDR1
```

<400> SEQUENCE: 74

Lys Ser Ser Gln Ser Leu Leu Tyr Ser Asn Asn Gln Lys Asn Tyr Leu
1               5                   10                  15

Ala

<210> SEQ ID NO 75
<211> LENGTH: 15
<212> TYPE: PRT
<213> ORGANISM: Artificial Sequence
<220> FEATURE:
<223> OTHER INFORMATION: LFR2

<400> SEQUENCE: 75

Trp Tyr Gln Gln Lys Pro Gly Gln Pro Pro Lys Leu Leu Ile Tyr
1               5                   10                  15

<210> SEQ ID NO 76
<211> LENGTH: 7
<212> TYPE: PRT
<213> ORGANISM: Artificial Sequence
<220> FEATURE:
<223> OTHER INFORMATION: VL-CDR2

<400> SEQUENCE: 76

Trp Ala Ser Thr Arg Gly Ser
1               5

<210> SEQ ID NO 77
<211> LENGTH: 32
<212> TYPE: PRT
<213> ORGANISM: Artificial Sequence
<220> FEATURE:
<223> OTHER INFORMATION: LFR3

<400> SEQUENCE: 77

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 78
<211> LENGTH: 9
<212> TYPE: PRT
<213> ORGANISM: Artificial Sequence
<220> FEATURE:
<223> OTHER INFORMATION: VL-CDR3

<400> SEQUENCE: 78

Gln Gln Tyr Tyr Ser Tyr Pro Phe Thr
1               5

<210> SEQ ID NO 79
<211> LENGTH: 10
<212> TYPE: PRT
<213> ORGANISM: Artificial Sequence
<220> FEATURE:
<223> OTHER INFORMATION: LFR4

<400> SEQUENCE: 79

Phe Gly Gly Gly Thr Lys Val Glu Ile Lys
1               5                   10

<210> SEQ ID NO 80
<211> LENGTH: 113
<212> TYPE: PRT

-continued

<213> ORGANISM: Artificial Sequence
<220> FEATURE:
<223> OTHER INFORMATION: LCVR

<400> SEQUENCE: 80

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
                20                  25                  30

Asn Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Gly Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Phe Thr Phe Gly Gly Gly Thr Lys Val Glu Ile
            100                 105                 110

Lys
```

<210> SEQ ID NO 81
<211> LENGTH: 25
<212> TYPE: PRT
<213> ORGANISM: Artificial Sequence
<220> FEATURE:
<223> OTHER INFORMATION: HFR1

<400> SEQUENCE: 81

```
Gln Val Gln Leu Val Gln Ser Gly Ala Glu Val Lys Lys Pro Gly Ser
1               5                   10                  15

Ser Val Lys Val Ser Cys Lys Ala Ser
            20                  25
```

<210> SEQ ID NO 82
<211> LENGTH: 10
<212> TYPE: PRT
<213> ORGANISM: Artificial Sequence
<220> FEATURE:
<223> OTHER INFORMATION: VH-CDR1

<400> SEQUENCE: 82

```
Gly Tyr Thr Phe Thr Glu Tyr Thr Ile His
1               5                   10
```

<210> SEQ ID NO 83
<211> LENGTH: 14
<212> TYPE: PRT
<213> ORGANISM: Artificial Sequence
<220> FEATURE:
<223> OTHER INFORMATION: HFR2

<400> SEQUENCE: 83

```
Trp Val Arg Gln Ala Pro Gly Gln Gly Leu Glu Trp Met Gly
1               5                   10
```

<210> SEQ ID NO 84
<211> LENGTH: 17
<212> TYPE: PRT
<213> ORGANISM: Artificial Sequence
<220> FEATURE:
<223> OTHER INFORMATION: VH-CDR2

```
<400> SEQUENCE: 84

Trp Phe Tyr Pro Gly Ser Gly Ser Ala Glu Tyr Ala Gln Lys Phe Gln
1               5                   10                  15

Gly

<210> SEQ ID NO 85
<211> LENGTH: 32
<212> TYPE: PRT
<213> ORGANISM: Artificial Sequence
<220> FEATURE:
<223> OTHER INFORMATION: HFR3

<400> SEQUENCE: 85

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Glu Arg
            20                  25                  30

<210> SEQ ID NO 86
<211> LENGTH: 9
<212> TYPE: PRT
<213> ORGANISM: Artificial Sequence
<220> FEATURE:
<223> OTHER INFORMATION: VH-CDR3

<400> SEQUENCE: 86

His Gly Gly Tyr Asp Gly Phe Asp Tyr
1               5

<210> SEQ ID NO 87
<211> LENGTH: 11
<212> TYPE: PRT
<213> ORGANISM: Artificial Sequence
<220> FEATURE:
<223> OTHER INFORMATION: HFR4

<400> SEQUENCE: 87

Trp Gly Gln Gly Thr Thr Val Thr Val Ser Ser
1               5                   10

<210> SEQ ID NO 88
<211> LENGTH: 118
<212> TYPE: PRT
<213> ORGANISM: Artificial Sequence
<220> FEATURE:
<223> OTHER INFORMATION: HCVR

<400> SEQUENCE: 88

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Gln Gly Leu Glu Trp Met
        35                  40                  45

Gly Trp Phe Tyr Pro Gly Ser Gly Ser Ala Glu Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Arg His Gly Gly Tyr Asp Gly Phe Asp Tyr Trp Gly Gln Gly Thr
            100                 105                 110
```

-continued

```
Thr Val Thr Val Ser Ser
        115

<210> SEQ ID NO 89
<211> LENGTH: 23
<212> TYPE: PRT
<213> ORGANISM: Artificial Sequence
<220> FEATURE:
<223> OTHER INFORMATION: LFR1

<400> SEQUENCE: 89

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 90
<211> LENGTH: 17
<212> TYPE: PRT
<213> ORGANISM: Artificial Sequence
<220> FEATURE:
<223> OTHER INFORMATION: VL-CDR1

<400> SEQUENCE: 90

Lys Ser Ser Gln Ser Leu Leu Tyr Ser Asn Asn Gln Lys Asn Tyr Leu
1               5                   10                  15

Ala

<210> SEQ ID NO 91
<211> LENGTH: 15
<212> TYPE: PRT
<213> ORGANISM: Artificial Sequence
<220> FEATURE:
<223> OTHER INFORMATION: LFR2

<400> SEQUENCE: 91

Trp Tyr Gln Gln Lys Pro Gly Gln Pro Pro Lys Leu Leu Ile Tyr
1               5                   10                  15

<210> SEQ ID NO 92
<211> LENGTH: 7
<212> TYPE: PRT
<213> ORGANISM: Artificial Sequence
<220> FEATURE:
<223> OTHER INFORMATION: VL-CDR2

<400> SEQUENCE: 92

Trp Ala Ser Thr Arg Gly Ser
1               5

<210> SEQ ID NO 93
<211> LENGTH: 32
<212> TYPE: PRT
<213> ORGANISM: Artificial Sequence
<220> FEATURE:
<223> OTHER INFORMATION: LFR3

<400> SEQUENCE: 93

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 94
```

-continued

```
<211> LENGTH: 9
<212> TYPE: PRT
<213> ORGANISM: Artificial Sequence
<220> FEATURE:
<223> OTHER INFORMATION: VL-CDR3

<400> SEQUENCE: 94

Gln Gln Tyr Tyr Ser Tyr Pro Phe Thr
1               5

<210> SEQ ID NO 95
<211> LENGTH: 10
<212> TYPE: PRT
<213> ORGANISM: Artificial Sequence
<220> FEATURE:
<223> OTHER INFORMATION: LFR4

<400> SEQUENCE: 95

Phe Gly Gly Gly Thr Lys Val Glu Ile Lys
1               5                   10

<210> SEQ ID NO 96
<211> LENGTH: 113
<212> TYPE: PRT
<213> ORGANISM: Artificial Sequence
<220> FEATURE:
<223> OTHER INFORMATION: LCVR

<400> SEQUENCE: 96

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
                20                  25                  30

Asn Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Gly Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Phe Thr Phe Gly Gly Gly Thr Lys Val Glu Ile
            100                 105                 110

Lys

<210> SEQ ID NO 97
<211> LENGTH: 25
<212> TYPE: PRT
<213> ORGANISM: Artificial Sequence
<220> FEATURE:
<223> OTHER INFORMATION: HFR1

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Ala Ser
                20                  25

<210> SEQ ID NO 98
<211> LENGTH: 10
<212> TYPE: PRT
<213> ORGANISM: Artificial Sequence
<220> FEATURE:
```

<223> OTHER INFORMATION: VH-CDR1

<400> SEQUENCE: 98

Gly Tyr Thr Phe Thr Glu Tyr Thr Ile His
1               5                   10

<210> SEQ ID NO 99
<211> LENGTH: 14
<212> TYPE: PRT
<213> ORGANISM: Artificial Sequence
<220> FEATURE:
<223> OTHER INFORMATION: HFR2

<400> SEQUENCE: 99

Trp Val Arg Gln Ala Pro Gly Gln Gly Leu Glu Trp Met Gly
1               5                   10

<210> SEQ ID NO 100
<211> LENGTH: 17
<212> TYPE: PRT
<213> ORGANISM: Artificial Sequence
<220> FEATURE:
<223> OTHER INFORMATION: VH-CDR2

<400> SEQUENCE: 100

Trp Phe Tyr Pro Gly Ser Gly Ser Thr Glu Tyr Ala Gln Lys Phe Gln
1               5                   10                  15

Gly

<210> SEQ ID NO 101
<211> LENGTH: 32
<212> TYPE: PRT
<213> ORGANISM: Artificial Sequence
<220> FEATURE:
<223> OTHER INFORMATION: HFR3

<400> SEQUENCE: 101

Arg Val Thr Met Thr Ala Asp Thr Ser Thr Ser Thr Val Tyr Met Glu
1               5                   10                  15

Leu Ser Ser Leu Arg Ser Glu Asp Thr Ala Val Tyr Tyr Cys Glu Arg
            20                  25                  30

<210> SEQ ID NO 102
<211> LENGTH: 9
<212> TYPE: PRT
<213> ORGANISM: Artificial Sequence
<220> FEATURE:
<223> OTHER INFORMATION: VH-CDR3

<400> SEQUENCE: 102

His Gly Gly Tyr Asp Gly Phe Asp Tyr
1               5

<210> SEQ ID NO 103
<211> LENGTH: 11
<212> TYPE: PRT
<213> ORGANISM: Artificial Sequence
<220> FEATURE:
<223> OTHER INFORMATION: HFR4

<400> SEQUENCE: 103

Trp Gly Gln Gly Thr Thr Val Thr Val Ser Ser
1               5                   10

<210> SEQ ID NO 104

<211> LENGTH: 118
<212> TYPE: PRT
<213> ORGANISM: Artificial Sequence
<220> FEATURE:
<223> OTHER INFORMATION: HCVR

<400> SEQUENCE: 104

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Gln Gly Leu Glu Trp Met
        35                  40                  45

Gly Trp Phe Tyr Pro Gly Ser Gly Ser Thr Glu Tyr Ala Gln Lys Phe
    50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Glu Arg His Gly Gly Tyr Asp Gly Phe Asp Tyr Trp Gly Gln Gly Thr
            100                 105                 110

Thr Val Thr Val Ser Ser
        115
```

<210> SEQ ID NO 105
<211> LENGTH: 23
<212> TYPE: PRT
<213> ORGANISM: Artificial Sequence
<220> FEATURE:
<223> OTHER INFORMATION: LFR1

<400> SEQUENCE: 105

```
Asp Ile Val Met Thr Gln Ser Pro Asp Ser Leu Ala Val Ser Leu Gly
1               5                   10                  15

Glu Arg Ala Thr Ile Asn Cys
            20
```

<210> SEQ ID NO 106
<211> LENGTH: 17
<212> TYPE: PRT
<213> ORGANISM: Artificial Sequence
<220> FEATURE:
<223> OTHER INFORMATION: VL-CDR1

<400> SEQUENCE: 106

```
Lys Ser Ser Gln Ser Leu Leu Tyr Ser Asn Asn Gln Lys Asn Tyr Leu
1               5                   10                  15

Ala
```

<210> SEQ ID NO 107
<211> LENGTH: 15
<212> TYPE: PRT
<213> ORGANISM: Artificial Sequence
<220> FEATURE:
<223> OTHER INFORMATION: LFR2

<400> SEQUENCE: 107

```
Trp Tyr Gln Gln Lys Pro Gly Gln Pro Pro Lys Leu Leu Ile Tyr
1               5                   10                  15
```

<210> SEQ ID NO 108
<211> LENGTH: 7

```
<212> TYPE: PRT
<213> ORGANISM: Artificial Sequence
<220> FEATURE:
<223> OTHER INFORMATION: VL-CDR2

<400> SEQUENCE: 108

Trp Ala Ser Thr Arg Gly Ser
1               5

<210> SEQ ID NO 109
<211> LENGTH: 32
<212> TYPE: PRT
<213> ORGANISM: Artificial Sequence
<220> FEATURE:
<223> OTHER INFORMATION: LFR3

<400> SEQUENCE: 109

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 110
<211> LENGTH: 9
<212> TYPE: PRT
<213> ORGANISM: Artificial Sequence
<220> FEATURE:
<223> OTHER INFORMATION: VL-CDR3

<400> SEQUENCE: 110

Gln Gln Tyr Tyr Ser Tyr Pro Phe Thr
1               5

<210> SEQ ID NO 111
<211> LENGTH: 10
<212> TYPE: PRT
<213> ORGANISM: Artificial Sequence
<220> FEATURE:
<223> OTHER INFORMATION: LFR4

<400> SEQUENCE: 111

Phe Gly Gly Gly Thr Lys Val Glu Ile Lys
1               5                   10

<210> SEQ ID NO 112
<211> LENGTH: 113
<212> TYPE: PRT
<213> ORGANISM: Artificial Sequence
<220> FEATURE:
<223> OTHER INFORMATION: LCVR

<400> SEQUENCE: 112

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Asn Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Gly Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

```
Tyr Tyr Ser Tyr Pro Phe Thr Phe Gly Gly Gly Thr Lys Val Glu Ile
            100             105             110

Lys

<210> SEQ ID NO 113
<211> LENGTH: 25
<212> TYPE: PRT
<213> ORGANISM: Artificial Sequence
<220> FEATURE:
<223> OTHER INFORMATION: HFR1

<400> SEQUENCE: 113

Glu Val Gln Leu Val Gln Ser Gly Ala Glu Val Lys Lys Pro Gly Glu
1               5               10              15

Ser Leu Lys Ile Ser Cys Lys Gly Ser
            20              25

<210> SEQ ID NO 114
<211> LENGTH: 10
<212> TYPE: PRT
<213> ORGANISM: Artificial Sequence
<220> FEATURE:
<223> OTHER INFORMATION: VH-CDR1

<400> SEQUENCE: 114

Gly Tyr Thr Phe Thr Glu Tyr Thr Ile His
1               5               10

<210> SEQ ID NO 115
<211> LENGTH: 14
<212> TYPE: PRT
<213> ORGANISM: Artificial Sequence
<220> FEATURE:
<223> OTHER INFORMATION: HFR2

<400> SEQUENCE: 115

Trp Val Arg Gln Met Pro Gly Lys Gly Leu Glu Trp Met Gly
1               5               10

<210> SEQ ID NO 116
<211> LENGTH: 17
<212> TYPE: PRT
<213> ORGANISM: Artificial Sequence
<220> FEATURE:
<223> OTHER INFORMATION: VH-CDR2

<400> SEQUENCE: 116

Trp Phe Tyr Pro Gly Ser Gly Ser Thr Glu Tyr Ser Pro Ser Phe Gln
1               5               10              15

Gly

<210> SEQ ID NO 117
<211> LENGTH: 32
<212> TYPE: PRT
<213> ORGANISM: Artificial Sequence
<220> FEATURE:
<223> OTHER INFORMATION: HFR3

<400> SEQUENCE: 117

Gln Val Thr Ile Ser Ala Asp Lys Ser Ile Ser Thr Ala Tyr Leu Gln
1               5               10              15

Trp Ser Ser Leu Lys Ala Ser Asp Thr Ala Met Tyr Tyr Cys Glu Arg
            20              25              30
```

<210> SEQ ID NO 118
<211> LENGTH: 9
<212> TYPE: PRT
<213> ORGANISM: Artificial Sequence
<220> FEATURE:
<223> OTHER INFORMATION: VH-CDR3

<400> SEQUENCE: 118

His Gly Gly Tyr Asp Gly Phe Asp Tyr
1               5

<210> SEQ ID NO 119
<211> LENGTH: 11
<212> TYPE: PRT
<213> ORGANISM: Artificial Sequence
<220> FEATURE:
<223> OTHER INFORMATION: HFR4

<400> SEQUENCE: 119

Trp Gly Gln Gly Thr Thr Val Thr Val Ser Ser
1               5                   10

<210> SEQ ID NO 120
<211> LENGTH: 118
<212> TYPE: PRT
<213> ORGANISM: Artificial Sequence
<220> FEATURE:
<223> OTHER INFORMATION: HCVR

<400> SEQUENCE: 120

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Glu Tyr
                20                  25                  30

Thr Ile His Trp Val Arg Gln Met Pro Gly Lys Gly Leu Glu Trp Met
            35                  40                  45

Gly Trp Phe Tyr Pro Gly Ser Gly Ser Thr Glu Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Glu Arg His Gly Gly Tyr Asp Gly Phe Asp Tyr Trp Gly Gln Gly Thr
            100                 105                 110

Thr Val Thr Val Ser Ser
        115

<210> SEQ ID NO 121
<211> LENGTH: 23
<212> TYPE: PRT
<213> ORGANISM: Artificial Sequence
<220> FEATURE:
<223> OTHER INFORMATION: LFR1

<400> SEQUENCE: 121

Asp Ile Val Met Thr Gln Ser Pro Asp Ser Leu Ala Val Ser Leu Gly
1               5                   10                  15

Glu Arg Ala Thr Ile Asn Cys
                20

<210> SEQ ID NO 122
<211> LENGTH: 17

```
<212> TYPE: PRT
<213> ORGANISM: Artificial Sequence
<220> FEATURE:
<223> OTHER INFORMATION: VL-CDR1

<400> SEQUENCE: 122

Lys Ser Ser Gln Ser Leu Leu Tyr Ser Asn Asn Gln Lys Asn Tyr Leu
1               5                   10                  15

Ala

<210> SEQ ID NO 123
<211> LENGTH: 15
<212> TYPE: PRT
<213> ORGANISM: Artificial Sequence
<220> FEATURE:
<223> OTHER INFORMATION: LFR2

<400> SEQUENCE: 123

Trp Tyr Gln Gln Lys Pro Gly Gln Pro Pro Lys Leu Leu Ile Tyr
1               5                   10                  15

<210> SEQ ID NO 124
<211> LENGTH: 7
<212> TYPE: PRT
<213> ORGANISM: Artificial Sequence
<220> FEATURE:
<223> OTHER INFORMATION: VL-CDR2

<400> SEQUENCE: 124

Trp Ala Ser Thr Arg Gly Ser
1               5

<210> SEQ ID NO 125
<211> LENGTH: 32
<212> TYPE: PRT
<213> ORGANISM: Artificial Sequence
<220> FEATURE:
<223> OTHER INFORMATION: LFR3

<400> SEQUENCE: 125

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 126
<211> LENGTH: 9
<212> TYPE: PRT
<213> ORGANISM: Artificial Sequence
<220> FEATURE:
<223> OTHER INFORMATION: VL-CDR3

<400> SEQUENCE: 126

Gln Gln Tyr Tyr Ser Tyr Pro Phe Thr
1               5

<210> SEQ ID NO 127
<211> LENGTH: 10
<212> TYPE: PRT
<213> ORGANISM: Artificial Sequence
<220> FEATURE:
<223> OTHER INFORMATION: LFR4

<400> SEQUENCE: 127

Phe Gly Gly Gly Thr Lys Val Glu Ile Lys
1               5                   10
```

```
<210> SEQ ID NO 128
<211> LENGTH: 113
<212> TYPE: PRT
<213> ORGANISM: Artificial Sequence
<220> FEATURE:
<223> OTHER INFORMATION: LCVR

<400> SEQUENCE: 128

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Asn Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Gly Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Phe Thr Phe Gly Gly Gly Thr Lys Val Glu Ile
            100                 105                 110

Lys

<210> SEQ ID NO 129
<211> LENGTH: 118
<212> TYPE: PRT
<213> ORGANISM: Artificial Sequence
<220> FEATURE:
<223> OTHER INFORMATION: HCVR

<400> SEQUENCE: 129

Lys Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asp Tyr
            20                  25                  30

Thr Ile His Trp Val Lys Gln Arg Ser Gly Gln Gly Leu Glu Trp Ile
        35                  40                  45

Gly Trp Phe Tyr Pro Gly Ser His Ser Ile Lys Tyr Asn Glu Gln Phe
        50                  55                  60

Lys Asp Arg Ala Thr Leu Thr Ala Asp Lys Ser Ser Ser Thr Val Tyr
65                  70                  75                  80

Met Glu Leu Ser Arg Leu Thr Ser Glu Asp Ser Ala Val Tyr Phe Cys
                85                  90                  95

Thr Arg His Gly Gly Tyr Asp Gly Phe Asp Tyr Trp Gly Gln Gly Thr
            100                 105                 110

Thr Leu Thr Val Ser Ser
        115

<210> SEQ ID NO 130
<211> LENGTH: 113
<212> TYPE: PRT
<213> ORGANISM: Artificial Sequence
<220> FEATURE:
<223> OTHER INFORMATION: LCVR

<400> SEQUENCE: 130

Asp Ile Val Met Ser Gln Ser Pro Ser Ser Leu Ala Val Ser Val Gly
```

-continued

```
1               5                   10                  15

Glu Lys Ile Thr Met Ser Cys Lys Ser Ser Gln Ser Leu Phe Tyr Ser
            20                  25                  30

Thr Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Tyr Phe Pro Tyr Thr Phe Gly Gly Gly Thr Lys Leu Glu Ile
                100                 105                 110

Lys
```

```
<210> SEQ ID NO 131
<211> LENGTH: 118
<212> TYPE: PRT
<213> ORGANISM: Artificial Sequence
<220> FEATURE:
<223> OTHER INFORMATION: HCVR

<400> SEQUENCE: 131

Lys Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Glu Tyr
            20                  25                  30

Thr Ile His Trp Val Lys Gln Arg Ser Gly Gln Gly Leu Glu Trp Ile
        35                  40                  45

Gly Trp Phe Tyr Pro Gly Ser Gly Ser Met Glu Tyr Asn Glu Lys Phe
    50                  55                  60

Lys Asp Lys Ala Thr Leu Thr Ala Asp Asn Ser Ser Ser Thr Val Tyr
65                  70                  75                  80

Met Glu Leu Ser Arg Leu Thr Ser Glu Asp Ser Ala Val Tyr Phe Cys
                85                  90                  95

Glu Arg His Gly Gly Tyr Asp Gly Phe Asp Tyr Trp Gly Gln Gly Thr
                100                 105                 110

Thr Leu Thr Val Ser Ser
        115
```

```
<210> SEQ ID NO 132
<211> LENGTH: 113
<212> TYPE: PRT
<213> ORGANISM: Artificial Sequence
<220> FEATURE:
<223> OTHER INFORMATION: LCVR

<400> SEQUENCE: 132

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Asn Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Gly Ser Gly Val
    50                  55                  60

Pro Asp Arg Phe Thr Gly Ser Gly Ser Gly Thr Asp Phe Thr Leu Thr
```

```
65                    70                   75                   80

Ile Ser Ser Val Lys Ala Glu Asp Leu Ala Ile Tyr Tyr Cys Gln Gln
                    85                   90                   95

Tyr Tyr Ser Tyr Pro Phe Thr Phe Gly Gly Gly Thr Lys Leu Glu Ile
                    100                  105                  110

Lys

<210> SEQ ID NO 133
<211> LENGTH: 118
<212> TYPE: PRT
<213> ORGANISM: Artificial Sequence
<220> FEATURE:
<223> OTHER INFORMATION: HCVR

<400> SEQUENCE: 133

Gln Val Gln Leu Val Gln Ser Gly Ala Glu Val Lys Lys Pro Gly Ala
1                   5                    10                   15

Ser Val Lys Val Ser Cys Lys Ala Ser Gly Tyr Thr Phe Thr Glu Tyr
                    20                   25                   30

Thr Ile His Trp Val Arg Gln Ala Pro Gly Gln Gly Leu Glu Trp Ile
          35                   40                   45

Gly Trp Phe Tyr Pro Gly Ser Gly Ser Thr Glu Tyr Ala Glu Lys Phe
    50                   55                   60

Gln Gly Arg Ala Thr Met Thr Ala Asp Asn Ser Ile Ser Thr Val Tyr
65                   70                   75                   80

Met Glu Leu Ser Arg Leu Arg Ser Asp Asp Thr Ala Val Tyr Phe Cys
                    85                   90                   95

Glu Arg His Gly Gly Tyr Asp Gly Phe Asp Tyr Trp Gly Gln Gly Thr
                    100                  105                  110

Thr Leu Thr Val Ser Ser
          115

<210> SEQ ID NO 134
<211> LENGTH: 113
<212> TYPE: PRT
<213> ORGANISM: Artificial Sequence
<220> FEATURE:
<223> OTHER INFORMATION: LCVR

<400> SEQUENCE: 134

Asp Ile Val Met Ser Gln Ser Pro Asp Ser Leu Ala Val Ser Val Gly
1                   5                    10                   15

Glu Arg Ala Thr Ile Ser Cys Lys Ser Ser Gln Ser Leu Leu Tyr Ser
                    20                   25                   30

Asn Asn Gln Lys Asn Tyr Leu Ala Trp Tyr Gln Gln Lys Pro Gly Gln
          35                   40                   45

Ser Pro Lys Leu Leu Ile Tyr Trp Ala Ser Thr Arg Gly Ser Gly Val
    50                   55                   60

Pro Asp Arg Phe Ser Gly Ser Gly Ser Gly Thr Asp Phe Thr Leu Thr
65                   70                   75                   80

Ile Ser Ser Leu Gln Ala Glu Asp Val Ala Ile Tyr Tyr Cys Gln Gln
                    85                   90                   95

Tyr Tyr Ser Tyr Pro Phe Thr Phe Gly Gly Gly Thr Lys Leu Glu Ile
                    100                  105                  110

Lys

<210> SEQ ID NO 135
```

```
<211> LENGTH: 118
<212> TYPE: PRT
<213> ORGANISM: Artificial Sequence
<220> FEATURE:
<223> OTHER INFORMATION: HCVR

<400> SEQUENCE: 135

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Ile His Trp Val Arg Gln Ala Pro Gly Gln Gly Leu Glu Trp Ile
            35                  40                  45

Gly Trp Phe Tyr Pro Gly Ser Gly Ser Thr Glu Tyr Ala Glu Lys Phe
        50                  55                  60

Gln Gly Arg Ala Thr Met Thr Ala Asp Asn Ser Ile Ser Thr Val Tyr
65                  70                  75                  80

Met Glu Leu Ser Arg Leu Arg Ser Asp Asp Thr Ala Val Tyr Phe Cys
                85                  90                  95

Glu Arg His Gly Gly Tyr Asp Gly Phe Asp Tyr Trp Gly Gln Gly Thr
                100                 105                 110

Thr Leu Thr Val Ser Ser
            115

<210> SEQ ID NO 136
<211> LENGTH: 113
<212> TYPE: PRT
<213> ORGANISM: Artificial Sequence
<220> FEATURE:
<223> OTHER INFORMATION: LCVR

<400> SEQUENCE: 136

Asp Ile Val Met Ser Gln Ser Pro Asp Ser Leu Ala Val Ser Leu Gly
1               5                   10                  15

Glu Arg Ala Thr Met Asn Cys Lys Ser Ser Gln Ser Leu Leu Tyr Ser
                20                  25                  30

Asn Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Gly Ser Gly Val
        50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Ile Tyr Tyr Cys Gln Gln
                85                  90                  95

Tyr Tyr Ser Tyr Pro Phe Thr Phe Gly Gly Gly Thr Lys Leu Glu Ile
                100                 105                 110

Lys
```